(12) United States Patent
Wilensky et al.

(10) Patent No.: US 9,029,383 B2
(45) Date of Patent: May 12, 2015

(54) METHODS OF TREATMENT OF SKIN ULCERS

(75) Inventors: Robert Wilensky, Ardmore, PA (US); Damir Hamamdzic, Erdenheim, PA (US); Harrilla Profka, Philadelphia, PA (US)

(73) Assignee: The Trustees Of The University of Pennsylvania, Philadelphia, PA (US)

( * ) Notice: Subject to any disclaimer, the term of this patent is extended or adjusted under 35 U.S.C. 154(b) by 516 days.

(21) Appl. No.: 12/599,601

(22) PCT Filed: May 9, 2008

(86) PCT No.: PCT/US2008/063239
§ 371 (c)(1),
(2), (4) Date: Apr. 20, 2010

(87) PCT Pub. No.: WO2008/141176
PCT Pub. Date: Nov. 20, 2008

(65) Prior Publication Data
US 2010/0239565 A1    Sep. 23, 2010

Related U.S. Application Data

(60) Provisional application No. 60/928,759, filed on May 11, 2007.

(51) Int. Cl.
| | | |
|---|---|---|
| A01N 43/54 | (2006.01) | |
| A01N 43/90 | (2006.01) | |
| A61K 31/517 | (2006.01) | |
| A61K 31/519 | (2006.01) | |
| C07D 239/00 | (2006.01) | |
| C07D 239/70 | (2006.01) | |
| A61K 31/135 | (2006.01) | |
| A61K 31/7088 | (2006.01) | |
| C12N 15/113 | (2010.01) | |

(52) U.S. Cl.
CPC ............. *A61K 31/135* (2013.01); *A61K 31/517* (2013.01); *A61K 31/7088* (2013.01); *C12N 15/1137* (2013.01); *C12N 2310/12* (2013.01); *C12N 2310/14* (2013.01); *C12Y 301/01004* (2013.01)

(58) Field of Classification Search
CPC ... A61K 31/513; A61K 31/517; C07D 239/70
USPC ........................ 514/258.1; 544/253
See application file for complete search history.

(56) References Cited

U.S. PATENT DOCUMENTS

| | | | |
|---|---|---|---|
| 4,309,404 A | 1/1982 | DeNeale | |
| 4,405,616 A | 9/1983 | Rajadhyaksha | |
| 4,416,886 A | 11/1983 | Bernstein | |
| 4,556,552 A | 12/1985 | Porter | |
| 4,626,539 A | 12/1986 | Aungst | |
| 4,655,766 A | 4/1987 | Theeuwes | |
| 4,704,295 A | 11/1987 | Porter | |
| 5,034,506 A | 7/1991 | Summerton | |
| 5,177,196 A | 1/1993 | Meyer | |
| 5,223,618 A | 6/1993 | Cook | |
| 5,235,033 A | 8/1993 | Summerton | |
| 5,272,071 A | 12/1993 | Chappel | |
| 5,378,825 A | 1/1995 | Cook | |
| 5,466,786 A | 11/1995 | Buhr | |
| 5,578,461 A | 11/1996 | Sherwin | |
| 5,602,240 A | 2/1997 | Mesmaeker | |
| 5,610,289 A | 3/1997 | Cook | |
| 5,614,617 A | 3/1997 | Cook | |
| 5,672,697 A | 9/1997 | Buhr | |
| 5,705,629 A | 1/1998 | Bhongle | |
| 5,714,606 A | 2/1998 | Acevedo | |
| 5,777,092 A | 7/1998 | Cook | |
| 5,858,988 A | 1/1999 | Wang | |
| 5,981,252 A | 11/1999 | MacPhee | |
| 6,090,923 A | 7/2000 | Wallach | |
| 6,177,257 B1 | 1/2001 | MacPhee | |
| 6,383,220 B1 | 5/2002 | Va'Bliterswijk | |
| 6,649,619 B1 | 11/2003 | Hickey | |
| 7,153,861 B2 | 12/2006 | Leach | |
| 7,169,924 B2 | 1/2007 | Hickey | |
| 2004/0063753 A1 | 4/2004 | Hickey | |
| 2005/0014793 A1 | 1/2005 | Hickey | |
| 2005/0033052 A1 | 2/2005 | Leach | |
| 2006/0106017 A1 | 5/2006 | Jeong | |
| 2007/0015779 A1 | 1/2007 | Griffin | |
| 2007/0078290 A1 | 4/2007 | Esenaliev | |
| 2007/0092529 A1 | 4/2007 | Be | |

FOREIGN PATENT DOCUMENTS

| | | |
|---|---|---|
| EP | 0411893 | 7/1990 |
| EP | 186833 | 8/1992 |
| EP | 0832875 A1 | 4/1998 |
| WO | WO 91/06667 | 5/1991 |
| WO | WO 91/09955 | 7/1991 |
| WO | WO 92/16553 | 10/1992 |
| WO | WO 92/20808 | 11/1992 |
| WO | WO 93/09222 | 5/1993 |
| WO | WO 94/12650 | 6/1994 |
| WO | WO 95/00649 | 1/1995 |

(Continued)

OTHER PUBLICATIONS

Veves et. al., Diabetes, 1998, American Diabetes Association, vol. 47, pp. 457-463.*

(Continued)

*Primary Examiner* — Sarah Pihonak
(74) *Attorney, Agent, or Firm* — Baker & Hostetler LLP

(57) ABSTRACT

Methods for treating and/or preventing skin ulcers are provided featuring administration of pharmaceutical compositions comprising inhibitors of activity or expression Of Lp-PLA$_2$ protein to patients subject to or at risk of developing skin ulcers.

4 Claims, 1 Drawing Sheet

(56) References Cited

FOREIGN PATENT DOCUMENTS

| WO | WO 95/09921 | 4/1995 |
|---|---|---|
| WO | WO 96/13484 | 5/1996 |
| WO | WO 96/19451 | 6/1996 |
| WO | WO 97/02242 | 1/1997 |
| WO | WO 97/21675 | 6/1997 |
| WO | WO 97/21676 | 6/1997 |
| WO | WO 97/41098 | 11/1997 |
| WO | WO 97/41099 | 11/1997 |
| WO | WO 99/24420 | 5/1999 |
| WO | WO 99/32619 | 7/1999 |
| WO | WO 00/10980 | 3/2000 |
| WO | WO 00/66566 | 11/2000 |
| WO | WO 00/66567 | 11/2000 |
| WO | WO 00/68208 | 11/2000 |
| WO | WO 01/60805 | 8/2001 |
| WO | WO 01/68836 | 9/2001 |
| WO | WO 02/30904 | 4/2002 |
| WO | WO 02/30911 | 4/2002 |
| WO | WO 03/016287 | 2/2003 |
| WO | WO 03/041712 | 5/2003 |
| WO | WO 03/042179 | 5/2003 |
| WO | WO 03/042206 | 5/2003 |
| WO | WO 03/042218 | 5/2003 |
| WO | WO 03/086400 | 10/2003 |
| WO | WO 03/087088 | 10/2003 |
| WO | WO 2005/021002 | 3/2005 |
| WO | WO 2006/063791 | 6/2006 |
| WO | WO 2006/063811 | 6/2006 |
| WO | WO 2006/063812 | 6/2006 |
| WO | WO 2006/063813 | 6/2006 |
| WO | WO 2008/141176 | 11/2008 |

OTHER PUBLICATIONS

Zalewki et. al., Arteriosclerosis, Thrombosis, and Vascular Biology, 2005, American Heart Association, vol. 25, pp. 923-931.*

Varet et. al., Cellular and Molecular Life Sciences, 2003, Birkhauser Verlag, vol. 60, pp. 810-819.*

Blackie et al., "The Identification of Clinical Candidate SB-480848: A Potent Inhibitor of Lipoprotein-Associated Phospholipase A2", Bioorganic & Medicinal Chemistry Letters, Elsevier Science, Mar. 24, 2003, 13(6), 1067-1070.

Fivenson et al., "Chemokine and Inflammatory Cytokine Changes During Chronic Wound Healing", Wound Repair and Regneneration, Mosby-Year Book, Oct. 1, 1997, 5(4), 310-322.

Inoue et al., "Lysophosphatidylcholine Increases the Secretion of Matrix Metalloproteinase 2 Through the Activation of NADH/NADPH Oxidase in Cultured Aortic Endothelial Cells", Atherosclerosis, Mar. 1, 2001, 155(1), 45-52.

Marques et al., "Identification of Platelet-Activating Factor Acetylhydrolase II in Human Skin", Journal of Investigative Dermatology, Oct. 2002, 119(4), 913-919.

Shi et al., "Role of Lipoprotein-Associated Phospholipase A2 in Leukocyte Activation and Inflammatory Responses", Atherosclerosis, Elsevier Ireland Ltd., Feb. 13, 2007, 191(1), 54-62.

"Causes of Skin Ulcers", Medical Encyclopedia, Apr. 25, 2007, Retrieved Aug. 18, 2008, http://web.archive.org/web/20070425165659/http://www.nlm.nih.gov/medlineplus/ency, pp. 2-3.

Bartel et al., "MicroRNAs: Genomics, Biogenesis, Mechanism, and Function", Cell, Jan. 23, 2004, 116, 281-297.

Baulcombe, "DNA Events, An RNA Microcosm", Science, Sep. 20, 2002, 297(5589), 2002-2003.

Bergstrom et al., "Pressure Ulcers in Adults: Prediction and Prevention", Clinical Practice Guideline No. 3, AHCPR Pub. No. 92-0047 by the Agency for Health Care Policy and Research (AHCPR), May 1992, 1-47.

Braasch et al., "RNA Interference in Mammalian Cells by Chemically-Modified RNA", Biochemistry, Jul. 8, 2003, 42(26), 7967-7975.

Brillhart, "Pressure Sore and Skin Tear Prevention and Treatment During a 10-Month Program", Rehabil Nurs., May-Jun. 2005, 30(3), 85-91.

Brummelkamp et al., "Stable Suppression of Tumorigenicity by Virus-Mediated RNA Interference", Cancer Cell, Sep. 2002, 2(3), 243-247.

Coburn et al., "Potent and Specific Inhibition of Human Immunodeficiency Virus Type 1 Replication by RNA Interference", J. of Virology, Sep. 2002, 76(18), 9225-9231.

Cole et al., "A Three Year Multiphase Pressure Ulcer Prevalence/Incidence Study in a Regional Referrel Hospital", Wound Manage, Nov. 2004, 50(11), 32-40.

Conde-Taboada et al., "Chronic Leg Ulcers and Basal Cell Carcinoma", J Eur Acad Dermatol Venereol., Mar. 2006, 20(3), 359.

de Laat et al., "Pressure Ulcers: Diagnostics and Interventions Aimed at Wound-Related Complaints: A Review of the Literature", J Clin Nurs., Apr. 2005, 14(4), 464-472.

Elbashir et al., "Duplexes of 21-Nucleotide RNAs Mediate RNA Interference in Cultured Mammalian Cells", Nature, May 24, 2001, 411(6836), 494-498.

Elbashir et al., "RNA Interference is Mediated by 21- and 22-Nucleotide RNAs", Genes & Development, Jan. 15, 2001, 15(2), 188-200.

Frykberg et al., "Diabetic Foot Disorders: A Clinical Practice Guideline. American College of Foot and Ankle Surgeons", J Foot Ankle Surg., (no month available) 2000, 39(5 Suppl), SI-60.

Gamper, "Facile Preparation and Exonuclease Stability of 3'-Modified Oligodeoxynucleotides", Nucleic Acids Res., Jan. 11, 1993, 21(1), 145-150.

GenBank Accession No. U20157, "Human platelet-activating factor acetylhydrolase mRNA, complete cds", Jan. 20, 1995, 2 pages.

GenBank Accession No. NM_005084, "Homo sapiens phospholipase A2, group VII (platelet-activating factor acetylhydrolase, plasma) (PLA2G7), transcript variant 1, mRNA", (no month available) 1995, 4 pages.

GenBank Accession No. NP_005075, "platelet-activating factor acetylhydrolase precursor [Homo sapiens]", (no month available) 1995, 3 pages.

Genetic Engineering & Biotechnology News, "Extended Release Niacin Reduces Cardiovascular Inflammatory Marker Lp-PLA2", Business Wire, Oct. 9, 2006, 1-2.

Genetic Engineering & Biotechnology News, "Study Presented at the ACC Shows Inflammatory Enzyme Lp-PLA2 Predicts Heart Disease Risk in Metabolic Syndrome Patients", Mar. 26, 2007, 1-2.

Glover et al., "A 4-Year Outcome-Based Retrospective Study of Wound Healing and Limb Salvage in Patients with Chronic Wounds", Adv. Wound Care, Jan.-Feb. 1997, 10(1), 33-38.

Grey et al., "Wound Assessment", BMJ, Feb. 4, 2006, 332(7536), 285-288.

Harborth et al., "Identification of Essential Genes in Cultured Mammalian Cells Using Small Interfering RNAs", J. Cell Science, Dec. 2001, 114(Pt 24), 4557-4565.

Harding et al., "Science, Medicine and the Future: Healing Chronic Wounds", BMJ, Jan. 19, 2002, 324(7330), 160-163.

Jackson et al., "Expression Profiling Reveals Off-Target Gene Regulation by RNAi", Nature Biotechnology, Jun. 2003, 21(6), 635-637.

Kazuhiro et al., "Iontophoresis of insulin using a device with microneedles", Int J Pharm Fed World Cong., 2002, 62, 27.

Lagos-Quintana et al., "Identifcation of Tissue-Specific MicroRNAs from Mouse", Current Biology, Apr. 30, 2002, 12(9), 735-739.

Lagos-Quintana et al., "Identification of Novel Genes Coding in Small Expressed RNAs", Science, Oct. 26, 2001, 294(5543), 853-857.

Lagos-Quintana et al., "New MicroRNAs From Mouse and Human", RNA, Feb. 2003, 9(2), 175-179.

Lau et al., "An Abundant Class of Tiny RNAs With Probable Regulatory Roles in Caenorhabditis elegans", Science, Oct. 26, 2001, 294(5543), 858-862.

Lee et al., "An Extensive Class of Small RNAs in Caenorhabditis elegans", Science, Oct. 26, 2001, 294(5543), 862-864.

Lee et al., "Expression of Small Interfering RNAs Targeted Against HIV-1 Rev Transcripts in Human Cells", Nat. Biotechnol., May 2002, 20(5), 500-505.

(56) References Cited

OTHER PUBLICATIONS

Lieber et al., "Selection of Efficient Cleavage Sites in Target RNAs by Using a Ribozyme Expression Library", Mol Cell Biol, Jan. 1995, 15(1), 540-551.
Lim et al., "The MicroRNAs of *Caenorhabditis elegans*", Genes & Development, Apr. 15, 2003, 17(8), 991-1008.
Lim et al., "Vertebrate MicroRNA Genes", Science, Mar. 7, 2003, 299(5612), 1540.
Masters et al., "Short Tandem Report Profiling Provides an International Reference Standard for Human Cell Lines", Proc. Natl. Acad. Scl, USA, Jul. 3, 2001, 98(14), 8012-8017.
McManus et al., "Gene Silencing Using Micro-RNA Designed Hairpins", RNA, Jun. 2002, 8(6), 842-850.
Miyagishi et al., "U6 Promoter-Driven siRNAs With Four Uridine 3' Overhangs Efficiently Suppress Targeted Gene Expression in Mammalian Cells", Nat. Biotechnol., May 2002, 20(5), 497-500.
Nathan et al., "Intensive Diabetes Treatment and Cardiovascular Disease in Patients with Type 1 Diabetes", N. Engl. J. Med., Dec. 22, 2005, 353(25), 2643-2653, PMID 16371630.
Paddison et al., "Short Hairpin RNAs (shRNAs) Induce Sequence-Specific Silencing in Mammalian Cells", Genes Dev., Apr. 15, 2002, 16(8), 948-958.
Paul et al., "Effective Expression of Small Interfering RNA in Human Cells", Nat. Biotechnol., May 2002, 20(5), 505-508.
Petrie et al., "Gene Therapy in Woud Healing", Surgical Clinics of North America, Jun. 2003, 83(3), 597-616.
Phillips et al., "Nonhealing Leg Ulcers: A manifestation of Basil Cell Carcinoma", J. Am. Acad. Dermatol., Jul. 1991, 25(I Pt I), 47-49.
Qin et al., "Inhibiting HIV-1 Infection in Human T Cells by Lentiviral-Mediated Delivery of Small Interfering RNA Against CCR5", Proc. Natl. Acad. Sci. USA, Jan. 7, 2003, 100(1), 183-188.
Reed, "Acridine and Cholesterol-Derivatized Solid Supports for Improved Synthesis of 3'-Modified Oligonucleotides", Bioconjugate Chem., Jul.-Aug. 1991, 2(4), 217-225.
Rubinson et al., "A Lentivirus-Based System to Functionally Silence Genes in Primary Mammalian Cells, Stem Cells and Transgenic Mice by RNA", Nat. Genet., Mar. 2003, 33(3), 401-406.
Scheindlin, "Transdermal Drug Delivery: Past, Present, Future", Molecular Interventions, Dec. 2004, 4(6), 308-312.
Schneider et al., "Building blocks for oligonucleotide analogs with dimethylene-sulfide, -sulfoxide, and -sulfone groups replacing phosphodiester linkages", Tetrahedron Letters, (no month available) 1990, 31(3), 335-339.
Stewart et al., "Lentivirus-Delivered Stable Gene Silencing by RNAi in Primary Cells", RNA, Apr. 2003, 9(4), 493-501.
Sui et al., "A DNA Vector-Based RNAi Technology to Suppress Gene Expression in Mammalian Cells", Proc. Natl. Acad. Scl, USA, Apr. 16, 2002, 99(8), 5515-5520.
Tew et al., "Mechanism of Inhibition of LDL Phospholipase A2 by Monocyclic-beta-lactams. Burst Kinetics and the Effect of Stereochemistry", Biochemistry, Jul. 14, 1998, 37(28), 10087-10093.
The PUSH Tool Version 3.0, Natinal Pressure Ulcer Advisory Panel, Sep. 15, 1998, 2 pages.
Tuschl et al., "Targeted mRNA Degradation by Double-Stranded RNA in Vitro", Genes & Development, Dec. 15, 1999, 13(24), 3191-3197.
Uhlmann et al., "Antisense Oligonucleotides: A New Therapeutic Principle", Chem. Rev., Jun. 1990, 90(4), 543-584.
Wang et al., "Stable and Controllable RNA Interference: Investigating the Physiological Function of Glutathionylated Actin", Proc. Natl. Acad. Sci. USA, Apr. 29, 2003, 100(9), 5103-5106.
Xia et al., "siRNA-Mediated Gene Silencing in Vitro and in Vivo", Nat Biotechnol., Oct. 2002, 20(10), 1006-1010.
Yu et al., "RNA Interference by Expression of Short-Interfering RNAs and Hairpin RNAs in Mammalian Cells", Proc. Natl. Acad. Scl, USA, Apr. 30, 2002, 99(9), 6047-6052.
Zeng et al., "Both Natural and Designed Micro RNAs Can Inhibit the Expression of Cognate mRNAs When Expressed in Human Cells", Mol Cell, Jun. 2002, 9(6), 1327-1333.

\* cited by examiner

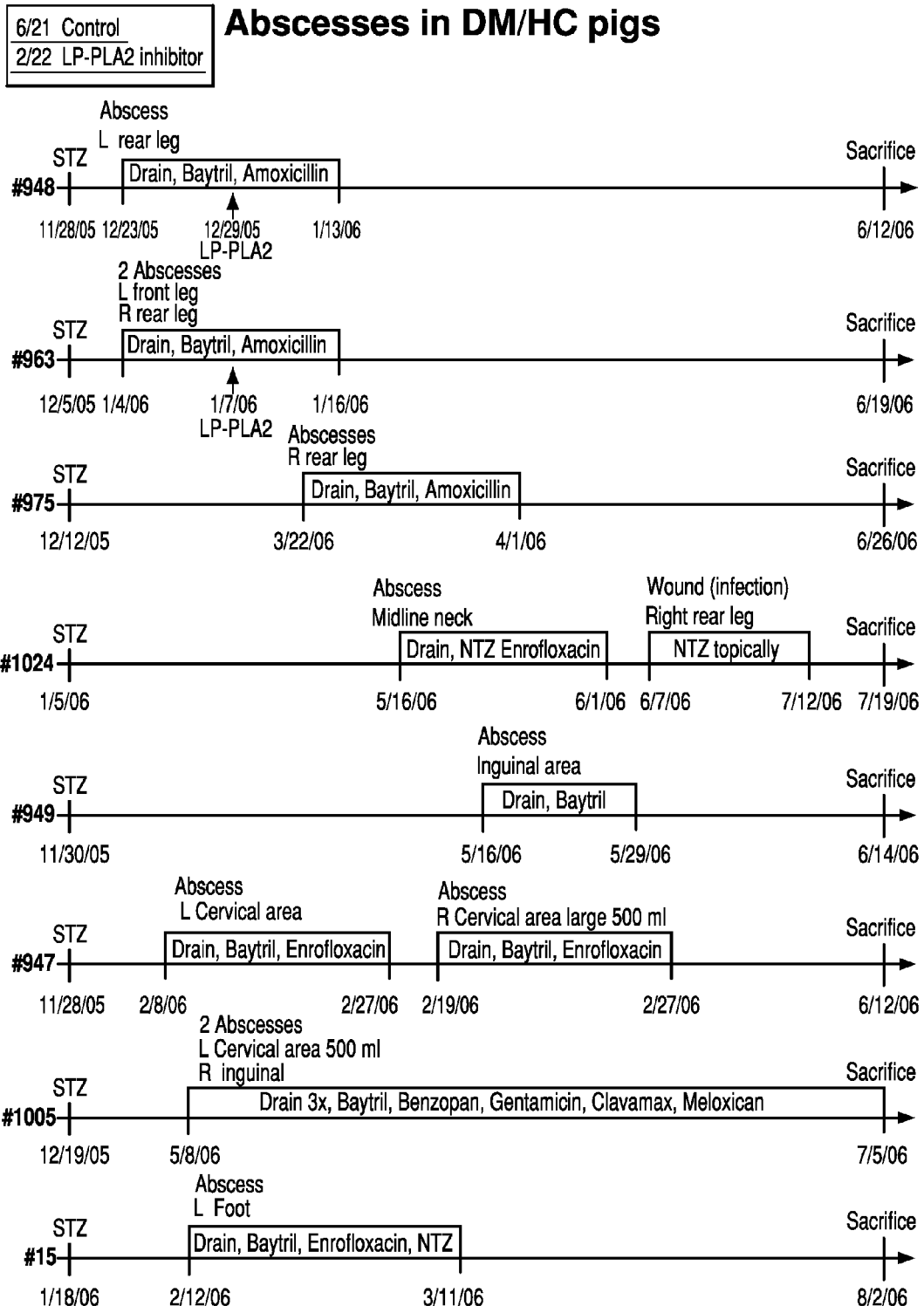

METHODS OF TREATMENT OF SKIN ULCERS

CROSS-REFERENCE TO RELATED APPLICATIONS

This application is the National Stage of International Application No. PCT/US2008/063239, filed May 9, 2008, which claims the benefit of U.S. Provisional Application No. 60/928,759, filed May 11, 2007, the disclosures of which are incorporated herein by reference in their entirety.

FIELD OF INVENTION

Embodiments of the present invention relate generally to methods for the treatment and/or prevention of skin ulcers using agents that inhibit the expression and/or activity of Lp-PLA$_2$ protein.

BACKGROUND

Lipoprotein-Associated Phospholipase A2 (Lp-PLA$_2$), also previously known in the art as Platelet Activating Factor Acetly Hydrolase (PAF acetyl hydrolase) is a member of the super family of phospholipase A$_2$ enzymes that are involved in hydrolysis of lipoprotein lipids or phospholipids. It is secreted by several cells that play a major role in the systemic inflammatory response to injury, including lymphocytes, monocytes, macrophage, T Lymphocytes and mast cells.

During the conversion of LDL to its oxidised form, Lp-PLA$_2$ is responsible for hydrolysing the sn-2 ester of oxidatively modified phosphatidylcholine to give lysophosphatidylcholine and an oxidatively modified fatty acid. Lp-PLA$_2$ hydrolyzes the sn2 position of a truncated phospholipid associated with oxidized LDL. As a result, there is a generation of 2 inflammatory cell homing mediators (non-esterfied fatty acids (NEFA) and LYSO PC). Both NEFA and LYSO PCs are chematractants for circulating monocytes, play a role in the activation of macrophages and increase oxidative stress as well as affecting the functional and the immediate responses of T lymphocytes. Lp-PLA$_2$ is bound in humans and pigs to the LDL molecule via lipoprotein B, and once in the arterial wall the oxidized LDL is susceptible to hydrolysis by Lp-PLA$_2$.

Both of these products of Lp-PLA$_2$ action are potent chemoattractants for circulating monocytes. As such, this enzyme is thought to be responsible for the accumulation of cells loaded with cholesterol ester in the arteries, causing the characteristic 'fatty streak' associated with the early stages of atherosclerosis, and inhibition of the Lp-PLA$_2$ enzyme may be useful in preventing the build up of this fatty streak (by inhibition of the formation of lysophosphatidylcholine), and useful in the treatment of atherosclerosis.

In addition, it is proposed that Lp-PLA$_2$ plays a direct role in LDL oxidation. This is due to the poly unsaturated fatty acid-derived lipid peroxide products of Lp-PLA$_2$ action contributing to and enhancing the overall oxidative process. In keeping with this idea, Lp-PLA$_2$ inhibitors inhibit LDL oxidation. Lp-PLA$_2$ inhibitors may therefore have a general application in any disorder that involves lipid peroxidation in conjunction with the enzyme activity and/or activated inflammatory responses, for example in addition to conditions such as atherosclerosis and diabetes other conditions such as rheumatoid arthritis, myocardial infarction and reperfusion injury.

The skin is the largest organ of the human body. This applies to exterior surface, as it covers the body, appearing to have the largest surface area of all the organs. Moreover, it applies to weight, as it weighs more than any single internal organ, accounting for about 15 percent of body weight. For the average adult human, the skin has a surface area of between 1.5-2.0 square meters, most of it is between 2-3 mm thick. The average square inch of skin holds 650 sweat glands, 20 blood vessels, 60,000 melanocytes, and more than a thousand nerve endings.

As an organ, the skin is an integumentary system made up of multiple layers of epithelial tissues: epidermal, dermis, and hypodermis that guard underlying muscles and organs. As the interface with the surroundings, it plays the most important role in protecting against pathogens, by providing a waterproofing and barrier layer to infection. Its other main functions are insulation and temperature regulation, sensation and vitamin D and B synthesis. Minor excretion of urea and the absorption of oxygen and medicine are also achieved via the skin. Hence the skin is considered one of the most important parts of the body.

When the integrity of the skin is compromised, such as in abrasion or a cut, there is a discontinuity of the multiple layers of epithelial layers and the protective function of the skin is thus locally lost. The human body elicits a localized wound healing response primarily aimed at plugging the epithelial discontinuity and prevent invasion of pathogens. The wound healing response involves increasing blood flow to the wound, mobilizing numerous immune cells (phagocytic macrophages) and inflammatory responses to clear away any pathogens and cell debris, mobilizing fibroblast cells to wound site and secreting extracellular matrix, and seal the wound by regenerating the dermal and epidermal layers.

Sometimes, this wound healing response is impaired or impeded due to various medical conditions and/or repeating trauma, and combinations thereof such that the wound remains as an open sore or ulcer in the skin. This open sore is vulnerable to infection by pathogens in the surrounding area. The skin ulcer may enlarge from infection and aberrant inflammation. Pus (dead immune cells, skin cells, and infectious agents) accumulate in the cavity of the skin ulcer to form an abscess. Abscesses in most parts of the body rarely heal themselves, so prompt medical attention is indicated at the first suspicion of an abscess.

As the skin is the first line of defense against any pathogens in our surroundings, having a chronic ulcer represents a very serious and dangerous medical situation that require immediate and aggressive treatment, and failure to address the problem in a timely manner can lead to dire consequences such as gangrene, lost of appendages resulting from amputation, septicemia, and even death.

Chronic skin wounds are a far-too-common problem in people with diabetes, circulatory problems, cancer, immune system disorders, neurological disorders or limited mobility who are thus either wheelchair bound or bedridden. The limited mobility may be from paralysis due to injuries or disease, or birth defects such as cerebral palsy and spina bifida. Chronic skin ulcer is the major contributing factor to the death of the famous actor Christopher Reeve who was paralyzed in a horse riding accident. The prevalence of skin ulcers can be as high as 60 percent in quadriplegic patients and 66 percent in elderly patients admitted for femoral fracture (See "The Agency for Health Care Policy and Research" Clinical Practice Guideline Number 3, AHCPR Pub. No. 92-0047). For diabetic patients, 15% will develop skin ulcers that are highly susceptible to infection at least once in their lifetime. Indeed, 85% of diabetic amputations performed annually are preceded by ulcers Glover J. L., et. al., 1997, Adv. Wound Care 10:33-38.

It is estimated that in the United States of America alone, there are between 5-7 million people afflicted with chronic skin ulcers (Petrie N, et. al, 2003, Surgical Clinics of North America 83(3):194-9). Annually in America, the total direct cost of chronic wounds, including wound diagnostic and surgical procedures, pharmaceuticals, wound closure devices and hospital and physician charges, amounts to an estimated $20 billion (Frykberg R, et. al., 2000, J Foot Ankle Surg 39(5 Suppl):1-60; Harding K, et. al., 2002, BMJ 324(7330):160-3). The indirect costs of chronic wounds, such as lost work time and impaired quality of life, are not included in this estimate and are difficult to quantify, but can be contemplated to be substantial.

Currently chronic wound management includes medications such as anti-bacterial and anti-fungal drugs, thrombolytic agent or clot-busting agents such as tissue plasminogen activator (tPA), the use of compression bandages, bioengineered skin substitutes (Cultivated Epidermal Allografts), electrical stimulations, advanced drug delivery systems such as iontophoresis-based transdermal delivery system, localized delivery of materials that repair tissue such as platelet derived and autologous growth factor, granulocyte-macrophage colony stimulating factor (G-M CSF), and mesoglycan, negative pressure wound therapy and ultrasound. However, despite a multi-disciplinary approach to treat and promote the healing of chronic skin ulcers with aggressive management of infection and improve blood circulation, chronic skin ulcers continue to be a major clinical problem. Most of the time, doctors have had no way to determine early on which wounds might require these advanced and expensive procedures. Therefore there is still a need for new advancement in the treatment as well as prevention of skin ulcers in people that fall within the high risk population of developing chronic skin ulcers. In addition, there is a pressing need for new advancement in the prevention of recurring episodes of skin ulcers among people at risk.

SUMMARY OF THE INVENTION

The present invention is directed to a method of treating and/or preventing skin ulcers in a subject, comprising administering to the subject in need thereof, a pharmaceutical composition comprising an agent that inhibits the activity and/or the expression of the $Lp-PLA_2$ protein.

One embodiment of the invention is a method of treating and/or preventing skin ulcers in a subject, comprising determining whether said subject has or is at risk of having a skin ulcer, and administering a pharmaceutical composition comprising an agent that inhibits the activity and/or the expression of the $Lp-PLA_2$ protein to the subject having a skin ulcer or at risk of developing a skin ulcer.

Skin ulcers that are capable of being treated by the methods of the present invention are selected from the group consisting of decubitus ulcers, scald ulcers, frost bite ulcers, vascular ulcers, metabolic ulcers, neuropathic ulcers, ulcers accompanying connective tissue diseases, iatrogenic ulcers, factitious ulcers, traumatic ulcers, neoplastic ulcers, ulcers accompanying immunological diseases and disorders and autoimmune diseases, ulcers associated with haematological diseases, ulcers associated with white blood cell disorders, dysproteinaemic ulcers, ulcers due to infection by pathogens, ulcers due to infestation by parasites, and ulcers accompanying to diseases and disorders with unknown etiology.

The risk factors for developing skin ulcers include: having a previous episode of skin ulcer associated with a disease or disorder or trauma that is prone to cause skin ulcers; being elderly; being bedridden; being in a wheelchair; malnourishment; lack of physical activity; excessive alcohol use; urinary incontinence; bowel incontinence; fragile skin; reduced mental ability; smoking; have been diagnosed with or having diabetes; high blood pressure; high levels of homocysteine; being over weight; a family history of varicose veins; suffering from vasculitis; having been diagnosed with a blood-clotting disorder; having an occupation that requires many hours of standing; having sickle-cell anemia; taking bromide-containing medication; taking hydroxyurea-based chemotherapy; renal failure; leprosy; being a burn victim; and frostbite.

In one embodiment, the subject has at least one risk factor. In another embodiment, the subject has at least two risk factors.

In one embodiment, the agent that inhibits the protein activity of $Lp-PLA_2$ is a small molecule, nucleic acid, nucleic acid analogue, protein, antibody, peptide, aptamer or variants or fragments thereof.

In some embodiments, the agent that inhibits the protein activity of $Lp-PLA_2$ is a small molecule, for example but not limited to a small molecule reversible or irreversivle inhibitor of $Lp-PLA_2$ protein. In some embodiments, such a small molecule is a pyrimidione-based compound. In some embodiments, a small molecule inhibitor of $Lp-PLA_2$ is, for example but are not limited to, 1-(N-(2-(diethylamino)ethyl)-N-(4-(4-trifluoromethylphenyl)benzyl)-aminocarbonylmethyl)-2-(4-fluorobenzyl)thio-5,6-trimethylenepyrimidin-4-one (which is also known as SB480848) or a salt thereof. In some embodiments, a small molecule inhibitor of $Lp-PLA_2$ is, for example but not limited to, N-(2-diethylaminoethyl)-2-[2-(2-(2,3-difluorophenyl)ethyl)-4-oxo-4,5,6,7-tetrahydro-cyclopentapyrimidin-1-yl]-N-(4'-trifluoromethyl-biphenyl-4-ylmethyl)¬acetamide or a salt thereof. In some embodiments, a small molecule inhibitor of $Lp-PLA_2$ is, for example but not limited to, N-(1-(2-Methoxyethyl)piperidin-4-yl)-2-[2-(2,3-difluorobenzylthio)-4-oxo-4H-quinolin-1-yl]-N-(4'-trifluoromethylbiphenyl-4-ylmethyl)¬ acetamide; or a salt thereof. In some embodiments, a small molecule inhibitor of $Lp-PLA_2$ is, for example but not limited to, methyl 2-[4-({[2-[2-(2,3-difluorophenyl)ethyl]-4-oxopyrido[2,3-d]pyrimidin-1(4H)-yl]¬ acetyl}{[4'-(trifluoromethyl)-4-biphenylyl]methyl}amino)-1-piperidinyl]-2-methylpropanoate or a salt thereof.

Other forms of inhibitors include a nucleic acid agent which is an RNAi agent such as a siRNA, shRNA, miRNA, dsRNA or ribozyme or variants thereof.

In one embodiment, the agent that inhibits the protein activity of $Lp-PLA_2$ can be administered to the subject together with additional therapeutic agents. These additional therapeutic agents are selected from a group consisting of anti-microbial therapy, anti-parasitic therapy, anti-obesity therapy, diabetes therapy, cardiovascular disease therapy, renal failure therapy, vasculitis therapy, venous insufficiency therapy, arterial insufficiency therapy, cancer therapy, immunosuppressant therapy, immunodeficiency therapy, steroid therapy, burn therapy, and psychotherapy.

In yet another embodiment, the agent that inhibits the protein activity of $Lp-PLA_2$ is administered to the subject together with additional therapeutic agents and the standard wound care management.

In another embodiment, the agent that inhibits the protein activity of $Lp-PLA_2$ is administered to the subject together with bioengineered skin substitutes.

BRIEF DESCRIPTION OF THE DRAWINGS

FIG. 1. Timeline (days) of abscess (pus accumulation in ulcers) development and ulcer treatment in diabetic/hypercholesterolemic (DM/HC) pigs treated with Lp-PLA$_2$ inhibitor, SB480848, and in DM/HC pigs not treated with Lp-PLA$_2$ inhibitor. There were 21 DM/HC pigs I the control, non-treated group and 22 DM/HC pigs in the experimental, treated SB480848 group. Pigs #948 and #963 were treated with Lp-PLA$_2$ inhibitor. These pigs developed abscesses before the start of inhibitor treatment. The abscesses were treated and they healed within average time of 1-2 weeks. No further abscess developed after the initiation of daily single dose of SB480848 inhibitor treatment. Pigs #975, #1024, #949, #947, #1007, and #15 were not treated with Lp-PLA$_2$ inhibitor SB480848. All these pigs developed abscesses, with two pigs having recurrent abscess development, and one pig having a chronic ulceration lasting for over >2 months.

DETAILED DESCRIPTION OF THE INVENTION

Embodiments of the present invention are based on the discovery that DM/HC pigs, when treated with an agent that inhibited the Lp-PLA$_2$ enzyme, failed to develop any skin ulcers. The DM/HC pig model phenotypically demonstrates many similarities to high-risk human diabetic patients. One of the key similarities is the tendency to develop skin abscesses—infected skin ulcers, that are caused by *staphylococcus*, the most commonly isolated microorganism of human diabetic infections. Human diabetic patients are very prone to foot ulcers as a result of complications such as neuropathy, peripheral vascular pathology, and poor healing that are often associated with uncontrolled elevated blood sugar. When the pigs were treated with the Lp-PLA$_2$ enzyme inhibitor SB480848 over a period of 6 months, no pig developed any skin abscesses. Moreover, it was observed that pigs that had active skin abscesses at the beginning of the treatment remained skin abscesses-free once the initial abscess had healed, and the pigs failed to developed recurring episodes of skin abscesses.

Accordingly, one embodiment of the invention is the treatment of skin ulcers in a subject in need thereof by inhibiting the expression and/or activity of Lp-PLA$_2$ protein. Another embodiment of the invention encompasses the prevention of skin ulcers in a subject who had experienced skin ulcers previously, comprising inhibiting the expression and/or activity of Lp-PLA$_2$ protein. In another embodiment, the invention encompasses the prevention of skin ulcers in a subject who is at risk of developing skin ulcers by inhibiting the expression and/or activity of Lp-PLA$_2$ protein.

DEFINITIONS

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

The term "skin ulcer" as used herein refers to an open sore on the skin wherein the epidermis is absent. The underlying dermis or hypodermis may be exposed and visible. The surrounding skin may be reddened and inflamed. The cardinal symptoms and signs of any kind of inflammatory process are redness, heat, swelling, pain and loss of function. Such open sores are prone to infection by pathogens such as bacteria, fungi, and viruses. In advanced cases, the sore may be oozing fluid-pus. Pus (dead immune cells, skin cells, cell fluid, and infectious agents) accumulate in the cavity of the skin ulcer to form an abscess.

The term "disease" or "disorder" is used interchangeably herein, and refers to any alteration in state of the body or of some of the organs, interrupting or disturbing the performance of the functions and/or causing symptoms such as discomfort, dysfunction, distress, or even death to the person afflicted or those in contact with a person. A disease or disorder can also relate to a distemper, ailing, ailment, malady, disorder, sickness, illness, complaint, inderdisposion or affectation.

The term "agent" refers to any entity which is normally not present or not present at the levels being administered in the cell. Agent can be selected from a group comprising: chemicals; small molecules; nucleic acid sequences; nucleic acid analogues; proteins; peptides; aptamers; antibodies; or fragments thereof. A nucleic acid sequence can be RNA or DNA, and can be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA) etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc. A protein and/or peptide or fragment thereof can be any protein of interest, for example, but are not limited to: mutated proteins; therapeutic proteins and truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof. Alternatively, the agent can be intracellular within the cell as a result of introduction of a nucleic acid sequence into the cell and its transcription resulting in the production of the nucleic acid and/or protein inhibitor of Lp-PLA$_2$ within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

The term "inhibiting" as used herein as it pertains to the expression or activity of the protein or polypeptide of pL-PLA$_2$ or variants or homologues thereof does not necessarily mean complete inhibition of expression and/or activity. Rather, expression or activity of the protein, polypeptide or polynucleotide is inhibited to an extent, and/or for a time, sufficient to produce the desired effect. In particular, inhibition of Lp-PLA$_2$ can be determined using an assay for Lp-PLA$_2$ inhibition, for example but not limited to using the bioassay for Lp-PLA$_2$ protein as disclosed herein. Agents that inhibit Lp-PLA$_2$ are agents that inhibit the Lp-PLA$_2$ protein and/or Lp-PLA$_2$ function by at least 10%. In some embodiments, an inhibitor of Lp-PLA$_2$ is an agent that inhibits Lp-PLA$_2$ protein or expression of Lp-PLA$_2$ by at least 10%.

As used herein, the term "Lp-PLA$_2$" refers to the protein target to be inhibited by the methods as disclosed herein. Lp-PLA$_2$ is used interchangeably with Lp-PLA$_2$ and lipoprotein associated phospholipase A2, also previously known in the art as Platelet Activating Factor Acetyl Hydrolase (PAF acetyl hydrolase). Human Lp-PLA$_2$ is encoded by nucleic acid corresponding to accession No: U20157 (SEQ ID NO:1) or Ref Seq ID: NM_005084 (SEQ ID NO:2) or and the human Lp-PLA$_2$ corresponds to protein sequence corresponding to accession No: NP_005075 (SEQ ID NO:3), which are disclosed in U.S. Pat. No. 5,981,252, which is specifically incorporated herein in its entirety by reference.

As used herein, "gene silencing" or "gene silenced" in reference to an activity of n RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA, including but are not limited to, siRNAi, shRNAi, endogenous microRNA and artificial microRNA. For instance, it includes sequences previously identified as siRNA, regardless of the mechanism of downstream processing of the RNA (i.e. although siRNAs are believed to have a specific method of in vivo processing resulting in the cleavage of mRNA, such sequences can be incorporated into the vectors in the context of the flanking sequences described herein).

As used herein an "siRNA" refers to a nucleic acid that forms a double stranded RNA, which double stranded RNA has the ability to reduce or inhibit expression of a gene or target gene when the siRNA is present or expressed in the same cell as the target gene, for example Lp-PLA$_2$. The double stranded RNA siRNA can be formed by the complementary strands. In one embodiment, a siRNA refers to a nucleic acid that can form a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNA are small RNAs naturally present in the genome which are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 116: 281-297), comprises a dsRNA molecule.

The terms "subject," "individual" and "patient" are used interchangeably herein, and refer to an animal, for example a human, to whom treatment, including prophylactic treatment, with the pharmaceutical composition according to the present invention, is provided. The term "subject" as used herein refers to human and non-human animals. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model.

The term "gene" used herein can be a genomic gene comprising transcriptional and/or translational regulatory sequences and/or a coding region and/or non-translated sequences (e.g., introns, 5'- and 3'-untranslated sequences and regulatory sequences). The coding region of a gene can be a nucleotide sequence coding for an amino acid sequence or a functional RNA, such as tRNA, rRNA, catalytic RNA, siRNA, miRNA and antisense RNA. A gene can also be an mRNA or cDNA corresponding to the coding regions (e.g. exons and miRNA) optionally comprising 5'- or 3' untranslated sequences linked thereto. A gene can also be an amplified nucleic acid molecule produced in vitro comprising all or a part of the coding region and/or 5'- or 3'-untranslated sequences linked thereto.

The term "nucleic acid" or "oligonucleotide" or "polynucleotide" used herein can mean at least two nucleotides covalently linked together. As will be appreciated by those in the art, the depiction of a single strand also defines the sequence of the complementary strand. Thus, a nucleic acid also encompasses the complementary strand of a depicted single strand. As will also be appreciated by those in the art, many variants of a nucleic acid can be used for the same purpose as a given nucleic acid. Thus, a nucleic acid also encompasses substantially identical nucleic acids and complements thereof. As will also be appreciated by those in the art, a single strand provides a probe for a probe that can hybridize to the target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

A nucleic acid will generally contain phosphodiester bonds, although nucleic acid analogs can be included that can have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog can be located for example at the 5'-end and/or the 3'-end of the nucleic acid molecule. Representative examples of nucleotide analogs can be selected from sugar- or backbone-modified ribonucleotides. It should be noted, however, that also nucleobase-modified ribonucleotides, i.e. ribonucleotides, containing a non naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7 deaza-adenosine; O- and N-alkylated nucleotides, e.g. N6-methyl adenosine are suitable. The 2' OH— group can be replaced by a group selected from H. OR, R. halo, SH, SR, NH2, NHR, NR2 or CN, wherein R is C—C6 alkyl, alkenyl or alkynyl and halo is F, Cl, Br or I. Modifications of the ribose-phosphate backbone can be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs can be made.

The term "vector" used herein refers to a nucleic acid sequence containing an origin of replication. A vector can be a plasmid, bacteriophage, bacterial artificial chromosome or yeast artificial chromosome. A vector can be a DNA or RNA vector. A vector can be either a self replicating extrachromosomal vector or a vector which integrate into a host genome.

As used herein, the term "treating" includes reducing or alleviating at least one adverse effect or symptom of a condition, disease or disorder associated with a skin ulcer.

Treatment is generally considered "effective" if an improvement of at least one stage or level of classification in a clinically accepted scale of lesion or ulcer severity is achieved upon treatment with an Lp-PLA$_2$ inhibitor. Alternatively, or in addition, a reduction in the size (area and/or depth) of a skin lesion by at least 25% following treatment is considered "effective" treatment.

The efficacy of prevention is monitored by evaluating the skin of the subject at risk of developing a skin lesion following the commencement of treatment with an Lp-PLA$_2$ inhibitor. The absence of skin lesions in an at-risk individual is considered a sign of "effective" prevention. Similarly, where an individual has a history of skin lesions, the absence of new lesions, or even a reduction, e.g., by 50% or more, in the frequency or severity of any new lesions is indicative of "effective" prevention of skin ulcers by the methods described herein.

The term "effective amount" as used herein refers to the amount of therapeutic agent of pharmaceutical composition to provide "effective" treatment as that term is defined herein. An effective amount as used herein would also include an amount sufficient to prevent or delay the development of a symptom of the disease, alter the course of a symptom disease (for example but not limited to, slow the progression of a symptom of the disease), or reverse a symptom of the disease.

As used herein, the terms "administering," and "introducing" are used interchangeably and refer to the placement of the agents that inhibit Lp-PLA$_2$ as disclosed herein into a subject by a method or route which results in at least partial localization of the agents at a desired site. The compounds of the present invention can be administered by any appropriate route which results in an effective treatment in the subject.

The term "vectors" is used interchangeably with "plasmid" to refer to a nucleic acid molecule capable of transporting another nucleic acid to which it has been linked. Vectors capable of directing the expression of genes and/or nucleic acid sequence to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. Other expression vectors can be used in different embodiments of the invention, for example, but are not limited to, plasmids, episomes, bacteriophages or viral vectors, and such vectors can integrate into the host's genome or replicate autonomously in the particular cell. Other forms of expression vectors known by those skilled in the art which serve the equivalent functions can also be used. Expression vectors comprise expression vectors for stable or transient expression encoding the DNA.

The articles "a" and "an" are used herein to refer to one or to more than one (i.e., to at least one) of the grammatical object of the article. By way of example, "an element" means one element or more than one element.

As used here, "iatrogenic" means induced in a patient by a physician's activity, manner, or therapy. For example, induced by drug therapy for a certain disease or disorder.

Lp-PLA$_2$: General Information

Lp-PLA$_2$ is also referred to in the art as aliases Lp-PLA$_2$, LDL-PLA$_2$, lipoprotein associated phospholipase A2, PLA2G7, phospholipase A2 (group VII), or Platelet Activating Factor Acetyl Hydrolase (PAF acetyl hydrolase or PAFAH). Human Lp-PLA$_2$ is encoded by nucleic acid corresponding to GenBank Accession No: U20157 (SEQ ID NO:1) or Ref Seq ID: NM__005084 (SEQ ID NO:2) and the human Lp-PLA2 corresponds to protein sequence corresponding to GenBank Accession No: NP__005075 (SEQ ID NO:3), which are disclosed in U.S. Pat. No. 5,981,252, which is specifically incorporated herein in its entirety by reference.

Phospholipase A2 enzyme Lipoprotein Associated Phospholipase A2 (Lp-PLA$_2$), the sequence, isolation and purification thereof, isolated nucleic acids encoding the enzyme, and recombinant host cells transformed with DNA encoding the enzyme are disclosed in WO 95/00649 (SmithKline Beecham plc), which is specifically incorporated herein in its entirety by reference. A subsequent publication from the same group further describes this enzyme (Tew D et al, Arterioscler Thromb Vas Biol 1996:16; 591-9) wherein it is referred to as LDL PLA$_2$ and later patent application (WO 95/09921, Icos Corporation) and a related publication in Nature (Tjoelker et al, vol 374, 6 Apr. 1995, 549) describe the enzyme PAF-AH which has essentially the same sequence as Lp-PLA$_2$.

It has been shown that Lp-PLA2 is responsible for the conversion of phosphatidylcholine to lysophosphatidylcholine, during the conversion of low density lipoprotein (LDL) to its oxidised form. The enzyme is known to hydrolyse the sn-2 ester of the oxidised phosphatidylcholine to give lysophosphatidylcholine and an oxidatively modified fatty acid.

Both products of Lp-PLA$_2$ action are biologically active with lysophosphatidylcholine, in particular having several pro-atherogenic activities ascribed to it including monocyte chemotaxis and induction of endothelial dysfunction, both of which facilitate monocyte-derived macrophage accumulation within the artery wall.

Agents that Inhibit Lp-PLA$_2$

In some embodiments, the present invention relates to the inhibition of Lp-PLA$_2$. In some embodiments, inhibition is inhibition of nucleic acid transcripts encoding Lp-PLA$_2$, for example inhibition of messenger RNA (mRNA). In alternative embodiments, inhibition of Lp-PLA$_2$ is inhibition of the expression and/or inhibition of activity of the gene product of Lp-PLA$_2$, for example the polypeptide or protein of Lp-PLA$_2$, or isoforms thereof. As used herein, the term "gene product" refers to RNA transcribed from a gene, or a polypeptide encoded by a gene or translated from RNA.

In some embodiments, inhibition of Lp-PLA$_2$ is by an agent. One can use any agent, for example but are not limited to nucleic acids, nucleic acid analogues, peptides, phage, phagemids, polypeptides, peptidomimetics, ribosomes, aptamers, antibodies, small or large organic or inorganic molecules, or any combination thereof. In some embodiments, agents useful in methods of the present invention include agents that function as inhibitors of Lp-PLA expression, for example inhibitors of mRNA encoding Lp-PLA.

Agents useful in the methods as disclosed herein can also inhibit gene expression (i.e. suppress and/or repress the expression of the gene). Such agents are referred to in the art as "gene silencers" and are commonly known to those of ordinary skill in the art. Examples include, but are not limited to a nucleic acid sequence, for an RNA, DNA or nucleic acid analogue, and can be single or double stranded, and can be selected from a group comprising nucleic acid encoding a protein of interest, oligonucleotides, nucleic acids, nucleic acid analogues, for example but are not limited to peptide nucleic acid (PNA), pseudo-complementary PNA (pc-PNA), locked nucleic acids (LNA) and derivatives thereof etc. Nucleic acid agents also include, for example, but are not limited to nucleic acid sequences encoding proteins that act as transcriptional repressors, antisense molecules, ribozymes, small inhibitory nucleic acid sequences, for example but are not limited to RNAi, shRNAi, siRNA, micro RNAi (miRNA), antisense oligonucleotides, etc.

As used herein, agents useful in the method as inhibitors of Lp-PLA$_2$ expression and/or inhibition of Lp-PLA$_2$ protein function can be any type of entity, for example but are not limited to chemicals, nucleic acid sequences, nucleic acid analogues, proteins, peptides or fragments thereof. In some embodiments, the agent is any chemical, entity or moiety, including without limitation, synthetic and naturally-occurring non-proteinaceous entities. In certain embodiments the agent is a small molecule having a chemical moiety. For example, in some embodiments, the chemical moiety is a pyrimidione-based compound as disclosed herein.

In alternative embodiments, agents useful in the methods as disclosed herein are proteins and/or peptides or fragment thereof, which inhibit the gene expression of Lp-PLA$_2$ or the function of the Lp-PLA$_2$ protein. Such agents include, for example but are not limited to protein variants, mutated proteins, therapeutic proteins, truncated proteins and protein fragments. Protein agents can also be selected from a group comprising mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof.

Alternatively, agents useful in the methods as disclosed herein as inhibitors of Lp-PLA$_2$ can be a chemicals, small molecule, large molecule or entity or moiety, including without limitation synthetic and naturally-occurring non-proteinaceous entities. In certain embodiments the agent is a small molecule having the chemical moieties as disclosed herein.

Small Molecules

In some embodiments, agents that inhibit Lp-PLA$_2$ are small molecules. Irreversible or reversible inhibitors of Lp-PLA$_2$ can be used in the methods of the present invention.

Irreversible inhibitors of Lp-PLA$_2$ are disclosed in patent applications WO 96/13484, WO96/19451, WO 97/02242, WO97/217675, WO97/217676, WO 97/41098, and WO97/41099 (SmithKline Beecham plc) which are specifically incorporated in their entirety herein by reference and disclose inter alia various series of 4 thionyl/sulfinyl/sulfonyl azetidinone compounds which are inhibitors of the enzyme Lp-PLA$_2$. These are irreversible, acylating inhibitors (Tew et al, Biochemistry, 37, 10087, 1998).

Lp-PLA$_2$ inhibitors effective in humans are commonly known by persons of ordinary skill and include those undergoing evaluation, for example undergoing pre-clinical and clinical assessment including Phase II clinical trials. A number of applications have been filed and published by SmithKline Beecham and its successor GlaxoSmithKline. A list of relevant published applications assigned to same is: WO01/60805, WO02/30904, WO03/016287, WO00/66567, WO03/042218, WO03/042206, WO03/042179, WO03/041712, WO03/086400, WO03/087088, WO02/30911, WO99/24420, WO00/66566, WO00/68208, WO00/10980, and WO2005/021002, which are specifically incorporated in their entirety herein by reference. In addition, reference is made to U.S. provisional applications 60/829,328 and 60/829,327, both having been filed 13 Oct. 2006, which are also specifically incorporated in their entirety herein by reference.

Other Lp-PLA$_2$ inhibitors useful in the methods as disclosed herein are described in published patent applications, for example WO2006063791-A1, WO2006063811-A1, WO2006063812-A1, WO2006063813-A1, all in the name of Bayer Healthcare; and US2006106017-A1 assigned to Korea Res. Inst. Bioscience & Biotechnology, which are specifically incorporated in their entirety herein by reference. Lp-PLA$_2$ inhibitors also include known agents, for example but not limited to include the use of statins with Niacin (see www.genengnews.com/news/bnitem.aspx?name=6724568) and fenofibrate (see www.genengnews.com/news/bnitem.aspx?name=14817756&taxid=19).

All of the applications set out in the above paragraphs are incorporated herein by reference. It is believed that any or all of the compounds disclosed in these documents are useful for prophylaxis or treatment of skin ulcers. The porcine model of diabetic skin ulcers described herein and exemplified in the Example can be used by one of ordinary skill in the art to determine which of the disclosed compounds or other inhibitors of Lp-PLA$_2$, for example antibodies, small molecules or RNAi are effective for the treatment or prevention of skin ulcers as claimed herein.

In a particular embodiment, Lp-PLA$_2$ inhibitors as disclosed in U.S. Pat. Nos. 6,649,619 and 7,153,861, which are specifically incorporated in their entirety herein by reference (and International Application WO 01/60805) and U.S. Pat. No. 7,169,924 which is incorporated in its entirety herein by reference (and International Patent Application WO 02/30911), are useful in the methods disclosed herein for the prophylaxis or for the treatment of skin ulcers. In some embodiments, the Lp-PLA$_2$ inhibitors as disclosed in U.S.

publication No. 2005/0033052A1, which is incorporated in its entirety herein by reference, and International Patent Applications WO 02/30904, WO 03/042218, WO 03/042206, WO03/042179, WO 03/041712, WO 03/086400, and WO 03/87088 are reversible Lp-PLA$_2$ inhibitors.

Formula (I) One can use a group of reversible Lp-PLA$_2$ inhibitors that are disclosed in international application WO 01/60805, from which arose U.S. Pat. Nos. 6,649,619 and 7,153,861 which are incorporated in their entirety herein by reference, the disclosures of which are incorporated herein in full, as though set out within this document. A narrower group of compounds of interest are those of formula (I) described in WO 01/60805 and claimed in U.S. Pat. Nos. 6,649,619 and 7,153,861, namely:

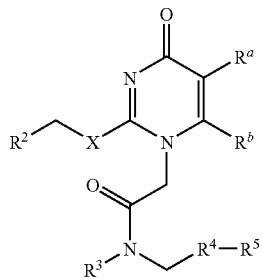

(I)

wherein:
Ra and Rb together with the pyrimidine ring carbon atoms to which they are attached form a fused 5-membered carbocyclic ring;
R2 is phenyl, substituted by one to three fluorine atoms;
R3 is methyl or C(1-3)alkyl substituted by NR8R9; or
R3 is Het C(0 2)alkyl in which Het is a 5- to 7-membered heterocyclyl ring having N and in which N is unsubstituted or substituted by C(1 6)alkyl;
R4 and R5 together form a 4-(4-trifluoromethylphenyl) phenyl moiety;
R8 and R9 which can be the same or different are selected from the group consisting of hydrogen, or C(1 6)alkyl);
X is S, or a pharmaceutically acceptable salt thereof.

Of even more interest are the following compounds, all within the scope of formula (I) and disclosed in the application and patents noted above:
1-(N-(2-(diethylamino)ethyl)-N-(4-(4-trifluoromethylphenyl)benzyl)-aminocarbonylmethyl)-2-(4-fluorobenzyl) thio-5,6-trimethylenepyrimidin-4-one, used in the pig study described herein;
1-(N-(2-(diethylamino)ethyl)-N-(4-(4-trifluoromethylphenyl)benzyl)¬ aminocarbonylmethyl)-2-(2,3-difluorobenzyl)thio-5,6-trimethylenepyrimidin-4-one;
1-(N-(2-(diethylamino)ethyl)-N-(4-(4-trifluoromethylphenyl)benzyl)aminocarbonylmethyl)-2-(3,4-difluorobenzyl) thio-5,6-trimethylenepyrimidin-4-one;
1-(N-(2-(diethylamino)ethyl)-N-(4-(4-trifluoromethylphenyl)benzyl)aminocarbonylmethyl)-2-(2,3,4-trifluorobenzyl)thio-5,6-trimethylenepyrimidin-4-one;
1-(N-(2-(diethylamino)ethyl)-N-(4-(4-trifluoromethylphenyl)benzyl)amino¬ carbonylmethyl)-2-(2-fluorobenzyl) thio-5,6-trimethylenepyrimidin-4-one;
1-(N-methyl-N-(4-(4-trifluoromethylphenyl)benzyl)aminocarbonylmethyl)-2-(4-fluorobenzyl)thio-5,6-trimethylenepyrimidin-4-one;
1-(N-(2-(1-piperidino)ethyl)-N-(4-(4-trifluoromethylphenyl)benzyl)amino¬ carbonylmethyl)-2-(4-fluorobenzyl) thio-5,6-trimethylenepyrimidin-4-one;
1-(N-(1-ethylpiperidin-4-yl)-N-(4-(4-trifluoromethylphenyl)benzyl)amino¬ carbonylmethyl)-2-(4-fluorobenzyl) thio-5,6-trimethylenepyrimidin-4-one;
1-(N-(2-ethylamino-2-methylpropyl)-N-(4-(4-trifluoromethylphenyl)benzyl)¬ aminocarbonylmethyl)-2-(4-fluorobenzyl)thio-5,6-trimethylenepyrimidin-4-one;
N-(2-tert-butylaminoethyl)-N-(4-(4-trifluoromethylphenyl)benzyl)amino¬ carbonylmethyl)-2-(4-fluorobenzyl)thio-5,6-trimethylenepyrimidin-4-one;
1-(N-(1-methylpiperidin-4-yl)-N-(4-(4-trifluoromethylphenyl)benzyl)¬ aminocarbonylmethyl)-2-(4-fluorobenzyl) thio-5,6-trimethylenepyrimidin-4-one;
1-(N-(1-isopropylpiperidin-4-yl)-N-(4-(4-trifluoromethylphenyl)benzyl)¬ aminocarbonylmethyl)-2-(4-fluorobenzyl)thio-5,6-trimethylenepyrimidin-4-one;
1-(N-(1-(2-methoxyethyl)piperidin-4-yl)-N-(4-(4-trifluoromethylphenyl)benzyl)-aminocarbonylmethyl)-2-(4-fluorobenzyl)thio-5,6-trimethylenepyrimidin-4-one;
1-(N-(2-(ethylamino)ethyl)-N-(4-(4-trifluoromethylphenyl)benzyl)¬ aminocarbonylmethyl)-2-(4-fluorobenzyl)thio-5,6-trimethylenepyrimidin-4-one; or a pharmaceutically acceptable salt of these compounds.

Methods for preparing these compounds are disclosed in the noted documents.

A second process for making 1-(N-(2-(diethylamino) ethyl)-N-(4-(4-trifluoromethylphenyl)benzyl)-aminocarbonylmethyl)-2-(4-fluorobenzyl)thio-5,6-trimethylenepyrimidin-4-one can be found in application WO 03/016287 (U.S. publication No 20050014793A1), which is incorporated herein by reference in its entirety.

Formula (II)
A further group of compounds which can be useful in practicing the methods of this invention are disclosed in WO 02/30911; U.S. Pat. No. 7,169,924 corresponds to this international application. Both are incorporated herein in full. The generic formula in that case, represented here as formula (II), is as follows:

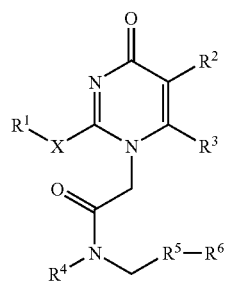

(II)

in which:
R1 is an aryl group, optionally substituted by 1, 2, 3 or 4 substituents which can be the same or different selected from C(1-6)alkyl, C(1-6)alkoxy, C(1-6)alkylthio, hydroxy, halogen, CN, and mono to perfluoro-C(1 4)alkyl;
R2 is halogen, C(1 3)alkyl, C(1 3)alkoxy, hydroxyC(1 3)alkyl, C(1 3)alkylthio, C(1 3)alkylsulphinyl, aminoC(1-3) alkyl, mono- or di-C(1-3)alkylaminoC(1-3)alkyl, C(1 3)alkylcarbonylaminoC(1-3)alkyl, C(1 3)alkoxyC(1 3)alkylcarbonylaminoC(1-3)alkyl, C(1 3)alkylsulphonylaminoC(1-3) alkyl, C(1 3)alkylcarboxy, C(1 3)alkylcarboxyC(1 3)alkyl, and
R3 is hydrogen, halogen, C(1-3)alkyl, or hydroxyC(1-3) alkyl; or R2 and R3 together with the pyrimidone ring carbon atoms to which they are attached form a fused 5- or 6-membered carbocyclic ring; or R2 and R3 together with the pyrimidone ring carbon atoms to which they are attached form a fused benzo or heteroaryl ring optionally substituted by 1, 2, 3 or 4 substituents which can be the same or different selected from halogen, C(1 4)alkyl, cyano, C(1-6)alkoxy, C(1-6)alkylthio or mono to perfluoro-C(1-4)alkyl;

R4 is hydrogen, C(1-6)alkyl which can be unsubstituted or substituted by 1, 2 or 3 substituents selected from hydroxy, halogen, OR7, COR7, carboxy, COOR7, CONR9R10, NR9R10, NR7COR8, mono- or di(hydroxyC(1 6)alkyl) amino and N hydroxyC(1-6)alkyl-N C(1-6)alkylamino; or R4 is Het-C(0-4)alkyl in which Het is a 5- to 7-membered heterocyclyl ring comprising N and optionally O or S, and in which N can be substituted by COR7, COOR7, CONR9R10, or C(1 6)alkyl optionally substituted by 1, 2 or 3 substituents selected from hydroxy, halogen, OR7, COR7, carboxy, COOR7, CONR9R10 or NR9R10, for instance, piperidin-4-yl, pyrrolidin-3-yl;

R5 is an aryl or a heteroaryl ring optionally substituted by 1, 2, 3 or 4 substituents which can be the same or different selected from C(1-6)alkyl, C(1-6)alkoxy, C(1 6)alkylthio, arylC(1-6)alkoxy, hydroxy, halogen, CN, COR7, carboxy, COOR7, NR7COR8, CONR9R10, SO2NR9R10, NR7SO2R8, NR9R10, mono to perfluoro-C(1 4)alkyl and mono to perfluoro-C(1 4)alkoxy;

R6 is an aryl or a heteroaryl ring which is further optionally substituted by 1, 2, 3 or 4 substituents which can be the same or different selected from C(1-18)alkyl, C(1-18)alkoxy, C(1 6)alkylthio, C(1 6)alkylsulfonyl, arylC(1-6)alkoxy, hydroxy, halogen, CN, COR7, carboxy, COOR7, CONR9R10, NR7COR8, SO2NR9R10, NR7SO2R8, NR9R10, mono to perfluoro-C(1 4)alkyl and mono to perfluoro-C(1 4)alkoxy, or C(5-10)alkyl;

R7 is hydrogen or C(1-12)alkyl, for instance C(1-4)alkyl (e.g. methyl or ethyl);

R8 is hydrogen, OC(1-6)alkyl, or C(1-12)alkyl, for instance C(1-4)alkyl (e.g. methyl or ethyl);

R9 and R10 which can be the same or different is each selected from hydrogen, or C(1 12)alkyl, or R9 and R10 together with the nitrogen to which they are attached form a 5- to 7 membered ring optionally containing one or more further heteroatoms selected from oxygen, nitrogen and sulphur, and optionally substituted by one or two substituents selected from hydroxy, oxo, C(1-4)alkyl, C(1-4)alkylcarboxy, aryl, e.g. phenyl, or aralkyl, e.g benzyl, for instance morpholine or piperazine; and X is C(2-4)alkylene, optionally substituted by 1, 2 or 3 substituents selected from methyl and ethyl, or CH═CH.

All salts of formula (II), as well, can be used in the instant method of treatment.

Of particular interest are the compounds of formula (II) here, where, as noted in WO 02/30911 for formula (I) there, R1 can be a phenyl group optionally substituted by 1, 2, 3 or 4 substituents which can be the same or different selected from halo, C1-C6 alkyl, trifluoromethyl or C1-C6 alkoxy. More specifically, phenyl is unsubstituted or substituted by 1, 2, 3 or 4 halogen substituents, particularly, from 1 to 3 fluoro groups, and most particularly, 2,3-difluoro, 2,4-difluoro or 4-fluoro.

A further embodiment of formula (II) here, is where Y is —CH2CH2-.

In addition, of interest are compounds of formula (II) where R2 is hydrogen, by default, or is halo, C1-C6 alkyl, mono to perfluoro-C1-C4 alkyl, mono to perfluoro C1-C46 alkoxy, or C1-C6 alkoxy; particularly mono to perfluoro-C1-C4 alkyl, mono to perfluoro-C1-C4 alkoxy, or C1-C6 alkoxy. Of particular interest are the compounds of formula (II) where R2 is other than hydrogen, n in (R2)n is 1, 2, or 3, and the substitution pattern is meta and/or para, particularly para, i.e. a 4-position substituent. See also those compounds where R2 is 4-trifluoromethyl or 4-trifluoromethoxy.

R3 and R4 can be the same or different and are methyl, ethyl, n-propyl, or n-butyl. Of particular interest are those compounds of formula (II) herein where R3 and R4 are the same and are methyl, or ethyl; methyl is of particular interest.

R5 can be hydrogen, C(1-6) alkyl which is a straight chain, or branched. Of particular interest is methyl, ethyl, propyl, isopropyl, n-butyl, sec-butyl, iso-butyl, t-butyl, n-pentyl or n-hexyl.

It will be appreciated that within the compounds of formula (II) herein there is a further sub-group of compounds in which:

R1 is phenyl substituted by 2,3 difluoro;

R2 and R3, together with the pyrimidine ring carbon atoms to which they are attached, form a fused 5-membered cyclopentenyl ring;

R4 is 2-(diethylamino)ethyl;

R5 is phenyl;

R6 is phenyl substituted by trifluoromethyl at the 4-position, or thien-2-yl substituted by trifluoromethyl in the 5-position; and X is (CH2)2.

Particular compounds of formula (II) herein of interest are:

N-(2-diethylaminoethyl)-2-[2-(2-(2,3-difluorophenyl) ethyl)-4-oxo-4,5,6,7-tetrahydro-cyclopentapyrimidin-1-yl]-N-(4'-trifluoromethyl-biphenyl-4-ylmethyl)¬ acetamide;

N-(2-diethylaminoethyl)-2-[2-(2-(2,3-difluorophenyl) ethyl)-4-oxo-4,5,6,7-tetrahydro-cyclopentapyrimidin-1-yl]-N-(4'-trifluoromethyl-biphenyl-4-ylmethyl)¬ acetamide bitartrate;

N-(2-ethylamino-2-methyl-propyl)-2-(2-(2-(2,3-difluorophenyl)-ethyl)-4-oxo-4,5,6,7-tetrahydro-cyclopentapyrimidin-1-yl)-N-(4'-trifluoromethyl-biphenyl-4-yl-methyl)¬ acetamide bitartrate;

N-(2-t-butylaminoethyl)-2-(2-(2-(2,3-difluorophenyl)-ethyl)-4-oxo-4,5,6,7-tetrahydro-cyclopentapyrimidin-1-yl)-N-(4'-trifluoromethyl-biphenyl-4-ylmethyl)¬ acetamide bitartrate;

N-(1-ethyl-piperidin-4-yl)-2-(2-(2-(2,3-difluorophenyl)-ethyl)-4-oxo-4,5,6,7-tetrahydro-cyclopentapyrimidin-1-yl)-N-(4'-trifluoromethyl-biphenyl-4-ylmethyl)¬ acetamide bitartrate;

N-(2-diethylaminoethyl)-2-(2-(2-(4-fluoro-2-(trifluoromethyl)phenyl)-ethyl)-4-oxo-4,5,6,7-tetrahydro-cyclopentapyrimidin-1-yl)-N-(4'-trifluoromethyl-biphenyl-4-ylmethyl)¬ acetamide bitartrate;

N-(2-diethylaminoethyl)-2-(2-(2-(4-fluoro-3-(trifluoromethyl)phenyl)-ethyl)-4-oxo-4,5,6,7-tetrahydro-cyclopentapyrimidin-1-yl)-N-(4'-trifluoromethyl-biphenyl-4-ylmethyl)¬ acetamide bitartrate;

N-(2-diethylaminoethyl)-2-(2-(2-(3-chloro-4-fluorophenyl)-ethyl)-4-oxo-4,5,6,7-tetrahydro-cyclopentapyrimidin-1-yl)-N-(4'-trifluoromethyl-biphenyl-4-ylmethyl)¬ acetamide bitartrate;

(+/−)-N-(2-diethylaminoethyl)-2-(2-phenyl-propyl)-4-oxo-4,5,6,7-tetrahydro-cyclopentapyrimidin-1-yl)-N-(4'-trifluoromethyl-biphenyl-4-ylmethyl)¬ acetamide bitartrate;

N-(2-diethylaminoethyl)-2-(2-(2-(2,4-difluorophenyl)-ethyl)-4-oxo-4,5,6,7-tetrahydro-cyclopentapyrimidin-1-yl)-N-(4'-trifluoromethyl-biphenyl-4-ylmethyl)¬ acetamide bitartrate;

N-(2-diethylaminoethyl)-2-(2-(2-(2,5-difluorophenyl)-ethyl)-4-oxo-4,5,6,7-tetrahydro-cyclopentapyrimidin-1-yl)-N-(4'-trifluoromethyl-biphenyl-4-ylmethyl)¬ acetamide bitartrate;

N-(2-diethylaminoethyl)-2-(2-(2-(3,4-difluorophenyl)-ethyl)-4-oxo-4,5,6,7-tetrahydro-cyclopentapyrimidin-1-yl)-N-(4'-trifluoromethyl-biphenyl-4-ylmethyl)¬ acetamide;

N-(2-diethylaminoethyl)-2-(2-(2-(2-fluorophenyl)-ethyl)-4-oxo-4,5,6,7-tetrahydro-cyclopentapyrimidin-1-yl)-N-(4'-trifluoromethyl-biphenyl-4-ylmethyl)¬ acetamide;

N-(2-diethylaminoethyl)-2-(2-(2-(3-fluorophenyl)-ethyl)-4-oxo-4,5,6,7-tetrahydro-cyclopentapyrimidin-1-yl)-N-(4'-trifluoromethyl-biphenyl-4-ylmethyl)¬ acetamide bitartrate;

N-(2-diethylaminoethyl)-2-(2-(2-(3-chlorophenyl)-ethyl)-4-oxo-4,5,6,7-tetrahydro-cyclopentapyrimidin-1-yl)-N-(4'-trifluoromethyl-biphenyl-4-ylmethyl)¬ acetamide;

N-(2-diethylaminoethyl)-2-(2-(2-(4-chlorophenyl)-ethyl)-4-oxo-4,5,6,7-tetrahydro-cyclopentapyrimidin-1-yl)-N-(4'-trifluoromethyl-biphenyl-4-ylmethyl)¬ acetamide;

N-(2-diethylaminoethyl)-2-(2-(2-(4-methylphenyl)-ethyl)-4-oxo-4,5,6,7-tetrahydro-cyclopentapyrimidin-1-yl)-N-(4'-trifluoromethyl-biphenyl-4-ylmethyl)¬ acetamide;

N-(2-diethylaminoethyl)-2-(2-(2-(4-(trifluoromethyl)phenyl)-ethyl)-4-oxo-4,5,6,7-tetrahydro-cyclopentapyrimidin-1-yl)-N-(4'-trifluoromethyl-biphenyl-4-ylmethyl)¬ acetamide;

N-(2-diethylaminoethyl)-2-(2-(2-(4-methoxyphenyl)-ethyl)-4-oxo-4,5,6,7-tetrahydro-cyclopentapyrimidin-1-yl)-N-(4'-trifluoromethyl-biphenyl-4-ylmethyl)¬ acetamide bitartrate;

N-(2-diethylaminoethyl)-2-(2-(2-(4-(trifluoromethoxy)phenyl)-ethyl)-4-oxo-4,5,6,7-tetrahydro-cyclopentapyrimidin-1-yl)-N-(4'-trifluoromethyl-biphenyl-4-ylmethyl)¬ acetamide bitartrate;

or the free base of any of the bitartrate salts, or another pharmaceutically acceptable salt.

Further, of interest are compounds of formula (III), disclosed in WO 02/30904:

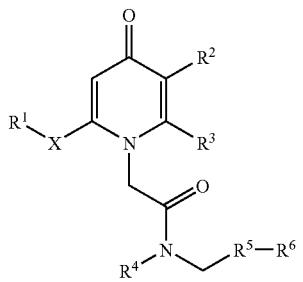

(III)

in which:

R1 is an aryl group, optionally substituted by 1, 2, 3 or 4 substituents which can be the same or different selected from C(1-6)alkyl, C(1-6)alkoxy, C(1-6)alkylthio, hydroxy, halogen, CN, mono to perfluoro-C(1 4)alkyl, mono to perfluoro-C(1 4)alkoxyaryl, and arylC(1 4)alkyl;

R2 is halogen, C(1 3)alkyl, C(1 3)alkoxy, hydroxyC(1 3)alkyl, C(1 3)alkylthio, C(1 3)alkylsulphinyl, aminoC(1-3) alkyl, mono- or di-C(1-3)alkylaminoC(1-3)alkyl, C(1 3)alkylcarbonylaminoC(1-3)alkyl, C(1 3)alkoxyC(1 3)alkylcarbonylaminoC(1-3)alkyl, C(1 3)alkylsulphonylaminoC(1-3) alkyl, C(1 3)alkylcarboxy, C(1 3)alkylcarboxyC(1 3)alkyl, and R3 is hydrogen, halogen, C(1-3)alkyl, or hydroxyC(1-3)alkyl; or R2 and R3 together with the pyridone ring carbon atoms to which they are attached form a fused 5- or 6-membered carbocyclic ring; or R2 and R3 together with the pyridone ring carbon atoms to which they are attached form a fused benzo or heteroaryl ring optionally substituted by 1, 2, 3 or 4 substituents which can be the same or different selected from halogen, C(1 4)alkyl, cyano, C(1-3)alkoxyC(1-3)alkyl, C(1 4)alkoxy or C(1 4)alkylthio, or mono to perfluoro-C(1-4)alkyl;

R4 is hydrogen, C(1-6)alkyl which can be unsubstituted or substituted by 1, 2 or 3 substituents selected from hydroxy, halogen, OR7, COR7, carboxy, COOR7, CONR9R10, NR9R10, NR7COR8, mono- or di(hydroxyC(1 6)alkyl)amino and N hydroxyC(1-6)alkyl-N C(1-6)alkylamino; or R4 is Het-C(0-4)alkyl in which Het is a 5- to 7-membered heterocyclyl ring comprising N and optionally O or S, and in which N can be substituted by COR7, COOR7, CONR9R10, or C(1 6)alkyl optionally substituted by 1, 2 or 3 substituents selected from hydroxy, halogen, OR7, COR7, carboxy, COOR7, CONR9R10 or NR9R10, for instance, piperidin-4-yl, pyrrolidin-3-yl;

R5 is an aryl or a heteroaryl ring optionally substituted by 1, 2, 3 or 4 substituents which can be the same or different selected from C(1-6)alkyl, C(1-6)alkoxy, C(1 6)alkylthio, arylC(1-6)alkoxy, hydroxy, halogen, CN, COR7, carboxy, COOR7, NR7COR8, CONR9R10, SO2NR9R10, NR7SO2R8, NR9R10, mono to perfluoro-C(1 4)alkyl and mono to perfluoro-C(1 4)alkoxy;

R6 is an aryl or a heteroaryl ring which is further optionally substituted by 1, 2, 3 or 4 substituents which can be the same or different selected from C(1-6)alkyl, C(1-6)alkoxy, C(1 6)alkylthio, C(1 6)alkylsulfonyl, arylC(1-6)alkoxy, hydroxy, halogen, CN, COR7, carboxy, COOR7, CONR9R10, NR7COR8, SO2NR9R10, NR7SO2R8, NR9R10, mono to perfluoro-C(1 4)alkyl and mono to perfluoro-C(1 4)alkoxy, or C(5-10)alkyl;

R7 and R8 are independently hydrogen or C(1-12)alkyl, for instance C(1-4)alkyl (e.g. methyl or ethyl);

R9 and R10 which can be the same or different is each selected from hydrogen, or C(1 12)alkyl, or R9 and R10 together with the nitrogen to which they are attached form a 5- to 7 membered ring optionally containing one or more further heteroatoms selected from oxygen, nitrogen and sulphur, and optionally substituted by one or two substituents selected from hydroxy, oxo, C(1-4)alkyl, C(1-4)alkylcarboxy, aryl, e.g. phenyl, or aralkyl, e.g benzyl, for instance morpholine or piperazine; and X is a C(2-4)alkylene group (optionally substituted by 1, 2 or 3 substituents selected from methyl and ethyl), CH=CH, (CH2)nS or (CH2)nO where n is 1, 2 or 3;

or a pharmaceutically acceptable salt thereof.

Of particular interest are those compounds of formula (III) where R2 and R3 together with the pyridone ring carbon atoms to which they are attached form a fused benzo or heteroaryl ring optionally substituted by 1, 2, 3 or 4 substituents which can be the same or different selected from halogen, C(1 4)alkyl, cyano, C(1 4)alkoxy or C(1 4)alkylthio, or mono to perfluoro-C(1-4)alkyl. Preferably, R1 is phenyl optionally substituted by halogen, C(1-6)alkyl, trifluoromethyl, C(1-6)alkoxy, preferably, from 1 to 3 fluoro, more preferably, 2,3- difluoro. Representative examples of R4 include piperidin-4-yl substituted at the 1-position by methyl, isopropyl, 1-(2-methoxyethyl), 1-(2-hydroxyethyl), t-butoxycarbonyl or ethoxycarbonylmethyl; ethyl substituted at the 2-position by aminoethyl; 1-ethylpiperidinylmethyl; piperidin-4-yl; 3-diethylaminopropyl; 4-pyrrolidin-1-ylbutyl and 1-ethylpyrrolidin-3-yl. Preferably R4 is 1-(2-methoxyethyl)piperidin-4-yl, 1-methylpiperidin-4-yl or 1-ethylpyrrolidin-3-yl. Representative examples of R5 include phenyl and pyridyl. Preferably, R5 is phenyl. Representative examples of R6 include phenyl optionally substituted by halogen, or trifluoromethyl, preferably at the 4-position and hexyl. Preferably, R6 is phenyl substituted by trifluoromethyl at the 4-position. Further representative examples of R6 include phenyl substituted by 1 or more C(1-3)alkyl. Preferably, R6 is phenyl substituted by ethyl in the 4-position. Preferably, R5 and R6 together form a 4-(phenyl)phenyl or a 2-(phenyl)pyridinyl substituent in which the remote phenyl ring can be optionally substituted by halogen or trifluoromethyl, preferably at the 4-position. Preferably X is C(2-4)alkylene, more preferably C(2-3)alkylene, most preferably, (CH2)2, or CH2S.

It will be appreciated that within the group of compounds comprising formula (III) there is sub-group of compounds in which:

R1 is phenyl substituted by 2,3-difluoro;
R2 and R3, together with the pyridone ring carbon atoms to which they are attached, form a fused benzo or pyrido ring;
R4 is 1-(2-methoxyethyl)piperidin-4-yl;
R5 and R6 together form a 4-(phenyl)phenyl substituent in which the remote phenyl ring is substituted by trifluoromethyl, preferably at the 4-position; and
X is CH2S or (CH2)2.

The following compounds of formula (III) are of interest:
N-(2-diethylaminoethyl)-2-[2-(2,3-difluorobenzylthio)-4-oxo-4H-quinolin-1-yl]-N-(4'-trifluoromethylbiphenyl-4-ylmethyl)¬ acetamide bitartrate;
N-(2-diethylaminoethyl)-2-[2-(2-(2,3-difluorophenyl)ethyl)-4-oxo-4H-quinolin-1-yl]-N-(4'-trifluoromethylbiphenyl-4-ylmethyl)¬ acetamide;
N-(2-diethylaminoethyl)-2-[2-(2-(2,3-difluorophenyl)ethyl)-4-oxo-4H-quinolin-1-yl]-N-(4'-trifluoromethylbiphenyl-4-ylmethyl)¬ acetamide bitartrate;
N-(2-diethylaminoethyl)-2-[2-(2,3-difluorobenzylthio)-4-oxo-5,6-trimethylene¬ pyridin-1-yl]-N-(4'-trifluoromethylbiphenyl-4-ylmethyl)¬ acetamide bitartrate;
N-(1-(2-methoxyethyl)piperidin-4-yl)-2-[2-(2,3-difluorobenzylthio)-4-oxo-4H-quinolin-1-yl]-N-(4'-trifluoromethylbiphenyl-4-ylmethyl)¬ acetamide;
N-(1-methylpiperidin-4-yl)-2-[2-(2,3-difluorobenzylthio)-4-oxo-4H-quinolin-1-yl]-N-(4'-trifluoromethylbiphenyl-4-ylmethyl)¬ acetamide bitartrate;
N-(1-methylpiperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)¬ acetamide bitartrate;
N-(1-(2-methoxyethyl)piperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)¬ acetamide;
N-(1-(2-methoxyethyl)piperidin-4-yl)-2-[2-(2,3-difluorobenzylthio)-4-oxo-4H-[1,8]naphthyridin-1-yl]-N-(4'-trifluoromethylbiphenyl-4-ylmethyl)¬ acetamide bitartrate;
N-(1-ethylpiperidin-4-yl)-2-[2-(2,3-difluorobenzylthio)-4-oxo-4H-quinolin-1-yl]-N-(4'-ethylbiphenyl-4-ylmethyl)¬ acetamide bitartrate;
N-(1-ethylpiperidin-4-yl)-2-[5-(2-(2,3-difluorophenyl)ethyl)-2-methyl-7-oxo-7H-thiazolo[4,5-b]pyridin-4-yl]-N-(4'-trifluoromethylbiphenyl-4-ylmethyl)¬ acetamide bitartrate;
(±)¬ N-(1-ethylpyrrolidin-3-yl)-2-[2-(2-(2,3-difluorophenyl)ethyl)-4-oxo-4H-quinolin-1-yl]-N-(4'-trifluoromethylbiphenyl-4-ylmethyl)¬ acetamide bitartrate;
(±)¬ N-(1-ethylpyrrolidin-3-yl)-2-[2-(2,3-difluorobenzylthio)-4-oxo-4H-quinolin-1-yl]-N-(4'-trifluoromethylbiphenyl-4-ylmethyl)¬ acetamide bitartrate;
N-(1-(2-methoxyethyl)piperidin-4-yl)-2-[2-(2,3-difluorobenzylthio)-4-oxo-4H-quinolin-1-yl]-N-(4'-trifluoromethylbiphenyl-4-ylmethyl)¬ acetamide bitartrate;
N-(1-(2-methoxyethyl)piperidin-4-yl)-2-[2-(2,3-difluorobenzylthio)-4-oxo-4H-quinolin-1-yl]-N-(4'-trifluoromethylbiphenyl-4-ylmethyl)¬ acetamide dihydrochloride;
N-(1-(2-methoxyethyl)piperidin-4-yl)-2-[2-(2,3-difluorobenzylthio)-4-oxo-4H-quinolin-1-yl]-N-(4'-trifluoromethylbiphenyl-4-ylmethyl)¬ acetamide mono paratoluenesulphonate;
N-(1-(2-methoxyethyl)piperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)¬ acetamide bitartrate;
N-(1-(2-methoxyethyl)piperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)¬ acetamide monohydrochloride;
N-(1-(2-methoxyethyl)piperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)¬ acetamide dihydrochloride;
N-(2-diethylaminoethyl)-2-[2-(4-fluorobenzylthio)-4-oxo-4H-quinolin-1-yl]-N-(4'-trifluoro¬ methylbiphenyl-4-ylmethyl)¬ acetamide bitartrate;
N-(2-diethylaminoethyl)-2-[2-(4-fluorobenzylthio)-4-oxo-5,6-trimethylene¬ pyridin-1-yl]-N-(4'-trifluoromethyl-biphenyl-4-ylmethyl)¬ acetamide bitartrate;
N-(2-diethylaminoethyl)-2-[2-(2,3-difluorobenzylthio)-4-oxo-5,6-trimethylene¬ pyridin-1-yl]-N-(4'-trifluoromethyl-biphenyl-4-ylmethyl)¬ acetamide bitartrate;
N-(2-diethylaminoethyl)-2-[2-(4-fluorophenyl)ethyl)-4-oxo-4H-quinolin-1-yl]-N-(4'-trifluoro¬ methylbiphenyl-4-ylmethyl)¬ acetamide;
N-(2-diethylaminoethyl)-2-[2-(2-(3,4-difluorophenyl)ethyl)-4-oxo-4H-quinolin-1-yl]-N-(4'-trifluoro¬ methylbiphenyl-4-ylmethyl)¬ acetamide bitartrate;
N-(2-diethylaminoethyl)-2-[2-(2-(2-fluorophenyl)ethyl)-4-oxo-4H-quinolin-1-yl]-N-(4'-trifluoro¬ methylbiphenyl-4-ylmethyl)¬ acetamide bitartrate;
N-(2-diethylaminoethyl)-2-[2-(2-(3-chlorophenyl)ethyl)-4-oxo-4H-quinolin-1-yl]-N-(4'-trifluoro¬ methylbiphenyl-4-ylmethyl)¬ acetamide bitartrate;
N-(2-diethylaminoethyl)-2-[2-(2-(2,3-difluorophenyl)ethyl)-4-oxo-4H-[1,8]naphthyridin-1-yl)]-N-(4'-trifluoromethylbiphenyl-4-ylmethyl)¬ acetamide bitartrate;
N-(1-ethylpiperidin-4-yl)-2-[2-(2-(2,3-difluorophenyl)ethyl)-4-oxo-4H-[1,8]naphthyridin-1-yl)]-N-(4'-trifluoromethylbiphenyl-4-ylmethyl)¬ acetamide;
N-(1-ethylpiperidin-4-yl)-2-[2-(2-(2,3-difluorophenyl)ethyl)-4-oxo-4H-quinolin-1-yl]-N-(4'-trifluoro¬ methyl-biphenyl-4-ylmethyl)¬ acetamide bitartrate;
N-(2-pyrrolidin-1-ylethyl)-2-[2-(2-(2,3-difluorophenyl)ethyl)-4-oxo-4H-quinolin-1-yl]-N-(4'-trifluoro¬ methyl-biphenyl-4-ylmethyl)¬ acetamide bitartrate;

N-(1-isopropylpiperidin-4-yl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(2-piperidin-1-ylethyl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(2-diethylaminoethyl)-2-[2-(2,3-difluorobenzylthio)-7-fluoro-4-oxo-4H-quinolin-1-yl]-N-(4'-trifluoromethylbiphenyl-4-ylmethyl)acetamide bitartrate;

N-(2-diethylaminoethyl)-5-[2-(2-(2,3-difluorophenyl)ethyl)-2-methyl-7-oxo-7H-thieno[3,2-b]pyridin-4-yl]-N-(4'-trifluoromethylbiphenyl-4-ylmethyl)acetamide bitartrate;

N-(2-diethylaminoethyl)-2-[2-(2-(2,3-difluorophenyl)ethyl)-5,6-dimethyl-4-oxo-4H-pyridin-1-yl]-N-(4'-trifluoromethylbiphenyl-4-ylmethyl)acetamide bitartrate;

N-(2-diethylaminoethyl)-2-[2-(2-(2,3-difluorophenyl)ethyl)-5-ethyl-4-oxo-4H-pyridin-1-yl]-N-(4'-trifluoromethylbiphenyl-4-ylmethyl)acetamide bitartrate;

N-(1-(2-methoxyethyl)piperidin-4-yl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(1-methylpiperidin-4-yl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(2-diethylaminoethyl)-2-[2-(2-(2,3-difluorophenyl)ethyl)-4-oxo-4H-thieno[3,4-b]pyridin-1-yl]-N-(4'-trifluoromethylbiphenyl-4-ylmethyl)acetamide bitartrate;

N-(1-ethylpiperidin-4-yl)-2-[2-(2,3-difluorobenzylthio)-4-oxo-4H-quinolin-1-yl]-N-(4'-trifluoromethylbiphenyl-4-ylmethyl)acetamide bitartrate;

N-(2-pyrrolidin-1-ylethyl)-2-[2-(2,3-difluorobenzylthio)-4-oxo-4H-quinolin-1-yl]-N-(4'-trifluoromethylbiphenyl-4-ylmethyl)acetamide bitartrate;

N-(1-ethylpiperidin-4-yl)-2-[6-(2-(2,3-difluorophenyl)ethyl)-2-methyl-4-oxo-4H-pyrazolo[3,4-b]pyridin-7-yl]-N-(4'-trifluoromethylbiphenyl-4-ylmethyl)acetamide bitartrate;

N-(1-isopropylpiperidin-4-yl)-2-[2-(2,3-difluorobenzylthio)-4-oxo-4H-quinolin-1-yl]-N-(4'-trifluoromethylbiphenyl-4-ylmethyl)acetamide bitartrate;

N-(1-ethylpiperidin-4-ylmethyl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(3-diethylaminopropyl)-2-[2-(2,3-difluorobenzylthio)-4-oxo-4H-quinolin-1-yl]-N-(4'-trifluoromethylbiphenyl-4-ylmethyl)acetamide bitartrate;

N-(4-pyrrolidin-1-ylbutyl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(3-diethylaminopropyl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(4-pyrrolidin-1-ylbutyl)-2-[2-(2,3-difluorobenzylthio)-4-oxo-4H-quinolin-1-yl]-N-(4'-trifluoromethylbiphenyl-4-ylmethyl)acetamide bitartrate;

N-(1-ethylpiperidin-4-yl)-2-[5-(2-(2,3-difluorobenzylthio)-7-oxo-7H-thieno[3,2-b]pyridin-4-yl]-N-(4'-trifluoromethylbiphenyl-4-ylmethyl)acetamide bitartrate;

N-(2-diethylaminoethyl)-2-[5-(2-(2,3-difluorophenyl)ethyl)-2-methyl-7-oxo-7H-thiazolo[4,5-b]pyridin-4-yl]-N-(4'-trifluoromethylbiphenyl-4-ylmethyl)acetamide bitartrate;

N-(2-diethylaminoethyl)-2-[2-(2,3-difluorobenzylthio)-4-oxo-4H-quinolin-1-yl]-N-(4'-ethylbiphenyl-4-ylmethyl)acetamide bitartrate;

N-(2-diethylaminoethyl)-2-[2-(2-(2,3-difluorophenyl)ethyl)-4-oxo-4H-quinolin-1-yl]-N-(4'-ethylbiphenyl-4-ylmethyl)acetamide bitartrate;

N-(2-diethylaminoethyl)-2-[2-(2,3-difluorobenzylthio)-4-oxo-4H-quinolin-1-yl]-N-(4'-isopropylbiphenyl-4-ylmethyl)acetamide bitartrate;

N-(2-diethylaminoethyl)-2-[2-(2-(2,3-difluorophenyl)ethyl)-4-oxo-4H-quinolin-1-yl]-N-(4'-isopropylbiphenyl-4-ylmethyl)acetamide bitartrate;

N-(2-diethylaminoethyl)-2-[2-(2,3-difluorobenzylthio)-4-oxo-4H-[1,8]naphthyridin-1-yl]-N-(4'-trifluoromethylbiphenyl-4-ylmethyl)acetamide bitartrate;

N-(1-ethylpiperidin-4-yl)-2-[2-(2,3-difluorobenzylthio)-4-oxo-4H-[1,8]naphthyridin-1-yl]-N-(4'-trifluoromethylbiphenyl-4-ylmethyl)acetamide bitartrate;

N-(2-diethylaminoethyl)-2-[2-(2-(2,3-difluorophenyl)ethyl)-4-oxo-4H-quinolin-1-yl]-N-(4'-methylbiphenyl-4-ylmethyl)acetamide bitartrate;

N-(2-diethylaminoethyl)-2-[2-(2,3-difluorobenzylthio)-4-oxo-4H-quinolin-1-yl]-N-(4'-methylbiphenyl-4-ylmethyl)acetamide bitartrate;

N-(1-ethoxycarbonylmethylpiperidin-4-yl)-2-[2-(2-(2,3-difluorophenyl)ethyl)-4-oxo-4H-quinolin-1-yl]-N-(4'-trifluoromethylbiphenyl-4-ylmethyl)acetamide bitartrate;

N-(1-isopropylpiperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)acetamide bitartrate;

N-(2-diethylaminoethyl)-2-[2-(2,3-difluorobenzylthio)-4-oxo-4H-quinolin-1-yl]-N-(3',4'-dimethylbiphenyl-4-ylmethyl)acetamide bitartrate;

N-(1-(t-butoxycarbonyl)piperidin-4-yl)-2-[2-(2-(2,3-difluorophenyl)ethyl)-4-oxo-4H-[1,8]naphthyridin-1-yl]-N-(4'-trifluoromethylbiphenyl-4-ylmethyl)acetamide bitartrate;

N-(2-diethylaminoethyl)-2-[2-(2,3-difluorobenzylthio)-4-oxo-4H-quinolin-1-yl]-N-(3',4'-difluorobiphenyl-4-ylmethyl)acetamide bitartrate;

N-(2-diethylaminoethyl)-2-[6-(2,3-difluorobenzylthio)-4-oxo-4H-thieno[2,3b]pyridin-7-yl]-N-(4'-trifluoromethylbiphenyl-4-ylmethyl)acetamide bitartrate;

N-(1-methylpiperidin-4-yl)-2-[2-(2,3-difluorobenzylthio)-4-oxo-4H-[1,8]naphthyridin-1-yl]-N-(4'-trifluoromethylbiphenyl-4-ylmethyl)acetamide bitartrate;

N-(1-ethylpiperidin-4-yl)-2-[2-(2-(2,3,4-trifluorophenyl)ethyl)-4-oxo-4H-quinolin-1-yl]-N-(4'-trifluoromethylbiphenyl-4-ylmethyl)acetamide bitartrate;

N-(2-diethylaminoethyl)-2-[6-(2,3-difluorobenzylthio)-2-methyl-4-oxo-2,4-dihydropyrazolo[3,4b]pyridin-7-yl]-N-(4'-trifluoromethylbiphenyl-4-ylmethyl)acetamide bitartrate;

N-(1-ethylpiperidin-4-yl)-2-[6-(2-(2,3-difluorophenyl)ethyl)-2-ethyl-4-oxo-2,4-dihydropyrazolo[3,4b]pyridin-7-yl]-N-(4'-trifluoromethylbiphenyl-4-ylmethyl)acetamide bitartrate;

N-(1-ethylpiperidin-4-yl)-2-[6-(2-(2,3-difluorophenyl)ethyl)-2-isopropyl-4-oxo-2,4-dihydropyrazolo[3,4b]pyridin-7-yl]-N-(4'-trifluoro methylbiphenyl-4-yl-methyl) acetamide bitartrate;

N-(1-ethylpiperidin-4-yl)-2-[2-(2-(2,3-difluorophenyl)ethyl)-4-oxo-4H-quinolin-1-yl]-N-(4'-ethyl biphenyl-4-ylmethyl) acetamide bitartrate;

N-(1-isopropylpiperidin-4-yl)-2-[5-(2-(2,3-difluorophenyl)ethyl)-2-methyl-7-oxo-7H-thiazolo[4,5-b]pyridin-4-yl]-N-(4'-trifluoro methylbiphenyl-4-yl methyl) acetamide bitartrate;

N-(1-(2-methoxyethyl)piperidin-4-yl)-2-[5-(2-(2,3-difluorophenyl)ethyl)-2-methyl-7-oxo-7H-thiazolo[4,5-b] pyridin-4-yl]-N-(4'-trifluoro methyl biphenyl-4-yl-methyl) acetamide bitartrate;

N-(1-ethylpiperidin-4-yl)-2-[2-(2-(2,3-difluorophenyl)ethyl)-4-oxo-5,6-trimethylene pyridin-1-yl]-N-(4'-trifluoro methylbiphenyl-4-ylmethyl) acetamide bitartrate;

N-(1-methylpiperidin-4-yl)-2-[2-(2-(2,3-difluorophenyl)ethyl)-4-oxo-5,6-trimethylene pyridin-1-yl]-N-(4'-trifluoro methylbiphenyl-4-ylmethyl) acetamide bitartrate;

N-(1-(2-methoxyethyl)piperidin-4-yl)-2-[2-(2-(2,3-difluorophenyl)ethyl)-4-oxo-5,6-trimethylene pyridin-1-yl]-N-(4'-trifluoro methylbiphenyl-4-ylmethyl) acetamide bitartrate;

N-(1-isopropylpiperidin-4-yl)-2-[2-(2-(2,3-difluorophenyl)ethyl)-4-oxo-5,6-trimethylene pyridin-1-yl]-N-(4'-trifluoro methylbiphenyl-4-ylmethyl) acetamide bitartrate;

N-(1-ethylpiperidin-4-yl)-2-[5-(2-(2,3-difluorophenyl)ethyl)-2-methyl-7-oxo-2,7-dihydropyrazolo[4,3b]pyridin-4-yl]-N-(4'-trifluoro methylbiphenyl-4-yl-methyl) acetamide bitartrate;

N-(1-ethylpiperidin-4-yl)-2-[5-(2-(2,3-difluorophenyl)ethyl)-1-methyl-7-oxo-1,7-dihydropyrazolo[4,3b]pyridin-4-yl]-N-(4'-trifluoro methylbiphenyl-4-yl-methyl) acetamide bitartrate;

N-(1-ethylpiperidin-4-yl)-2-[2-(2-(2,3-difluorophenyl)ethyl)-4-oxo-5,6-trimethylene pyridin-1-yl]-N-(4'-trifluoro methylbiphenyl-4-ylmethyl) acetamide bitartrate;

N-(1-ethylpiperidin-4-yl)-2-[2-(2-(2,3-difluorophenyl)ethyl)-7-methyl-4-oxo-4H-[1,8]naphthyridin-1-yl]-N-(4'-trifluoro methylbiphenyl-4-ylmethyl) acetamide bitartrate;

N-(2-diethylaminoethyl)-2-[2-(2-(2,3-difluorophenyl)ethyl)-7-methyl-4-oxo-4H-[1,8]naphthyridin-1-yl]-N-(4'-trifluoro methylbiphenyl-4-ylmethyl) acetamide bitartrate;

N-(1-methylpiperidin-4-yl)-2-[2-(2-(2,3-difluorophenyl)ethyl)-7-methyl-4-oxo-4H-[1,8]naphthyridin-1-yl]-N-(4'-trifluoro methylbiphenyl-4-ylmethyl) acetamide bitartrate;

N-(1-isopropylpiperidin-4-yl)-2-[2-(2-(2,3-difluorophenyl)ethyl)-7-methyl-4-oxo-4H-[1,8]naphthyridin-1-yl]-N-(4'-trifluoro methylbiphenyl-4-ylmethyl) acetamide bitartrate;

N-(1-(2-methoxyethyl)piperidin-4-yl)-2-[2-(2-(2,3-difluorophenyl)ethyl)-7-methyl-4-oxo-4H-[1,8]naphthyridin-1-yl]-N-(4'-trifluoro methylbiphenyl-4-ylmethyl) acetamide bitartrate;

N-(1-methylpiperidin-4-yl)-2-[2-(2,3-difluorobenzylthio)-4-oxo-5,6-trimethylene pyridin-1-yl]-N-(4'-trifluoro methyl biphenyl-4-ylmethyl) acetamide bitartrate;

N-(1-ethylpiperidin-4-yl)-2-[2-(2,3-difluorobenzylthio)-4-oxo-5,6-trimethylene pyridin-1-yl]-N-(4'-trifluoro methylbiphenyl-4-ylmethyl) acetamide bitartrate;

N-(1-isopropylpiperidin-4-yl)-2-[2-(2,3-difluorobenzylthio)-4-oxo-5,6-trimethylene pyridin-1-yl]-N-(4'-trifluoro methyl biphenyl-4-ylmethyl) acetamide bitartrate;

N-(1-(2-methoxyethyl)piperidin-4-yl)-2-[2-(2,3-difluorobenzylthio)-4-oxo-5,6-trimethylene pyridin-1-yl]-N-(4'-trifluoro methylbiphenyl-4-ylmethyl) acetamide bitartrate;

N-(2-diethylaminoethyl)-2-[2-(2-(2,3-difluorophenyl)ethyl)-4-oxo-5,6-tetramethylene pyridin-1-yl]-N-(4'-trifluoro methylbiphenyl-4-ylmethyl) acetamide bitartrate;

N-(1-methylpiperidin-4-yl)-2-[2-(2,3-difluorobenzylthio)-4-oxo-4H-quinolin-1-yl]-N-(4'-chlorobiphenyl-4-ylmethyl) acetamide bitartrate;

N-(1-methylpiperidin-4-yl)-2-[2-(2-(2,3-difluorophenyl)ethyl)-4-oxo-4H-quinolin-1-yl]-N-(4'-chlorobiphenyl-4-ylmethyl) acetamide bitartrate;

N-(1-ethylpiperidin-4-yl)-2-[2-(2-(2,3-difluorophenyl)ethyl)-4-oxo-4H-quinolin-1-yl]-N-(4'-chlorobiphenyl-4-ylmethyl) acetamide bitartrate;

N-(1-(2-methoxyethyl)piperidin-4-yl)-2-[2-(2-(2,3-difluorophenyl)ethyl)-4-oxo-4H-quinolin-1-yl]-N-(4'-chlorobiphenyl-4-ylmethyl) acetamide bitartrate;

N-(1-isopropylpiperidin-4-yl)-2-[2-(2-(2,3-difluorophenyl)ethyl)-4-oxo-4H-quinolin-1-yl]-N-(4'-chlorobiphenyl-4-ylmethyl) acetamide bitartrate;

N-(2-diethylaminoethyl)-2-[6-(2-(2,3-difluorophenyl)ethyl)-2-methyl-4-oxo-4H-pyrazolo [3,4-b]pyridin-7-yl]-N-(4'-trifluoro methylbiphenyl-4-ylmethyl) acetamide bitartrate;

N-(1-(t-butoxycarbonyl)piperidin-4-yl)-2-[2-(2,3-difluorobenzylthio)-4-oxo-4H-[1,8]naphthyridin-1-yl]-N-(4'-trifluoro methylbiphenyl-4-ylmethyl) acetamide;

N-(1-ethylpiperidin-4-yl)-2-[6-(2-(2,3-difluorophenyl)ethyl)-2-(2-methoxyethyl)-4-oxo-4H-pyrazolo [3,4-b]pyridin-7-yl]-N-(4'-trifluoro methylbiphenyl-4-ylmethyl) acetamide bitartrate;

N-(2-diethylaminoethyl)-2-[4-oxo-2-(2-(2,3,4-trifluorophenyl)ethyl)-4H-quinolin-1-yl]-N-(4'-trifluoromethyl-biphenyl-4-ylmethyl) acetamide bitartrate;

N-(2-diethylaminoethyl)-2-[2-(2-(2,4-difluoro phenyl)ethyl)-4-oxo-4H-quinolin-1-yl]-N-(4'-trifluoro methyl-biphenyl-4-yl methyl) acetamide bitartrate;

N-(2-diethylaminoethyl)-2-[2-(2-(3-fluoro phenyl)ethyl)-4-oxo-4H-quinolin-1-yl]-N-(4'-trifluoro methylbiphenyl-4-ylmethyl) acetamide bitartrate;

N-(piperidin-4-yl)-2-[2-(2,3-difluorobenzylthio)-4-oxo-4H-quinolin-1-yl]-N-(4'-trifluoro methylbiphenyl-4-ylmethyl) acetamide bitartrate;

N-(piperidin-4-yl)-2-[2-(2-(2,3-difluorophenyl)ethyl)-4-oxo-4H-quinolin-1-yl]-N-(4'-trifluoro methylbiphenyl-4-ylmethyl) acetamide bitartrate;

N-(piperidin-4-yl)-2-[2-(2-(2,3-difluorophenyl)ethyl)-4-oxo-5,6-trimethylene pyridin-1-yl]-N-(4'-trifluoro methylbiphenyl-4-ylmethyl) acetamide bitartrate;

N-(piperidin-4-yl)-2-[2-(2-(2,3-difluorophenyl)ethyl)-4-oxo-4H-[1,8]naphthyridin-1-yl]-N-(4'-trifluoro methyl-biphenyl-4-yl methyl) acetamide bitartrate;

N-(piperidin-4-yl)-2-[2-(2,3-difluorobenzylthio)-4-oxo-4H-[1,8]naphthyridin-1-yl]-N-(4'-trifluoro methylbiphenyl-4-yl methyl) acetamide trifluoroacetate;

N-(2-ethylaminoethyl)-2-[2-(2,3-difluorobenzylthio)-4-oxo-4H-quinolin-1-yl]-N-(4'-trifluoro¬ methylbiphenyl-4-ylmethyl)¬ acetamide;

N-(2-ethylaminoethyl)-2-[2-(2-(2,3-difluorophenyl)ethyl)-4-oxo-4H-quinolin-1-yl]-N-(4'-trifluoro¬ methylbiphenyl-4-ylmethyl)¬ acetamide;

N-(1-(2-hydroxyethyl)piperidin-4-yl)-2-[2-(2-(2,3-difluorophenyl)ethyl)-4-oxo-4H-quinolin-1-yl]-N-(4'-trifluoro¬ methylbiphenyl-4-ylmethyl)¬ acetamide bitartrate; or the free base thereof, or another pharmaceutically acceptable salt.

Formula (IV)

Also of interest are compounds of formula (IV)

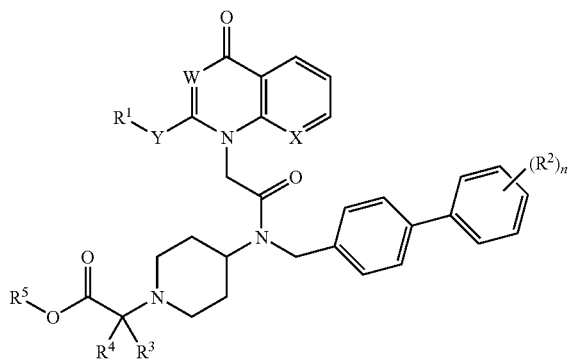

(IV)

wherein:

R1 is an aryl group, unsubstituted or substituted by 1, 2, 3 or 4 substituents which can be the same or different selected from the group consisting of C1-C6 alkyl, C1-C6 alkoxy, C1-C6 alkylthio, aryl C1-C6 alkoxy, hydroxy, halo, CN, COR6, COOR6, NR6COR7, CONR8R9, SO2NR8R9, NR6SO2R7, NR8R9, halo C1-C4 alkyl, and halo C1-C4 alkoxy;

W is CH and X is N, or W is N and X is CH, W and X are both CH, or W and X are N;

Y is C2-C4alkyl,

[291] R2 is hydrogen, C1-C6 alkyl, C1-C6 alkoxy, C1-C6 alkylthio, aryl C1-C6 alkoxy, hydroxy, halo, CN, COR6, carboxy, COOR6, NR6COR7, CONR8R9, SO2NR8R9, NR6SO2R7, NR8R9, mono to perfluoro-C1-C6 alkyl, or mono to perfluoro-C1-C6 alkoxy;

n is 0-5;

R3 is C1-C4 alkyl;

R4 is C1-C4 alkyl;

R5 is hydrogen, C1-C10 alkyl, C2-C10 alkenyl, C2-C10 alkynyl, halo C1-C4 alkyl, C3-C8 cycloalkyl, C3-C8 cycloalkyl, C3-C8 cycloalkyl C1-C4 alkyl, C5-C8cycloalkenyl, C5-C8cycloalkenyl C1-C4 alkyl, 3-8-membered heterocycloalkyl, 3-8-membered heterocycloalkyl C1-C4 alkyl, C6-C14 aryl, C6-C14 aryl C1-C10 alkyl, heteroaryl, or heteroaryl C1-C10alkyl; wherein each group is optionally one or more times by the same and/or a different group which is C1-C6 alkoxy, C1-C6 alkylthio, aryl C1-C6 alkoxy, hydroxy, halo, CN, NR8R9, or halo C1-C4 alkoxy R6 and R7 are independently hydrogen or C1-C10 alkyl;

R8 and R9 are the same or different and are hydrogen or C1-C10 alkyl, or R9 and R10 together with the nitrogen to which they are attached form a 5- to 7 membered ring optionally containing one or more further heteroatoms selected from oxygen, nitrogen and sulphur, and optionally substituted by one or two substituents selected from the group consisting of hydroxy, oxo, C1-C4 alkyl, C1-C4 alkylcarboxy, aryl, and aryl C1-C4 alkyl;

or a pharmaceutically acceptable salt thereof.

Without intending to exclude any defined substituents and/or their recited radicals from the scope of formula (IV), the following R groups and the associated radicals are of particular interest:

As regards R1, it can be an phenyl group optionally substituted by 1, 2, 3 or 4 substituents which can be the same or different selected from halo, C1-C6 alkyl, trifluoromethyl or C1-C6 alkoxy. More specifically, phenyl is unsubstituted or substituted by 1, 2, 3 or 4 halogen substituents, particularly, from 1 to 3 fluoro groups, and most particularly, 2,3-difluoro, 2,4-difluoro or 4-fluoro.

A further embodiment of formula (I) is where Y is —CH2CH2-.

The invention also provides a compound of formula (I) in which R2 is hydrogen, by default, or is halo, C1-C6 alkyl, mono to perfluoro-C1-C4 alkyl, mono to perfluoro C1-C46 alkoxy, or C1-C6 alkoxy; particularly mono to perfluoro-C1-C4 alkyl, mono to perfluoro-C1-C4 alkoxy, or C1-C6 alkoxy. Of particular interest are the compounds where R2 is other than hydrogen, n in (R2)n is 1, 2, or 3, and the substitution pattern is meta and/or para, particularly para, i.e. a 4-position substituent. Exemplified compounds include those where R2 is 4-trifluoromethyl or 4-trifluoromethoxy.

R3 and R4 can be the same or different and are methyl, ethyl, n-propyl, or n-butyl. Of particular interest are those compounds of formula (I) where R3 and R4 are the same and are methyl, or ethyl; methyl is of particular interest.

R5 can be hydrogen, C(1-6) alkyl which is a straight chain, or branched. Of particular interest is methyl, ethyl, propyl, isopropyl, n-butyl, sec-butyl, iso-butyl, t-butyl, n-pentyl or n-hexyl.

Any of the compounds described herein above can be prepared in crystalline or non crystalline form, and, if crystalline, can be solvated, e.g. as the hydrate. This invention includes within its scope stoichiometric solvates (e.g. hydrates).

Certain of the compounds described herein can contain one or more chiral atoms, or can otherwise be capable of existing as two enantiomers. The compounds useful in the methods as described herein include mixtures of enantiomers as well as purified enantiomers or enantiomerically enriched mixtures. Also included within the scope of the invention are the individual isomers of the compounds represented by formulas (I)-(IV), as well as any wholly or partially equilibrated mixtures thereof. The present invention also covers the individual isomers of the claimed compounds as mixtures with isomers thereof in which one or more chiral centers are inverted. Also, it is understood that any tautomers and mixtures of tautomers of the claimed compounds are included within the scope of the compounds of formulas (I)-(IV). The different isomeric forms can be separated or resolved one from the other by conventional methods, or any given isomer can be obtained by conventional synthetic methods or by stereospecific or asymmetric syntheses.

Syntheses of the Compounds of Formula (I), (II), (III) and (IV)

Methods for preparing compounds of formula (I), (II) and (III) have been published in the patent literature. For example, methods for making formula (I) can be found in WO 01/60805 and WO03/016287. Methods for making compounds of formula (II) have been set out in WO 02/30911.

And methods for making compounds of formula (III) can be found in WO 02/30904. This document provides methods for making compounds of formula (IV), methods copied from U.S. provisional applications 60/829,328 and 60/829,327, which are specifically incorporated herein by reference.

Some examples of syntheses are provided below. To differentiate between the several generic groups of compounds in the examples herein, materials relating to formula (I) will be labeled as "Example of Synthesis Approach (I)-1" et seq., for formula (II) "Example of Synthesis Approach (II)-1" et seq., for formula (III), "Example of Synthesis Approach (III)-1 et seq., and for formula (I), "Example of Synthesis Approach (IV)-1, et seq.

Synthesis of Formula (I)

Compounds of formulae (I) can be prepared by processes scheme I, as disclosed in WO 01/60805:

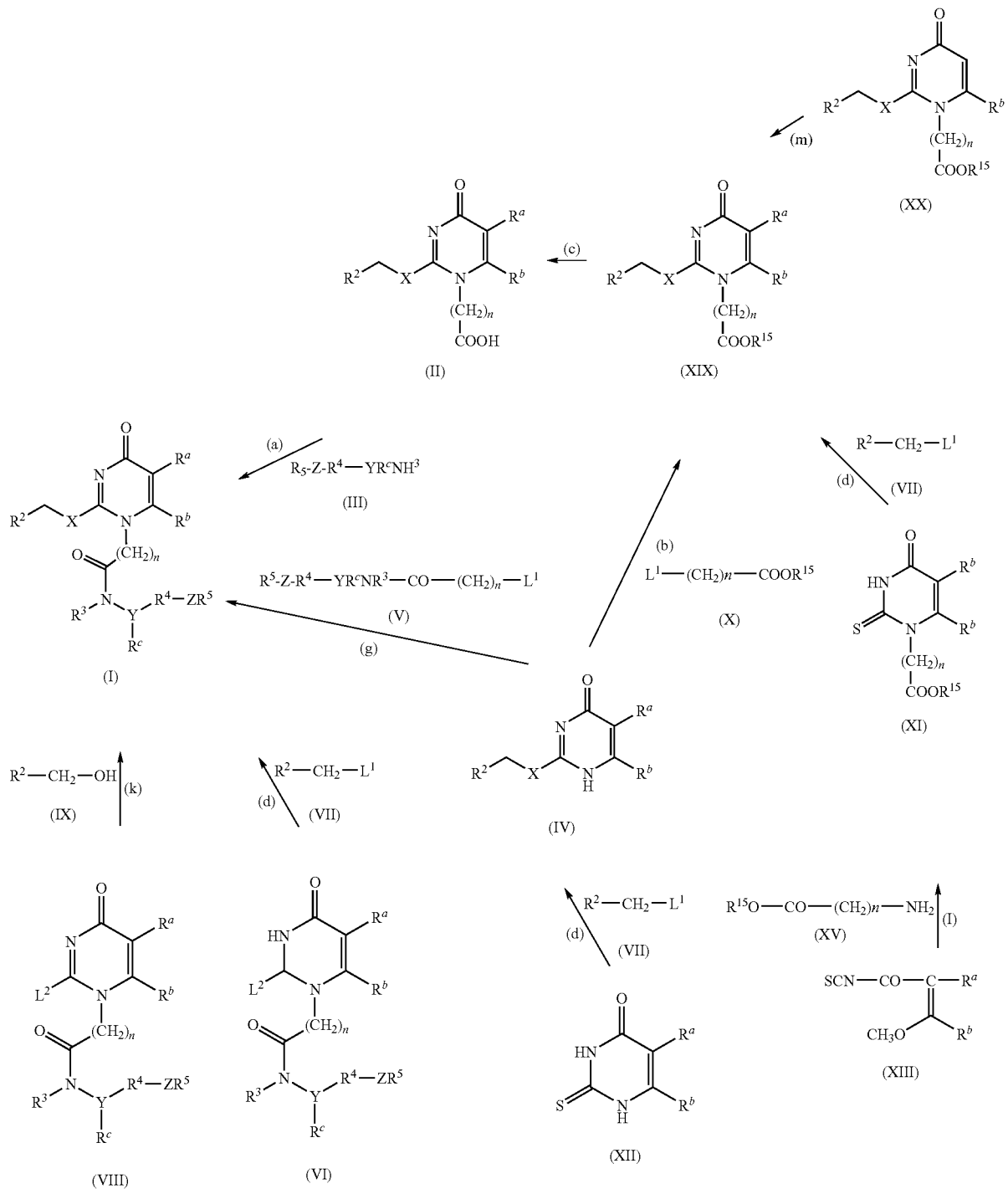

-continued

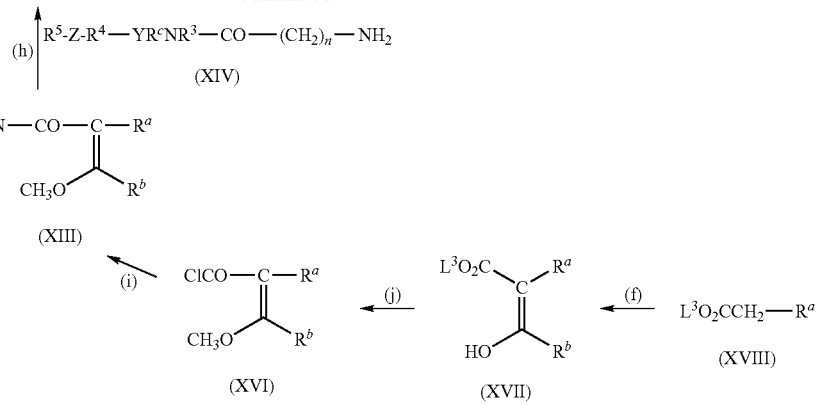

in which:
L³ is a C(1-6)alkyl group, for instance methyl;
R¹⁵ is a $C_{(1-6)}$alkyl group, for instance ethyl or t-butyl and L¹, L², $R^a$, $R^b$, $R^c$, R², R³, R⁴, R⁵, n, X, Y and Z are as defined in WO 01/60805.

An exemplary reaction for making a compound of formula (I) of interest is as follows:

Example of Synthesis Approach (I)-1(a)

1-(N-(2-(Diethylamino)ethyl)-N-(4-(4-trifluoromethylphenyl)benzyl)aminocarbonylmethyl)-2-(4-fluorobenzyl)thio-5,6-trimethylenepyrimidin-4-one

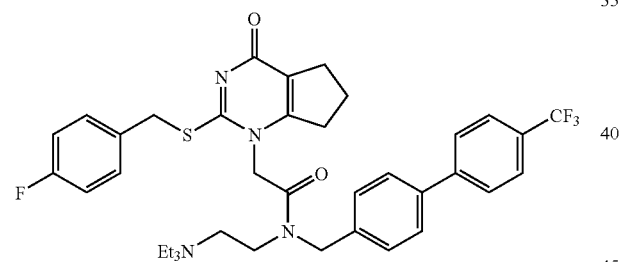

Intermediate B69 of WO 01/60805 (87.1 g, 0.26 mol.) was suspended in dichloromethane (2.9 liter). 1-Hydroxybenzotriazole hydrate (35.2 g, 0.26 mol.) and 1-(3-dimethylaminopropyl)-3-ethylcarbodiimide hydrochloride (99.7 g, 0.52 mol.) were added and the suspension stirred for 45 minutes by which time complete solution had been obtained. Intermediate A30 of WO 01/60805 (91.2 g, 0.26 mol.) was added as a solution in dichloromethane (100 ml) over 5 minutes and the solution stirred for 4 hours. Saturated ammonium chloride solution:water mixture (1:1, 1 liter) was added and the solution stirred for 10 minutes. The organic phase was separated and extracted with saturated ammonium chloride:water mixture (1:1, 1 liter), extracts were pH 6. The organic phase was separated and extracted with water (1 liter) containing acetic acid (10 ml), extract pH 5. The dichloromethane layer was separated and extracted with saturated sodium carbonate solution:water:saturated brine mixture (1:3:0.2, 1 liter), pH 10.5, then with saturated brine:water:mixture (1:1, 1 liter). The brown solution was dried over anhydrous sodium sulfate in the presence of decolourising charcoal (35 g), filtered and the solvent removed in vacuo to give a dark brown foam. The foam was dissolved in iso-propyl acetate (100 ml) and the solvent removed in vacuo. The dark brown gummy residue was dissolved in boiling iso-propyl acetate (500 ml), cooled to room temperature, seeded and stirred overnight. The pale cream solid produced was filtered off and washed with iso-propyl acetate (100 ml). The solid was sucked dry in the sinter for 1 hour then recrystallized from iso-propyl acetate (400 ml). After stirring overnight the solid formed was filtered off, washed with iso-propyl acetate (80 ml) and dried in vacuo to give the title compound, 110 g, 63.5% yield. 1H NMR ($CDCl_3$, ca 1.9:1 rotamer mixture) δ 0.99 (6H, t), 2.10 (2H, m), 2.50 (4H, q), 2.58/2.62 (2H, 2×t), 2.70/2.82 (2H, 2×t), 2.86 (2H, t), 3.28/3.58 (2H, 2×t), 4.45/4.52 (2H, 2×s), 4.68/4.70 (2H, 2×s), 4.93 (2H, s), 6.95 (2H, m), 7.31 (2H, d), 7.31/7.37 (2H, 2×m), 7.48/7.52 (2H, d), 7.65 (2H, m), 7.72 (2H, m); MS (APCI) $(M+H)^+$ 667; mp 125° C. (by DSC—assymetric endotherm).

Example of Synthesis Approach (I)-1(b)

1-(N-(2-(Diethylamino)ethyl)-N-(4-(4-trifluoromethylphenyl)benzyl)aminocarbonylmethyl)-2-(4-fluorobenzyl)thio-5,6-trimethylenepyrimidin-4-one bitartrate Prepared from intermediates A30 and B69 in WO 01/60805 by the method of Example 1 in WO 01/60805. ¹H-NMR ($d_6$-DMSO, ca 1:1 rotamer mixture) δ 0.92/0.99 (6H, 2×t), 1.99 (2H, m), 2.54 (6H, m), 2.68/2.74 (4H, m), 3.36 (2H, m), 4.21 (2H, s), 4.37/4.44 (2H, 2×s), 4.63/4.74 (2H, 2×s), 4.89/5.13 (2H, 2×s), 7.08/7.14 (2H, 2×m), 7.36-7.50 (4H, m), 7.64/7.70 (2H, 2×d), 7.83 (4H, m); MS (APCI+) found (M+1)=667; $C_{36}H_{38}F_4N_4O_2S$ requires 666.

Example of Synthesis Approach (1)-1(c)

1-(N-(2-(Diethylamino)ethyl)-N-(4-(4-trifluoromethylphenyl)benzyl)aminocarbonylmethyl)-2-(4-fluorobenzyl)thio-5,6-trimethylenepyrimidin-4-one hydrochloride The free base from Example (I)-1(a) (3.00 g, 0.0045 mol) was suspended with stirring in isopropanol (30 ml) and warmed to 45° C. to give a clear solution. The solution was then cooled to ambient temperature and conc. hydrochloric acid (0.40 ml, 0.045 mol) was added. The resultant slurry was then stirred at ambient temperature for 35 minutes, before being cooled to 0° C. for 35 minutes. The slurry was then filtered and washed with isopropanol (10 ml), followed by heptane (30 ml), before being dried under vacuum to give the title compound as a white solid (3.00 g, 95%). $^1$H NMR (CDCl$_3$) δ 1.38 (6H, t), 2.08 (2H, m), 2.82 (2H, t), 2.99 (2H, t), 3.19 (4H, m), 3.35 (2H, m), 3.97 (2H, s), 4.42 (2H, s), 4.81 (2H, s), 4.99 (2H, s), 6.87 (2H, t), 7.26 (2H, t), 7.33 (2H, d), 7.41 (2H, d), 7.53 (2H, d), 7.71 (2H, d), 11.91 (1H, s).

Synthesis of Formula (II)

A description of how to make the compounds of formula (II) and examples of intermediates and final products for the compounds named above can be found in published international application WO 02/30911, which is incorporated herein by reference. A last-step method for making a compound useful in this invention is Example (II)-1.

Example of Synthesis Approach (II)-1

N-(2-Diethylaminoethyl)-2-[2-(2-(2,3-difluorophenyl)ethyl)-4-oxo-4,5,6,7-tetrahydro-cyclopentapyrimidin-1-yl]-N-(4'-trifluoromethyl-biphenyl-4-ylmethyl)acetamide bitartrate

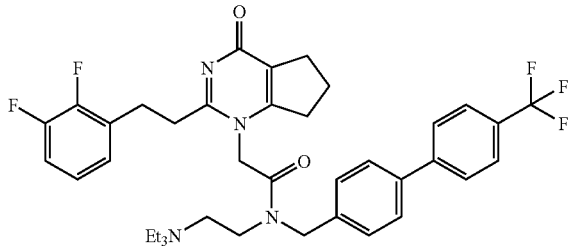

A solution of N,N-diethyl-N-(4'-trifluoromethyl-biphenyl-4-ylmethyl)-ethane-1,2-diamine (Int D4 in WO 02/30911) (0.50 g, 1.44 mmol), 1-(3-dimethylaminopropyl)-3-ethylcarbodiimide (0.56 g, 1.45 mmol), 1-hydroxybenzotriazole hydrate (0.12 g) and 2-(2-[2-(2,3-difluorophenyl)-ethyl]-4-oxo-4,5,6,7-tetrahydro-cyclopentapyrimidin-1-yl)-acetic acid (Int C1 in WO 02/30911) (0.48 g, 1.44 mmol) in dichloromethane (10 ml) was stirred at ambient temperature overnight then diluted with dichloromethane (30 ml), washed with aqueous sodium bicarbonate and evaporated. The residue was purified by chromatography (log silica cartridge, ethyl acetate-acetone) to give the title compound as a yellow foam (free base) (0.50 g, 52%). $^1$H-NMR (DMSO, rotamer mixture) δ 0.83-0.89 (6H, m), 1.98 (2H, m), 2.40 (4H, m), 2.45-2.82 (10H, m), 3.02 (2H, m), 4.64/4.75 (2H, 2×s), 4.96/5.19 (2H, 2×s), 7.11-7.40 (5H, m), 7.65 (2H, m), 7.84 (4H, m); MS (APCI+) found (M+1)=667; $_{37}$H$_{39}$F$_5$N$_4$O$_2$ requires 666.

d-Tartaric acid (0.09 g, 0.60 mmol) was added to a solution of the free base (0.40 g, 0.60 mmol) in methanol (10 ml) with stirring. The resulting solution was evaporated to yield the salt (0.49 g). $^1$H-NMR (DMSO, rotamer mixture) δ 0.85-0.97 (6H, m), 1.91-2.00 (2H, m), 2.40-2.49 (4H, m), 2.54-2.82 (10H, m), 3.02-3.46 (2H, m), 4.20 (2H, s), 4.64/4.75 (2H, 2×s), 4.97/5.18 (2H, 2×s), 7.11-7.40 (5H, m), 7.65 (2H, m), 7.84 (4H, m); MS (APCI+) found (M+1)=667; C$_{37}$H$_{39}$F$_5$N$_4$O$_2$ requires 666.

Following this process, or alternatively other processes described in WO 02/30911, one can prepare the other compounds named above that have the structure of formula (II).

Synthesis of Formula (III)

The overall synthesis of compounds of formula (III) is illustrated in the following scheme III, as presented in WO02/30904:

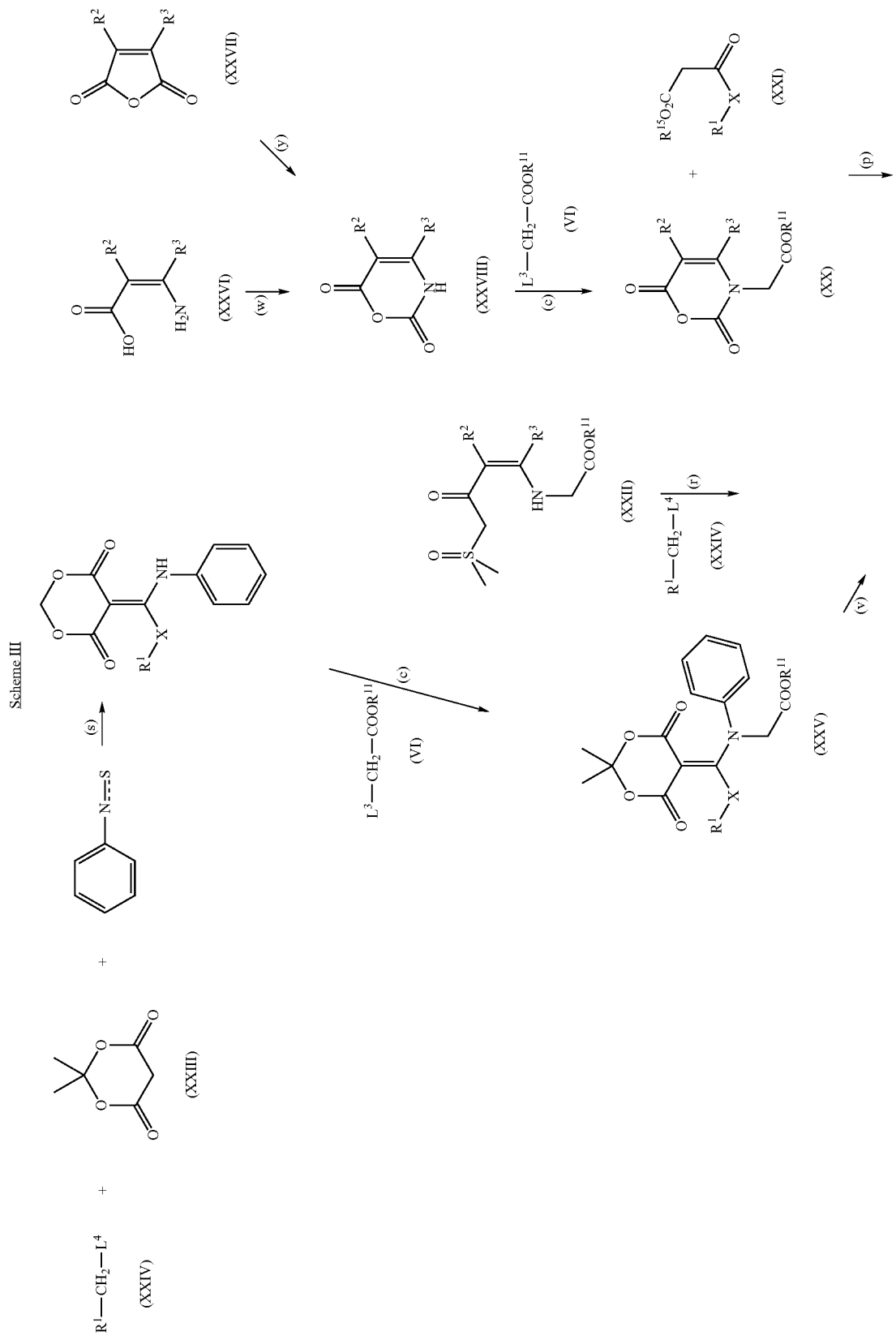

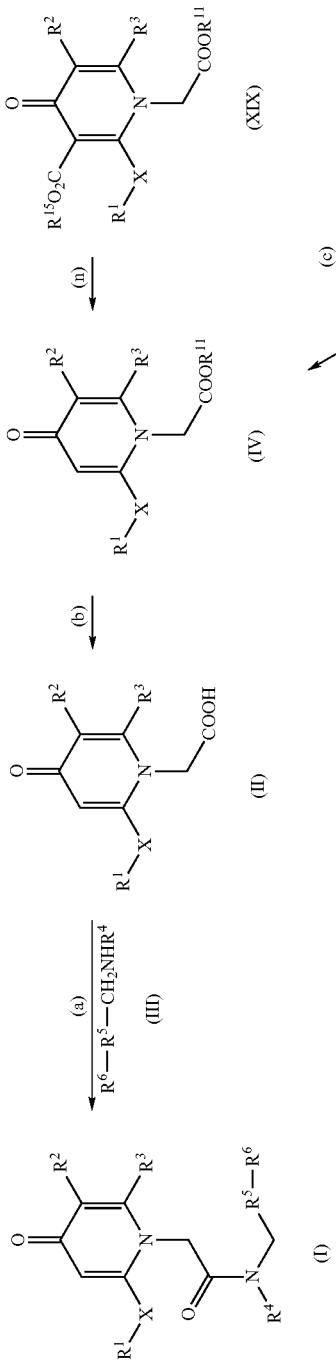
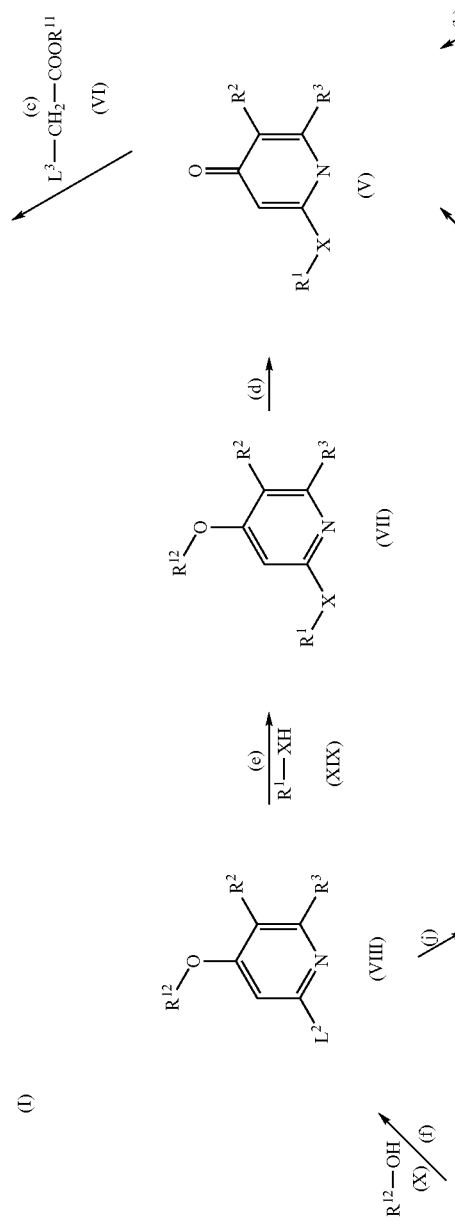
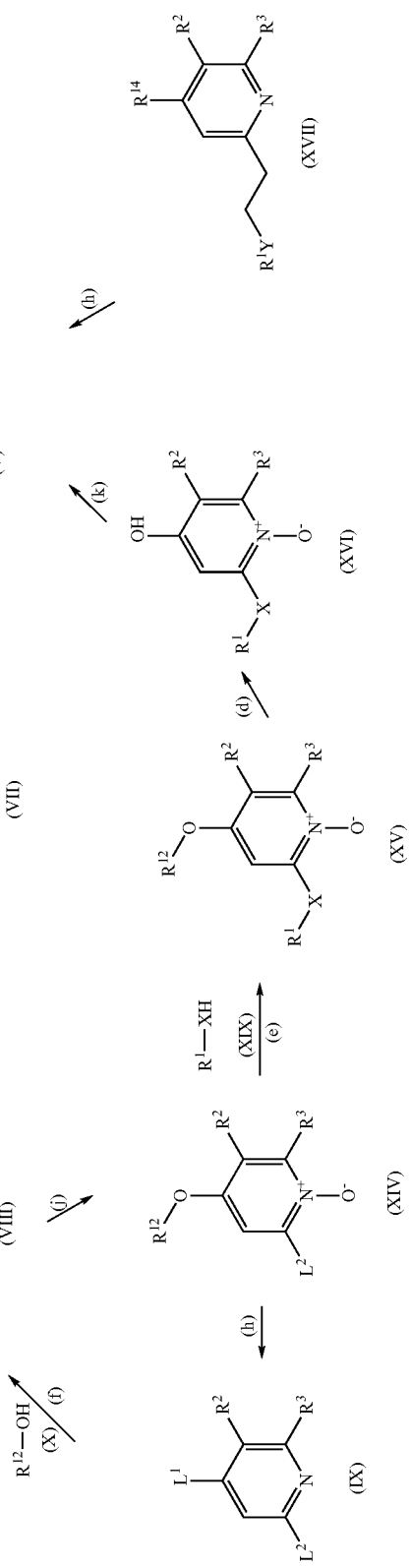

-continued
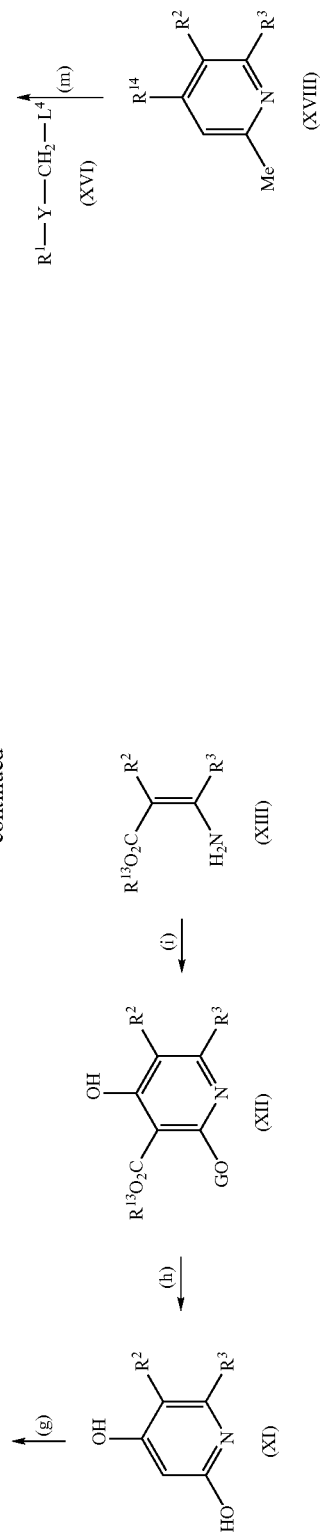

Referring to this scheme, the ester (IV) is usually prepared by N-1 alkylation of (V) using (VI), in which $R^{11}$ is as hereinbefore defined e.g. (VI) is t-butyl bromoacetate or ethyl bromoacetate, in the presence of a base e.g. BuLi in THF or sodium hydride in N-methylpyrrolidinone (NMP) (step c).

When X is $CH_2S$, the key intermediate (IV) can be synthesised by reacting (XX) with dimethyloxosulfonium methylide, generated via the treatment of trimethylsulfoxonium iodide with sodium hydride at low temperature, to yield a sulfur ylid (XXII) (step q). Subsequent treatment of (XXII) with carbon disulfide in the presence of diisopropylamine, followed by $R^1CH_2$-$L^4$, where $L^4$ is a leaving group, yields intermediate (IV) (step r).

Alternatively, when X is $CH_2S$, the $R^1X$ substituent can be introduced by displacement of a leaving group $L^2$ (e.g. Cl) (step e) either on a pyridine (VIII) or pyridine N-oxide (XIV), to give 2-substituted pyridines (VII) and (XV). Transformation of (VII) or (XV) to the 4-pyridone (V) is accomplished by deprotection of the 4-oxygen (e.g. using $(Ph_3P)_3RhCl$ when in aq. ethanol when $R^{12}$=allyl) (step d), followed, for (XVI), by removal of the N-oxide substituent, using hydrogen in the presence of Pd/C in acetic acid (step k). The pyridine (VIII) or pyridine N-oxide (XIV) can be prepared by steps (i), (h), (g), (f), and (j), in which:

(j) treatment of (VIII) with m-chloroperbenzoic acid in dichloromethane;

(f) treatment of (IX) with $R^{12}OH$ (X), in which $R^{12}$ is allyl, and sodium hydride in DMF;

(g) treatment of (XI) with phosphorus oxychloride;

(h) treatment of (XII) with aq HCl with heating;

(i) treatment of (XIII) with di-lower alkyl malonate and sodium alkoxide in alcohol (in which $R^{13}$ is $C_{(1-6)}$alkyl, typically $R^{13}$=Et); and $R^1$—$CH_2SH$ (XIX) is typically prepared from the thioacetate, which is formed from the corresponding alkyl bromide $R^1$—$CH_2Br$.

Alternatively, when X is $CH_2S$ and $R^2$ and $R^3$, together with the pyridone ring carbon atoms to which they are attached, form a fused benzo ring, intermediate (IV) can be synthesised from known starting materials by steps (s), (c) and (v) in which:

(s) treatment of Meldrum's acid (XXIII) with sodium hydride at low temperature, followed by reaction with phenylisothiocyanate and subsequent treatment with $R^1CH_2$-$L^4$;

(c) as hereinbefore discussed;

(v) treatment of (XXV) with trifluoroacetic acid.

When X is alkylene, it is preferable to use steps (m) and (h) (intermediates (XVII), (XVIII)) or steps (n) and (p) (intermediates (XIX), (XX), (XXI)) in which:

(h) transformation of a 4-substituted pyridine into a 4-pyridone e.g. by treatment of (XVII) $R^{14}$=Cl with aq HCl and dioxan, or deprotection of $R^{14}$=$OR^{12}$, e.g. using conditions of step (d).

(m) chain extension of a 2-alkyl pyridine, e.g. where X=$YCH_2CH_2$ by treatment of a 2-methylpyridine (XVIII) with $R^1$—Y—$CH_2$-$L^4$ (XVI) in which $L^4$ is a leaving group and a strong base, such as BuLi, in THF.

In the alternative route, the 3-ester group is removed from intermediate (XIX) $R^{15}$=$C_{(1-6)}$alkyl by heating in diphenyl ether where $R^{15}$=tBu (step n); Intermediate (XIX) is formed from the 2,6-dioxo-1,3-oxazine (XX) and ester (XXI) by treatment with a base such as NaH in DMF or 1,8-diazabicyclo[5.4.0]undec-7-ene in dichloromethane.

Synthesis of (XX) from known starting materials can be achieved via steps (w) and (c) or steps (y) and (c) in which:

(w) treatment of (XXVII) with azidotrimethylsilane in THF;

(y) treatment of (XXVI) with phosgene;

(c) as hereinbefore described.

See WO02/30904, which is incorporated herein by reference, for additional details and exposition of how to make compounds of formula (III).

Example of Synthesis Approach (III)-1

N-(1-(2-Methoxyethyl)piperidin-4-yl)-2-[2-(2,3-difluorobenzylthio)-4-oxo-4H-quinolin-1-yl]-N-(4'-trifluoromethylbiphenyl-4-ylmethyl)acetamide

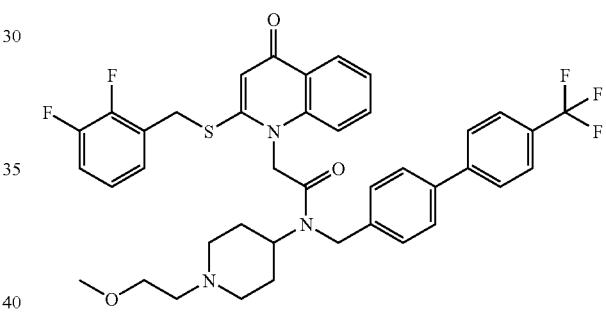

The free base was prepared from Int. E1 and Int. A42 by the method of Example 1 in WO 02/30904, except using DMF as solvent in place of dichloromethane. 1.97 g of this material was crystallised from n.butyl acetate (10 ml) to give the title compound (1.35 g). $^1$H-NMR ($CD_3OD$) δ 1.7-2.05 (4H, m), 2.05-2.3 (2H, 2×0, 2.5-2.65 (2H, m), 2.95-3.1 (2H, m), 3.3 (3H, s), 3.45-3.55 (2H, m), 3.9-4.05+4.4-4.5 (1H, 2×m), 4.37+4.48 (2H, 2×s), 4.71+4.87 (2H, 2×br s), 5.31+5.68 (2H, 2×s), 6.44+6.52 (1H, 2×s), 6.95-7.3 (3H, m), 7.35-7.85 (11H, m), 8.2-8.35 (1H, m); MS (APCI+) found (M+1) 736; $C_{40}H_{38}F_5N_3O_3S$ requires 735.

Synthesis of Formula (IV)

The following flow chart illustrates a process for making the compounds of this invention.

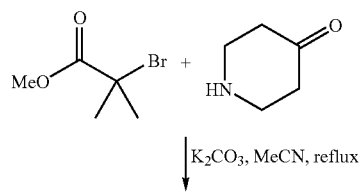

$K_2CO_3$, MeCN, reflux

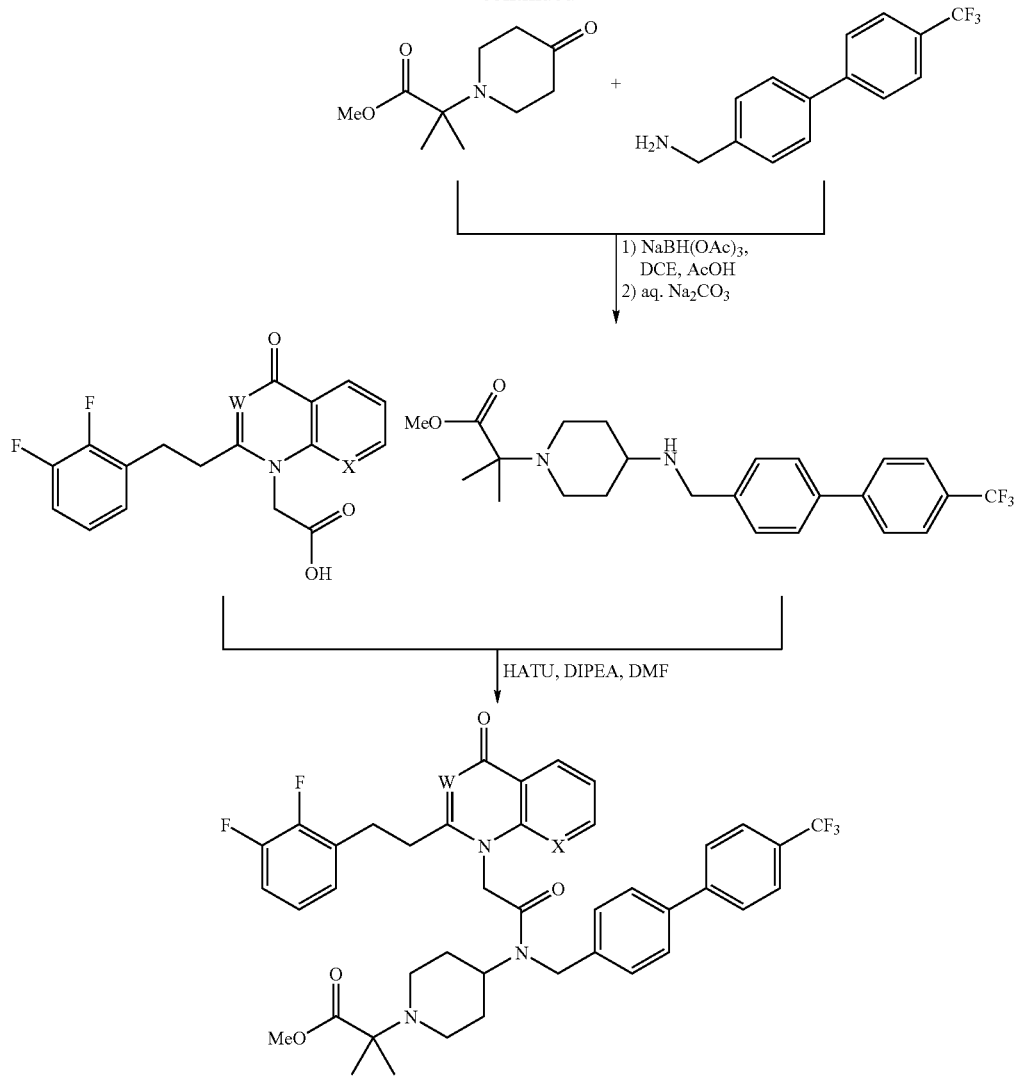

In addition, the reader is referred to published PCT application WO 03/016287 for chemistries that can be useful in preparing some of the intermediates set out in this flow chart. Those chemistries, to the extent they are useful in this case, are incorporated herein by reference as though it was fully set out herein. In addition, reference is made to the syntheses set out in published PCT applications WO 01/60805, WO 02/30911, WO 02/30904, WO 03/042218, WO 03/042206, WO 03/041712, WO 03/086400, and WO 03/87088, and co-pending U.S. provisional applications 60/829,328 and 60/829,327 both filed 13 Oct. 2006 noted above. To the extent the reader wishes to prepare the compounds of formula (IV) by using intermediates, reagents, solvents, times, temperatures, etc., other than those in the route on the foregoing page, these published PCT applications and co-pending US applications can provide useful guidance. To the extent the chemistries in these applications are pertinent to making the instant compounds, those materials are incorporated herein by reference.

Intermediate (IV)-A1 {[4'-(Trifluoromethyl)-4-biphenylyl]methyl}amine

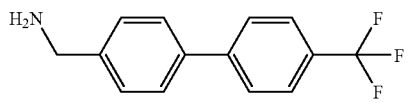

The preparation of this compound was described in WO 02/30911 as Intermediate D7.

Intermediate (IV)-A2 ({4'-[(Trifluoromethyl)oxy]-4-biphenylyl}methyl)amine hydrochloride

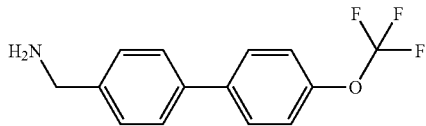 [SMILES: NCc1ccc(-c2ccc(OC(F)(F)F)cc2)cc1]

A solution of 4'-[(trifluoromethyl)oxy]-4-biphenylcarbonitrile (prepared from {4-[(trifluoromethyl)oxy]phenyl}boronic acid by a method analogous to that described for the 4'-trifluoromethyl analogue, Intermediate D6 of WO 02/30911) (66.6 g) in ethanol (2000 ml) and concentrated hydrochloric acid (100 ml) was hydrogenated over Pearlman's catalyst (10 g) at 25 psi until reduction was complete. The catalyst was removed by filtration through celite, then the solvent was removed in vacuo to obtain the desired product.

LCMS Rt=2.212 minutes; m/z [M+H]$^+$=251.0

Intermediates for Making Formula (IV)

Intermediate (IV)-A3

Methyl 2-methyl-2-(4-oxo-1-piperidinyl)propanoate

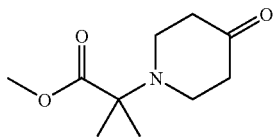

A mixture of methyl 2-bromo-2-methylpropanoate (80.87 ml, 5 equiv), 4-piperidone hydrochloride monohydrate (19.6 g, 1 equiv), acetonitrile (200 ml) and potassium carbonate (69.1 g, 4 equiv) was heated at reflux under nitrogen with mechanical stirring for 17.5 h then cooled in an ice bath before adding diethyl ether (100 ml). Filtration through celite followed by flash chromatography (silica, 10-50% ethyl acetate in hexane) and evaporation of the product fractions gave the desired product as a yellow oil (14.28 g).

$^1$H NMR (CDCl$_3$) δ 1.41 (6H, s), 2.47 (4H, m), 2.88 (4H, m), 3.73 (3H, s).

Intermediate (IV)-A4

Ethyl 2-methyl-2-(4-oxo-1-piperidinyl)propanoate

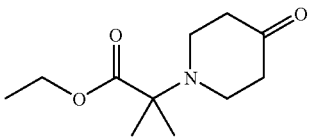

A mixture of ethyl 2-bromo-2-methylpropanoate (48.3 ml, 5 equiv), 4-piperidone hydrochloride monohydrate (100 g, 1 equiv), acetonitrile (1216 ml) and potassium carbonate (353 g, 4 equiv) was heated at reflux under nitrogen with mechanical stirring for 20 h then cooled in an ice bath before adding diethyl ether (approx. 1400 ml). The mixture was filtered through celite, evaporated in vacuo, then excess bromoester distilled off (50° C. still head temperature/10 Torr). Flash chromatography (silica, 5-30% ethyl acetate in hexane) and evaporation of the product fractions gave the crude product as a yellow oil. To remove some remaining bromoester contaminant this was partitioned between ethyl acetate and 2M aqueous hydrochloric acid. The organic layer was discarded and the aqueous layer was basified with sodium carbonate, saturated with sodium chloride and extracted with ethyl acetate. Drying and evaporation of the organic extracts gave the desired product as a yellow oil (54.7 g).

$^1$H NMR (CDCl$_3$) δ 1.27 (3H, t), 1.40 (6H, s), 2.47 (4H, m), 2.90 (4H, m), 4.20 (2H, q).

Intermediate (IV)-A5

1,1-Dimethylethyl 2-methyl-2-(4-oxo-1-piperidinyl)propanoate

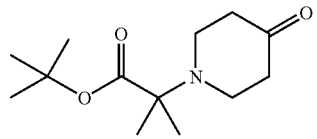 [SMILES: CC(C)(C)OC(=O)C(C)(C)N1CCC(=O)CC1]

A mixture of 1,1-dimethylethyl 2-bromo-2-methylpropanoate (8.0 g, 1.1 equiv), 4-piperidone hydrochloride (5.0 g, 1 equiv), acetone (50 ml) and potassium carbonate (13.0 g, 3 equiv) was heated at reflux with stirring for 24 h, then filtered and the filtrate evaporated. The crude residue was used in the next step without purification.

ES+MS m/z [M+H-tBu]$^+$=186.1

Intermediate (IV)-B1

Methyl 2-methyl-2-[4-({[4'-(trifluoromethyl)-4-biphenylyl]methyl}amino)-1-piperidinyl]propanoate

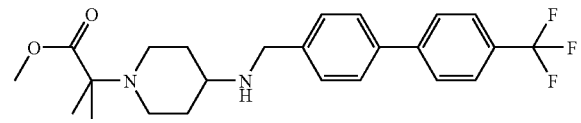

A mixture of methyl 2-methyl-2-(4-oxo-1-piperidinyl)propanoate (Int. A3) (14.28 g, 1 equiv), {[4'-(trifluoromethyl)-4-biphenylyl]methyl}amine (Int. A1) (19.6 g, 0.85 equiv), DCE (300 ml), acetic acid (3.8 ml, 0.90 equiv) and sodium triacetoxyborohydride (20.7 g, 1.25 equiv) was stirred at room temperature under nitrogen for 17.5 h. Aqueous sodium carbonate (2M solution, excess) was added and stirred for 4 h, then the mixture was extracted with a mixture of diethyl ether and THF. The organic extracts were backwashed with water and brine, dried over sodium sulfate and filterered through a pad of silica gel which was rinsed with 2.5% methanol in DCM. After evaporation in vacuo, the crude product was crystallised from ether/hexane, finally at ice bath temperature, which after drying yielded a white solid (20.9 g).

LCMS Rt=2.070 minutes; m/z [M+H]$^+$=435.2

$^1$H NMR (d$_6$-DMSO) δ 1.15-1.32 (8H, m), 1.75-187 (2H, m), 1.97-2.12 (2H, m), 2.27-2.40 (1H, m), 2.77-2.90 (2H, m), 3.60 (3H, s), 3.76 (2H, s), 7.46 (2H, d, J=8.03 Hz), 7.67 (2H, d, J=8.28 Hz), 7.80 (2H, d, J=8.53 Hz), 7.88 (2H, d, 8.03 Hz)

Intermediate (IV)-B2

Ethyl 2-methyl-2-[4-({[4'-(trifluoromethyl)-4-biphenylyl]methyl}amino)-1-piperidinyl]propanoate

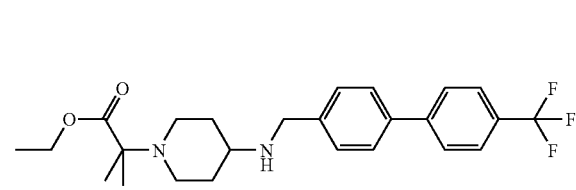

A mixture of ethyl 2-methyl-2-(4-oxo-1-piperidinyl)propanoate (Int. A4) (25.6 g, 1.2 equiv), {[4'-(trifluoromethyl)-4-biphenylyl]methyl}amine (Int. A1) (31.1 g, 1.0 equiv), DCE (400 ml) and acetic acid (6.3 ml, 1.1 equiv) was stirred at room temperature under nitrogen. Sodium triacetoxyborohydride (33.5 g, 1.5 equiv) was added and stirring continued for 19 hours. Aqueous sodium carbonate (2M solution, excess) was added and stirred for 1.5 h, then the mixture was extracted with a mixture of diethyl ether and THF. The organic extracts were backwashed with water and brine, filterered through a pad of silica gel, dried over sodium sulfate and evaporated in vacuo. The desired product was obtained as a white solid (44.2 g) which was used without further purification.

LCMS Rt=2.194 minutes; m/z [M+H]$^+$=449.3

$^1$H NMR (d$_6$-DMSO) δ 1.06-1.32 (11H, m), 1.74-1.89 (2H, m), 1.99-2.14 (2H, m), 2.25-2.39 (1H, m), 2.69-2.89 (2H, m), 3.75 (2H, s), 4.01-4.12 (2H, m), 7.45 (2H, d, J=7.55 Hz), 7.67 (2H, d, J=7.81 Hz), 7.79 (2H, d, J=8.06 Hz), 7.88 (2H, d, J=8.06 Hz)

Intermediate (IV)-B3

Ethyl 2-methyl-2-{4-[({4'-[(trifluoromethyl)oxy]-4-biphenylyl}methyl)amino]-1-piperidinyl}propanoate

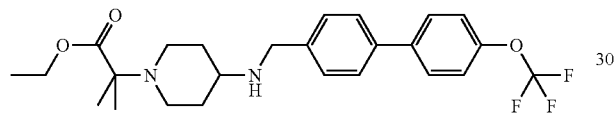

A mixture of ethyl 2-methyl-2-(4-oxo-1-piperidinyl)propanoate (Int. A4) (1.09 g, 1.2 equiv), ({4'-[(trifluoromethyl)oxy]-4-biphenylyl}methyl)amine hydrochloride (Int. A2) (1.28 g, 1.0 equiv), DCE (21 ml) and acetic acid (0.27 ml, 1.1 equiv) was stirred at room temperature under nitrogen. Sodium triacetoxyborohydride (1.42 g, 1.5 equiv) was added and stirring contined for 3 hours. Aqueous sodium carbonate (2M solution, excess) was added and stirred for 45 min, then the mixture was partitioned with a mixture of diethyl ether/THF and water. The organic extracts were backwashed with water and brine, and dried over sodium sulfate and evaporated in vacuo. The desired product was obtained as a light yellow solid (2.14 g) which was used without further purification.

LCMS Rt=2.244 minutes; m/z [M+H]$^+$=465.3

Intermediate (IV)-B4

1,1-Dimethylethyl 2-methyl-2-[4-({[4'-(trifluoromethyl)-4-biphenylyl]methyl}amino)-1-piperidinyl]propanoate

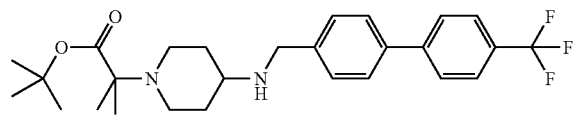 [SMILES: CC(C)(C)OC(=O)C(C)(C)N1CCC(NCc2ccc(-c3ccc(C(F)(F)F)cc3)cc2)CC1]

A mixture of 1,1-dimethylethyl 2-methyl-2-(4-oxo-1-piperidinyl)propanoate (Int. A6) (370 mg, 1.2 equiv), {[4'-(trifluoromethyl)-4-biphenylyl]methyl}amine (Int. A1) (397 mg, 1 equiv), sodium triacetoxyborohydride (400 mg, 1.5 equiv), DCM (10 ml) and acetic acid (0.076 ml, 1 equiv) was combined and stirred at room temperature until LCMS confirmed disappearance of the amine starting material (approx. 18 hours). Aqueous sodium carbonate was added and then extracted with DCM. The organics were dried over sodium sulfate and concentrated to give a solid (420 mg) that was used without further purification.

LCMS Rt=2.24 minutes; m/z [M+H]$^+$=477.3

Intermediate (IV)-C1

[2-[2-(2,3-Difluorophenyl)ethyl]-4-oxo-1(4H)-quinazolinyl]acetic acid

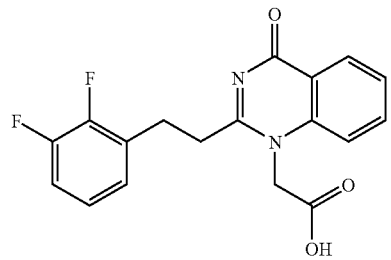 [SMILES: O=C(O)Cn1c(CCc2cccc(F)c2F)nc(=O)c2ccccc21]

The preparation of this compound was described in WO 02/30911 as Intermediate C43.

Intermediate (IV)-C2

[2-[2-(2,3-Difluorophenyl)ethyl]-4-oxo-1,8-naphthyridin-1(4H)-yl]acetic acid

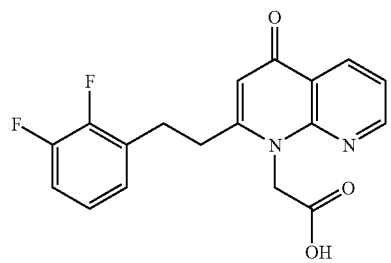 [SMILES: O=C(O)Cn1c(CCc2cccc(F)c2F)cc(=O)c2cccnc21]

The preparation of this compound was described in WO 02/30904 as Intermediate E21.

Intermediate (IV)-C3

[2-[2-(2,4-Difluorophenyl)ethyl]-4-oxo-1(4H)-quinazolinyl]acetic acid

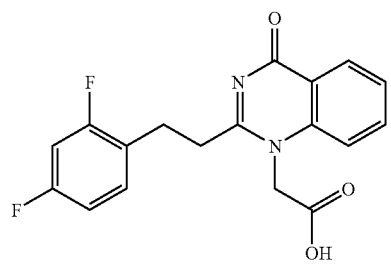 [SMILES: O=C(O)Cn1c(CCc2ccc(F)cc2F)nc(=O)c2ccccc21]

The preparation of this compound was described in WO 02/30911 as Intermediate C45.

Intermediate (IV)-C4

Ethyl [2-[2-(2,4-difluorophenyl)ethyl]-4-oxopyrido[2,3-d]pyrimidin-1(4H)-yl]acetate

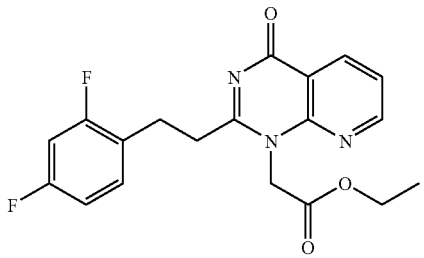 [SMILES: CCOC(=O)Cn1c(CCc2ccc(F)cc2F)nc(=O)c2cccnc21]

A mixture of ethyl (2,4-dioxo-3,4-dihydropyrido[2,3-d]pyrimidin-1(2H)-yl)acetate (WO 02/30911, Intermediate B52) (40.8 g, 1.2 equiv) and 3-(2,4-difluorophenyl)propanimidamide (made by methods analogous to those described for the 2,3-difluoro isomer, Intermediates A1 to A3 of WO 02/30911) (30.0 g, 1 equiv) was fused in a 150° C. oil bath for 25 min, then cooled quickly to room temperature in a water bath. Chromatography (silica, crude product loaded in DCM and eluted with 50-100% ethyl acetate in hexane) gave the desired product (43.56 g).

LCMS Rt=2.521 minutes; m/z [M+H]$^+$=374.1

$^1$H NMR (CDCl$_3$) δ 1.31 (3H, t), 3.13 (2H, m), 3.26 (2H, m), 4.28 (2H, q), 5.27 (2H, s), 6.82 (2H, m), 7.34 (1H, m), 7.50 (1H, m), 8.65 (1H, m), 8.74 (1H, m).

Intermediate (IV)-C5

[2-[2-(2,3-Difluorophenyl)ethyl]-4-oxopyrido[2,3-d]pyrimidin-1(4H)-yl]acetic acid

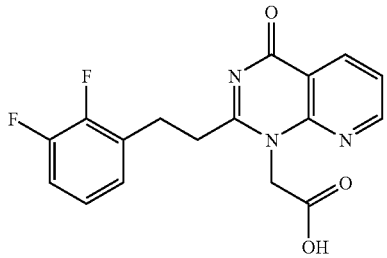 [SMILES: O=C(O)Cn1c(CCc2cccc(F)c2F)nc(=O)c2cccnc21]

The preparation of this compound was described in WO 02/30911 as Intermediate C35.

Intermediate (IV)-C5

[2-[2-(2,4-Difluorophenyl)ethyl]-4-oxopyrido[2,3-d]pyrimidin-1(4H)-yl]acetic acid

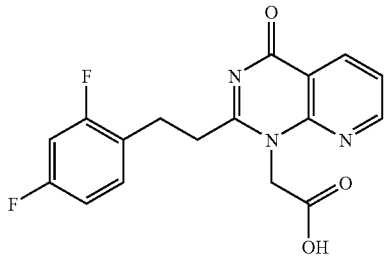 [SMILES: O=C(O)Cn1c(CCc2ccc(F)cc2F)nc(=O)c2cccnc21]

Ethyl[2-[2-(2,4-difluorophenyl)ethyl]-4-oxopyrido[2,3-d]pyrimidin-1(4H)-yl]acetate (Int. C1) (32.76 g, 1 equiv) was dissolved in ethanol (350 ml) and water (70 ml), cooled in ice, then aqueous lithium hydroxide (2M solution, 43.42 ml, 0.99 equiv) was added. Stirring was continued for 2 h at room temperature. The solution was concentrated in vacuo and the residue was redissolved in water (700 ml) and saturated aqueous sodium bicarbonate (50 ml), then washed with ethyl acetate (200 ml). The aqueous layer was acidified to pH 2 with 2M hydrochloric acid, and the precipitate was filtered off, washed with ice water (50 ml) and dried in vacuo (50° C., 16 h) to obtain the desired product (23.2 g).

$^1$H NMR (d$_6$-DMSO) δ 2.4-2.6 (4H, m), 5.24 (2H, s), 7.04 (1H, m), 7.22 (1H, m), 7.48 (1H, m), 7.60 (1H, m), 8.47 (1H, m), 8.84 (1H, m).

Example (IV)-1

Methyl 2-[4-({[2-[2-(2,3-difluorophenyl)ethyl]-4-oxo-1(4H)-quinazolinyl]acetyl}{[4'-(trifluoromethyl)-4-biphenylyl]methyl}amino)-1-piperidinyl]-2-methylpropanoate 2,3-dihydroxybutanedioate (salt)

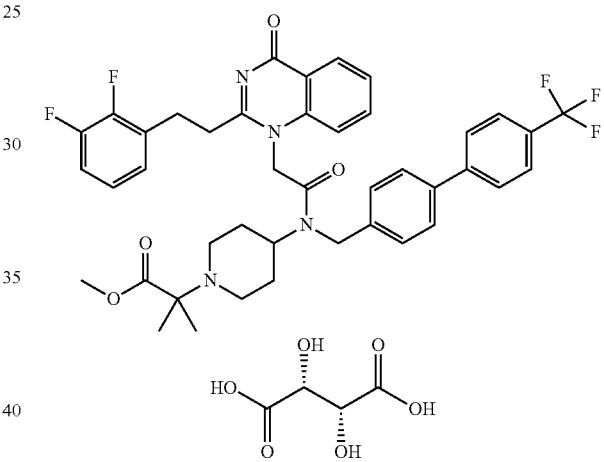

A mixture of [2-[2-(2,3-difluorophenyl)ethyl]-4-oxo-1(4H)-quinazolinyl]acetic acid (Int. C1) (100 mg, 1 equiv), methyl 2-methyl-2-[4-({[4'-(trifluoromethyl)-4-biphenylyl]methyl}amino)-1-piperidinyl]propanoate (Int. B1) (130 mg, 1.03 equiv), DIPEA (0.1 ml, 3.6 equiv), acetonitrile (2 ml) and HATU (130 mg, 1.4 equiv) was stirred at room temperature for 1 h, then evaporated and redissolved in acetonitrile. Purification by reverse phase HPLC (Preparative Method A) gave methyl 2-[4-({[2-[2-(2,3-difluorophenyl)ethyl]-4-oxo-1(4H)-quinazolinyl]acetyl}{[4'-(trifluoromethyl)-4-biphenylyl]methyl}amino)-1-piperidinyl]-2-methylpropanoate (128 mg).

LCMS Rt=2.686 minutes; m/z [M+H]$^+$=761.3

$^1$H NMR (CDCl$_3$) δ 1.33 (3H, s), 1.36 (3H, s), 1.83-2.02 (4H, m), 2.36-2.48 (2H, m), 2.87-2.91 (1H, m), 3.06-3.09 (2H, m), 3.16-3.20 (2H, m), 3.26-3.29 (1H, m), 3.71-3.73 (3H, m), 4.02/4.51 (1H, 2×br m), 4.74 (1H, s), 4.92 (1H, s), 5.12 (1H, s), 5.56 (1H, s), 7.00-7.19 (3H, m), 7.32-7.37 (1H, m), 7.48-7.62 (5H, m), 7.72-7.81 (5H, m), 8.22-8.28 (1H, m).

The free base was converted to the bitartrate salt by adding L-tartaric acid (1.675 g, 1.0 equiv) in one portion and stirred for 30 minutes at room temperature. The solution was concentrated in vacuo to an off-white powder that was dried in a vacuum oven at room temperature.

Example of Synthesis Approach (IV)-2

Methyl 2-[4-({[2-[2-(2,3-difluorophenyl)ethyl]-4-oxo-1,8-naphthyridin-1(4H)-yl]acetyl}{[4'-(trifluoromethyl)-4-biphenylyl]methyl}amino)-1-piperidinyl]-2-methylpropanoate 2,3-dihydroxybutanedioate (salt)

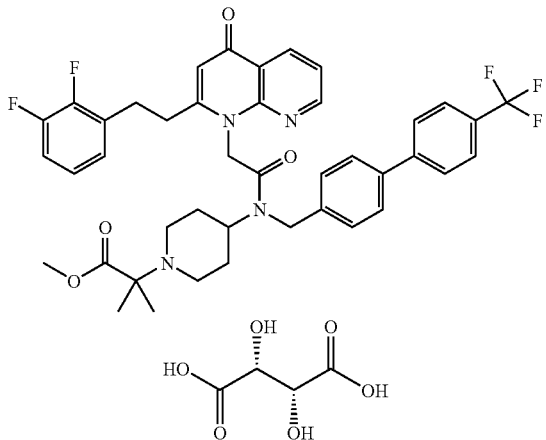

A mixture of [2-[2-(2,3-difluorophenyl)ethyl]-4-oxo-1,8-naphthyridin-1(4H)-yl]acetic acid (Int. C2) (100 mg, 1 equiv), carbonyldiimidazole (50 mg, 1.05 equiv) and dimethylacetamide (4 ml) was stirred at 60° C. for 30 min then methyl 2-methyl-2-[4-({[4'-(trifluoromethyl)-4-biphenylyl]methyl}amino)-1-piperidinyl]propanoate (Int. B1) (132 mg, 1.05 equiv) was added and the temperature raised to 80° C. for 2 h. A further portion of carbonyldiimidazole (0.5 equiv) was added and stirring continued at 80° C. for 15 h. After cooling the crude mixture was applied to reverse phase HPLC (Preparative Method A) to obtain methyl 2-[4-({[2-[2-(2,3-difluorophenyl)ethyl]-4-oxo-1,8-naphthyridin-1(4H)-yl]acetyl}{[4'-(trifluoromethyl)-4-biphenylyl]methyl}amino)-1-piperidinyl]-2-methylpropanoate (99 mg).

LCMS Rt=2.845 minutes; m/z [M+H]$^+$=761.3

$^1$H NMR (CDCl$_3$) δ 1.28 (3H, s), 1.31 (3H, s), 1.73-2.05 (4H, m), 2.25 (1H, t), 2.39-2.46 (1H, m), 2.96-2.99 (1H, m), 3.00-3.12 (4H, m), 3.19 (1H, s), 3.68-3.73 (3H, m), 4.11/4.41 (1H, 2×br m), 4.73 (1H, s), 4.97 (1H, s), 5.51 (1H, s), 6.29-6.34 (1H, m), 7.06-7.20 (2H, m), 7.35-7.41 (1H, m), 7.48-7.58 (2H, m), 7.68-7.84 (6H, m), 8.60-8.68 (1H, m), 8.87-8.91 (1H, m).

This was converted to the bitartrate salt by a method analogous to that described for Example of Synthesis Approach (I).

Example of Synthesis Approach (IV)-3

Ethyl 2-[4-({[2-[2-(2,3-difluorophenyl)ethyl]-4-oxo-1(4H)-quinazolinyl]acetyl}{[4'-(trifluoromethyl)-4-biphenylyl]methyl}amino)-1-piperidinyl]-2-methylpropanoate 2,3-dihydroxybutanedioate (salt)

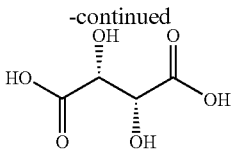

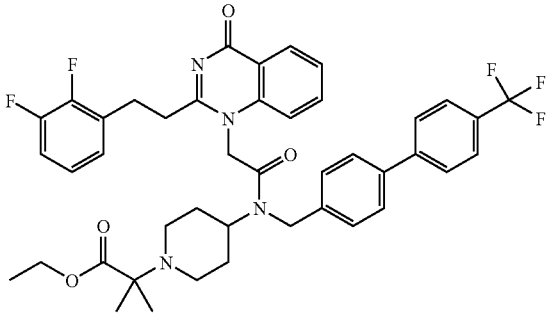

A mixture of [2-[2-(2,3-difluorophenyl)ethyl]-4-oxo-1(4H)-quinazolinyl]acetic acid (Int. C1) (115 mg, 1 equiv), ethyl 2-methyl-2-[4-({[4'-(trifluoromethyl)-4-biphenylyl]methyl}amino)-1-piperidinyl]propanoate (Int. B2) (150 mg, 1 equiv), HATU (151 mg, 1.2 equiv), DMF (2.7 ml) and DIPEA (0.17 ml, 3 equiv) was shaken at room temperature for 5 h. The reaction mixture was partitioned between ethyl acetate/methanol and aqueous sodium bicarbonate, then the organic layer was brine-washed and dried. Flash chromatography (silica, 3-4% methanol in DCM) gave ethyl 2-[4-({[2-[2-(2,3-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoate as a white solid (190 mg).

LCMS Rt=2.55 minutes; m/z [M+H]$^+$=775.3

$^1$H NMR (CDCl$_3$) δ 1.18-1.40 (9H, m), 1.61-2.09 (4H, m), 2.22-2.45 (2H, m), 2.75-2.85 (1H, m), 2.90-3.34 (5H, m), 3.71/4.66 (1H, 2×m), 4.12-4.26 (2H, m), 4.70-4.85 (3H, m), 5.08 (1H, s), 6.80-6.88 (1H, m), 6.95-7.13 (3H, m), 7.27-7.33 (1H, m), 7.34-7.52 (3H, m), 7.56-7.62 (1H, m), 7.63-7.77 (4H, m), 8.29-8.44 (2H, m).

This was converted to the bitartrate salt by a method analogous to that described in Example of Synthesis Approach (I).

Example of Synthesis Approach (IV)-4

Ethyl 2-{4-[{[2-[2-(2,3-difluorophenyl)ethyl]-4-oxo-1(4H)-quinazolinyl]acetyl}({4'-[(trifluoromethyl)oxy]-4-biphenylyl}methyl)amino]-1-piperidinyl}-2-methylpropanoate 2,3-dihydroxybutanedioate (salt)

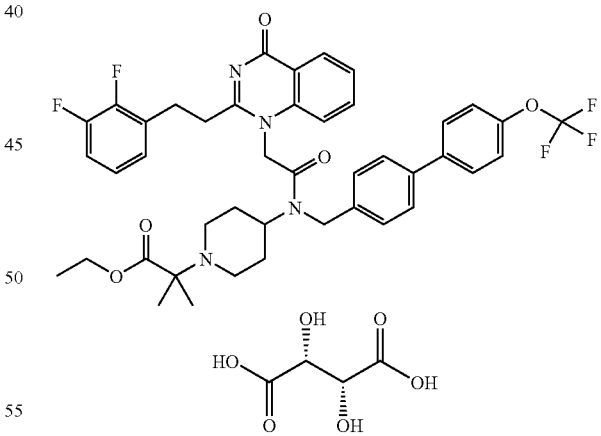

A mixture of [2-[2-(2,3-difluorophenyl)ethyl]-4-oxo-1(4H)-quinazolinyl]acetic acid (Int. C1) (124 mg, 1.2 equiv), ethyl 2-methyl-2-{4-[({4'-[(trifluoromethyl)oxy]-4-biphenylyl}methyl)amino]-1-piperidinyl}propanoate (Int. B3) (139 mg, 1 equiv), DMF (1.2 ml) and DIPEA (0.16 ml, 3 equiv) was shaken at room temperature for 30 min, then HATU (176 mg, 1.5 equiv) was added and shaking continued for 4 h. Reverse phase HPLC (Preparative Method B) gave ethyl 2-{4-[{[2-[2-(2,3-difluorophenyl)ethyl]-4-oxo-1(4H)-quinazolinyl]acetyl}({4'-[(trifluoromethyl)oxy]-4- biphenylyl}methyl)amino]-1-piperidinyl}-2-methylpropanoate as a white solid (174 mg).

LCMS Rt=2.77 minutes; m/z [M+H]$^+$=791.3

$^1$H NMR (CDCl$_3$) Characteristic peaks: δ 1.21-1.42 (9H, m), 1.58-2.08 (4H, m), 2.20-2.48 (2H, m), 2.71-5.1 (13H, br m), 6.79-6.87 (1H, d), 6.92-7.11 (3H, m), 7.30-7.46 (5H, m), 7.48-7.63 (5H, m), 8.26-8.40 (1H, m)

This was converted to the bitartrate salt by a method analogous to that described in Example of Synthesis Approach (I).

Example of Synthesis Approach (IV)-5

Methyl 2-[4-({[2-[2-(2,4-difluorophenyl)ethyl]-4-oxo-1(4H)-quinazolinyl]acetyl}{[4'-(trifluoromethyl)-4-biphenylyl]methyl}amino)-1-piperidinyl]-2-methylpropanoate 2,3-dihydroxybutanedioate (salt)

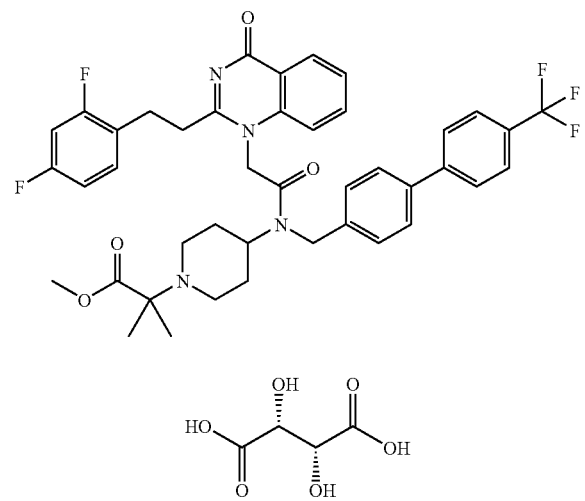

mixture of [2-[2-(2,4-difluorophenyl)ethyl]-4-oxo-1(4H)-quinazolinyl]acetic acid (Int. C3) (100 mg, 1 equiv), methyl 2-methyl-2-[4-({[4'-(trifluoromethyl)-4-biphenylyl]methyl}amino)-1-piperidinyl]propanoate (Int. B1) (130 mg, 1.03 equiv), DIPEA (0.1 ml, 2 equiv), acetonitrile (2 ml) and HATU (130 mg, 1.4 equiv) was stirred at room temperature for 1 h, then evaporated and redissolved in acetonitrile. Purification by reverse phase HPLC (Preparative Method B) gave methyl 2-[4-({[2-[2-(2,4-difluorophenyl)ethyl]-4-oxo-1(4H)-quinazolinyl]acetyl}{[4'-(trifluoromethyl)-4-biphenylyl]methyl}amino)-1-piperidinyl]-2-methylpropanoate (126 mg).

LCMS Rt=2.698 minutes; m/z [M+H]$^+$=761.3

$^1$H NMR (CDCl$_3$) δ 1.30 (3H, s), 1.34 (3H s), 1.81-2.03 (4H, m), 2.29-2.35 (1H, m), 2.39-2.45 (1H, m), 2.82-2.87 (1H, m), 3.00-3.14 (4H, m), 3.19-3.24 (1H, m), 3.70-3.73 (3H, m), 4.00/4.51 (1H, 2×br m), 4.74 (1H, s), 4.91 (1H, s), 5.10 (1H, s), 5.54 (1H, s), 6.77-6.84 (1H, m), 6.87-6.98 (1H, m), 7.28-7.43 (2H, m), 7.48-7.61 (5H, m), 7.73-7.81 (5H, m), 8.23-8.29 (1H, m).

This was converted to the bitartrate salt by a method analogous to that described in Example of Synthesis Approach (I).

Example Synthesis Approach (IV)-6

Ethyl 2-[4-({[2-[2-(2,4-difluorophenyl)ethyl]-4-oxo-1(4H)-quinazolinyl]acetyl}{[4'-(trifluoromethyl)-4-biphenylyl]methyl}amino)-1-piperidinyl]-2-methylpropanoate 2,3-dihydroxybutanedioate (salt)

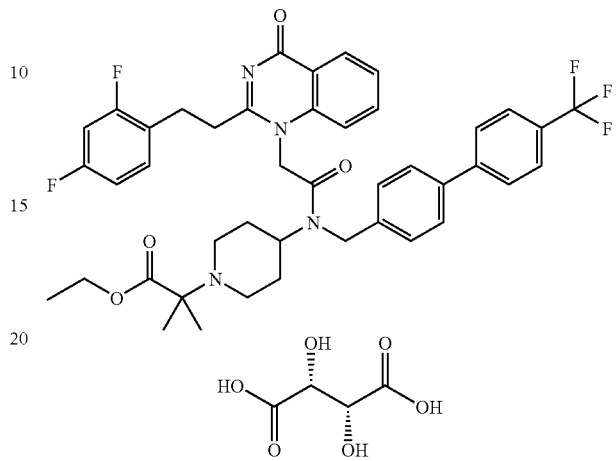

A mixture of [2-[2-(2,4-difluorophenyl)ethyl]-4-oxo-1 (4H)-quinazolinyl]acetic acid (Int. C3) (120 mg, 1 equiv), ethyl 2-methyl-2-[4-({[4'-(trifluoromethyl)-4-biphenylyl] methyl}amino)-1-piperidinyl]propanoate (Int. B2) (204 mg, 1.3 equiv), DMF (1.4 ml) and DIPEA (0.183 ml, 3 equiv) was shaken at room temperature, then HATU (206 mg, 1.5 equiv) was added with vigorous agitation and shaking continued for 1.5 h. A further portion of Intermediate D5 (12 mg, 0.1 equiv) was added then shaking was continued for 2 days. Reverse phase HPLC (Preparative Method B) gave ethyl 2-[4-({[2-[2-(2,4-difluorophenyl)ethyl]-4-oxo-1(4H)-quinazolinyl] acetyl}{[4'-(trifluoromethyl)-4-biphenylyl]methyl}amino)-1-piperidinyl]-2-methylpropanoate as a white solid (173 mg).

LCMS Rt=2.751 minutes; m/z [M+H]$^+$=775.3

$^1$H NMR (CDCl$_3$) δ (mixture of rotomers) Characteristic peaks: 1.22-1.47 (9H, m), 1.63-2.10 (4H, m), 2.16-5.11 (15H, br m), 6.75-6.88 (2H, m), 7.14-7.80 (12H, m), 8.26-8.40 (1H, m).

This was converted to the bitartrate salt by a method analogous to that described in Example of Synthesis Approach (I).

Example Synthesis Approach (IV)-7

Ethyl 2-{4-[{[2-[2-(2,4-difluorophenyl)ethyl]-4-oxo-1(4H)-quinazolinyl]acetyl}({4'-[(trifluoromethyl)oxy]-4-biphenylyl}methyl)amino]-1-piperidinyl}-2-methylpropanoate 2,3-dihydroxybutanedioate (salt)

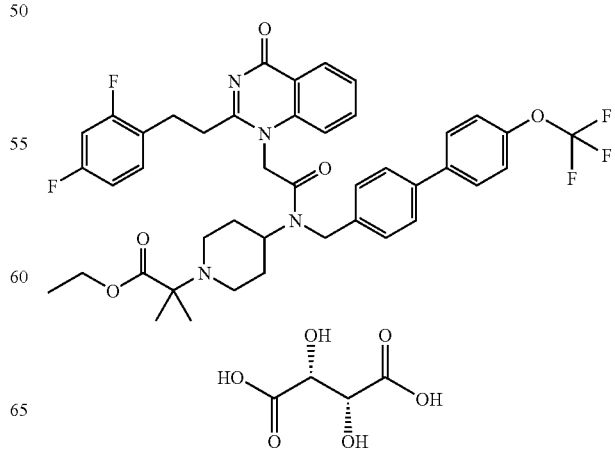

A mixture of [2-[2-(2,4-difluorophenyl)ethyl]-4-oxo-1 (4H)-quinazolinyl]acetic acid (Int. C3) (114 mg, 1.1 equiv), ethyl 2-methyl-2-{4-[({4'-[(trifluoromethyl)oxy]-4-biphenylyl}methyl)amino]-1-piperidinyl}propanoate (Int. B3) (139 mg, 1 equiv), DMF (1.2 ml) and DIPEA (0.16 ml, 3 equiv) was shaken at room temperature, then HATU (176 mg, 1.5 equiv) was added with vigorous agitation and shaking continued for 30 min. A further portion of Intermediate D5 (21 mg, 0.2 equiv) was added, followed 1 h later by further HATU (23 mg, 0.2 equiv), then shaking was continued for 18 h. Reverse phase HPLC (Preparative Method B) gave ethyl 2-{4-[{[2-[2-(2,4-difluorophenyl)ethyl]-4-oxo-1(4H)-quinazolinyl]acetyl}({4'-[(trifluoromethyl)oxy]-4-biphenylyl}methyl)amino]-1-piperidinyl}-2-methylpropanoate as a white solid (149 mg).

LCMS Rt=2.793 minutes; m/z [M+H]⁺=791.3

¹H NMR (CDCl₃) Characteristic peaks: δ 1.20-1.45 (9H, m), 1.58-2.12 (4H, m), 2.14-2.48 (2H, m), 2.620-5.11 (11H, m), 6.59-6.72 (1H, m), 6.73-6.90 (2H, m), 7.16-7.64 (11H, m), 8.25-8.40 (1H, m).

This was converted to the bitartrate salt by a method analogous to that described in Example of Synthesis Approach (II).

Example Synthesis Approach (IV)-8

2-[4-({[2-[2-(2,3-Difluorophenyl)ethyl]-4-oxo-1,8-naphthyridin-1(4H)-yl]acetyl}{[4'-(trifluoromethyl)-4-biphenylyl]methyl}amino)-1-piperidinyl]-2-methylpropanoic acid trifluoroacetate

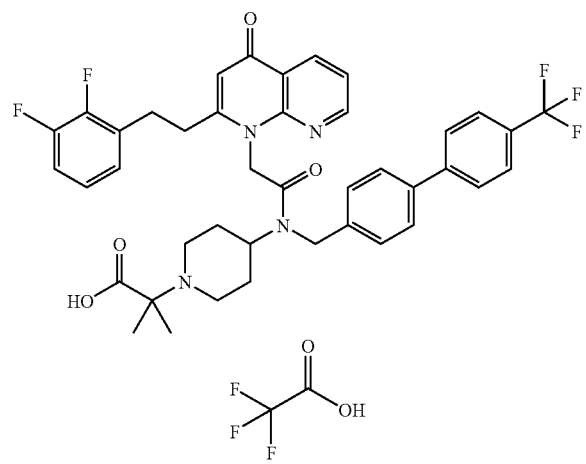

A mixture of 1,1-dimethylethyl 2-methyl-2-[4-({[4'-(trifluoromethyl)-4-biphenylyl]methyl}amino)-1-piperidinyl]propanoate (Int. B4) (1 equiv), [2-[2-(2,3-difluorophenyl)ethyl]-4-oxo-1,8-naphthyridin-1(4H)-yl]acetic acid (Int. C2) (1.2 equiv), DIPEA (3 equiv) and DMF (1.0 ml) is stirred at room temperature for 5 min. HATU (1.5 equiv) is added in 1 portion and stirred an additional 5 min. The crude reaction mixture is concentrated, filtered through a plug of silica eluted with acetone and evaporated to obtain crude 1,1-dimethylethyl 2-[4-({[2-[2-(2,3-difluorophenyl)ethyl]-4-oxo-1,8-naphthyridin-1(4H)-yl]acetyl}{[4'-(trifluoromethyl)-4-biphenylyl]methyl}amino)-1-piperidinyl]-2-methyl propanoate.

The proponate, without isolation, is dissolved in a 1:1 mixture of TFA and DCM and stirred at RT for 4 h. Evaporation and prepative HPLC (Method A) gives the captioned compound.

Other salts can be prepared by conventional means. The free base can also be prepared by conventional means.

Example Synthesis Approach (IV)-9

2-[4-({[2-[2-(2,3-Difluorophenyl)ethyl]-4-oxo-1(4H)-quinazolinyl]acetyl}{[4'-(trifluoromethyl)-4-biphenylyl]methyl}amino)-1-piperidinyl]-2-methylpropanoic acid trifluoroacetate

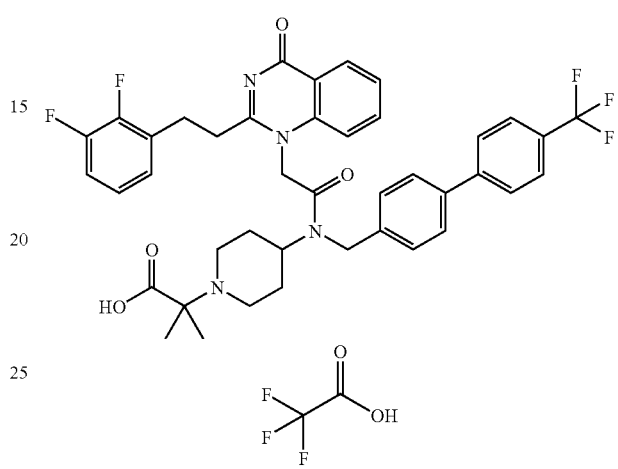

A mixture of 1,1-dimethylethyl 2-methyl-2-[4-({[4'-(trifluoromethyl)-4-biphenylyl]methyl}amino)-1-piperidinyl]propanoate (Int. B4) (1 equiv), [2-[2-(2,3-difluorophenyl)ethyl]-4-oxo-1(4H)-quinazolinyl]acetic acid (Int. C1) (1.2 equiv), DIPEA (3 equiv) and DMF (1.0 ml) is stirred at room temperature for 5 min. HATU (1.5 equiv) is added in 1 portion and stirred an additional 5 min. The crude reaction mixture is concentrated, filtered through a plug of silica eluted with acetone and evaporated to obtain crude 1,1-dimethylethyl 2-[4-({[2-[2-(2,3-difluorophenyl)ethyl]-4-oxo-1(4H)-quinazolinyl]acetyl}{[4'-(trifluoromethyl)-4-biphenylyl]methyl}amino)-1-piperidinyl]-2-methylpropanoate.

The proponate, without isolation, is dissolved in a 1:1 mixture of TFA and DCM and stirred at RT for 4 h. Evaporation and prepative HPLC (Method A) gives the captioned compound.

Example Synthesis Approach (IV)-10

Methyl 2-[4-({[2-[2-(2,3-difluorophenyl)ethyl]-4-oxopyrido[2,3-d]pyrimidin-1(4R)-yl]-acetyl}{[4'-(trifluoromethyl)-4-biphenylyl]methyl}amino)-1-piperidinyl]-2-methylpropanoate

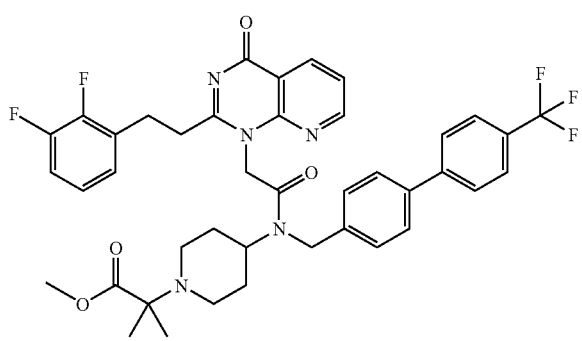

A mixture of [2-[2-(2,3-difluorophenyl)ethyl]-4-oxopyrido[2,3-d]pyrimidin-1(4H)-yl]acetic acid (Int. D1) (20.7 g, 1.3 equiv), methyl 2-methyl-2-[4-({[4'-(trifluoromethyl)-4-biphenylyl]methyl}amino)-1-piperidinyl]propanoate (Int. B1) (20.0 g, 1.3 equiv), DIPEA (24.0 ml, 3 equiv) and DMF (184 ml) was mechanically stirred, then HATU (27.1 g, 1.5 equiv) was added in one portion and stirring continued for 2 h. The reaction mixture was partioned between diethyl ether/THF (1:1) and sodium carbonate (1M, excess). The organic layer was washed with water and brine, dried and evaporated. Chromatography was run sequentially on three silica columns (firstly 3:1 EtOAc/hexanes; secondly 2% MeOH in DCM; thirdly 1:1 EtOAc/hexanes to 100% EtOAc). Product fractions were evaporated to obtain the desired product as an amorphous pink solid (27.5 g).

LCMS Rt=2.702 minutes; m/z [M+H]$^+$=762.3

Crystallisation: A mixture of methyl 2-[4-({[2-[2-(2,3-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoate (8.0 g) and ethanol (200 ml) was warmed until fully dissolved. The solution was stirred magnetically for 24 h at room temperature, then filtered and 7.5 g of solid collected. These solvated crystals were placed into a 60° C. vacuum oven with a nitrogen bleed to hold the vacuum at approximately 630 Torr for 24 h to provide the unsolvated, crystalline title compound (7.15 g), m.p. 150° C.

$^1$H NMR (CD$_3$OD) δ 1.25 (3H, s), 1.30 (3H, s), 1.63-1.99 (4H, m), 2.16-2.28 (1H, m), 2.3-2.43 (1H, m), 2.89-2.98 (1H, m), 2.98-3.08 (2H, m), 3.16-3.30 (3H, m), 3.66-3.69 (3H, m), 4.02/4.38 (1H, 2×br m), 4.69 (1H, s), 4.87 (1H, s), 5.4/5.73 (2H, 2×s), 6.99-7.19 (3H, m), 7.29-7.35 (1H, m), 7.50-7.61 (3H, m), 7.64-7.82 (5H, m), 8.48-8.57 (1H, m), 8.80-8.89 (1H, m) See FIG. 1 below.

Example Synthesis Approach (IV)-11

Methyl 2-[4-({[2-[2-(2,3-difluorophenyl)ethyl]-4-oxopyrido[2,3-d]pyrimidin-1(4H)-yl]-acetyl}{[4'-trifluoromethyl)-4-biphenylyl]methyl}amino)-1-piperidinyl]-2-methylpropanoate 2,3-dihydroxybutanedioate (salt)

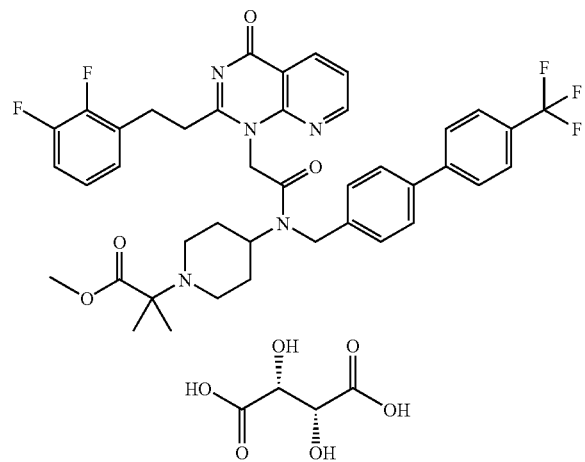

Methyl 2-[4-({[2-[2-(2,3-difluorophenyl)ethyl]-4-oxopyrido[2,3-d]pyrimidin-1(4R)-yl]acetyl}-{[4'-(trifluoromethyl)-4-biphenylyl]methyl}amino)-1-piperidinyl]-2-methylpropanoate (8.5 g, 1 equiv) was suspended in methanol (100 ml) and warmed to 50° C. until the solid dissolved. L-Tartaric acid (1.675 g, 1.0 equiv) was added in one portion and stirred for 30 minutes at room temperature. The solution was concentrated in vacuo to an off-white powder that was dried in a vacuum oven at room temperature.

LCMS Rt=2.697 minutes; m/z [M+H]$^+$=762.3

$^1$H NMR (d$_6$-DMSO) δ 1.17 (3H, s), 1.23 (3H, s), 1.47-1.91 (4H, m), 1.98-2.41 (1H, m), 2.16-2.33 (1H, m), 2.80-3.26 (6H, m), 3.50-3.67 (3H, m), 3.95/4.17 (1H, 2×br m), 4.61 (1H, s), 4.85 (1H, s), 5.39/5.69 (2H, 2×s), 7.08-7.39 (4H, m), 7.53-7.70 (3H, m), 7.72-7.97 (5H, m), 8.42-8.54 (1H, m), 8.85-8.95 (1H, m)

Example Synthesis Approach (IV)-12

Ethyl 2-[4-({[2-[2-(2,3-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoate 2,3-dihydroxybutanedioate (salt)

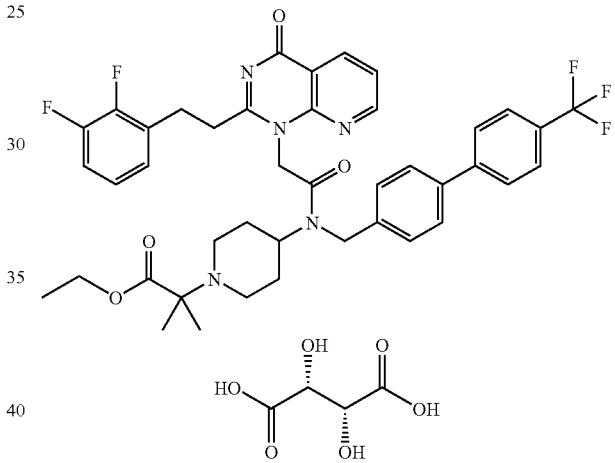

A mixture of [2-[2-(2,3-difluorophenyl)ethyl]-4-oxopyrido[2,3-d]pyrimidin-1(4H)-yl]acetic acid (Int. D1) (116 mg, 1 equiv), ethyl 2-methyl-2-[4-({[4'-trifluoromethyl)-4-biphenyl]-methyl}amino)-1-piperidinyl]propanoate (Int. B2) (150 mg, 1 equiv), HATU (151 mg, 1.2 equiv), DMF (2.72 ml) and DIPEA (0.17 ml, 3 equiv) was shaken at room temperature for 3.25 h. The reaction mixture was partitioned between ethyl acetate/methanol and aqueous sodium bicarbonate, the organic layer was brine-washed, dried and treated with activated charcoal (250 mg). Flash chromatography (silica, 3-4% methanol in DCM) gave ethyl 2-[4-({[2-[2-(2,3-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoate as a white solid (178 mg).

LCMS Rt=2.58 minutes; m/z [M+H]$^+$=776.3

$^1$H NMR (CDCl$_3$) δ 1.20-1.40 (9H, m), 1.56-2.02 (4H, m), 2.19-2.44 (2H, m), 2.88-3.20, (4H, m), 3.22-3.40 (2H, m), 3.81/4.58 (1H, 2×m), 4.11-4.27 (2H, m), 4.69/4.84 (2H, 2×s), 5.17/5.49 (2H, 2×s), 6.95-7.14 (3H, m), 7.25-7.31 (1H, m), 7.38-7.54 (3H, m), 7.54, 7.61 (1H, m), 7.62-7.79 (4H, m), 8.57-8.75 (2H, m)

This was converted to the bitartrate salt by a method analogous to that described for Example of Synthesis Approach (II).

Example Synthesis Approach (IV)-13

Ethyl 2-{4-[{[2-[2-(2,3-difluorophenyl)ethyl]-4-oxopyrido[2,3-d]pyrimidin-1(4H)-yl]acetyl}({4'-[(trifluoromethyl)oxy]-4-biphenylyl}methyl)amino]-1-piperidinyl}-2-methylpropanoate 2,3-dihydroxybutanedioate (salt)

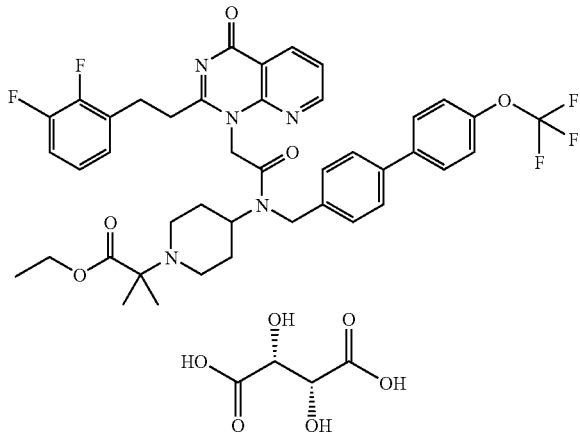

A mixture of [2-[2-(2,3-difluorophenyl)ethyl]-4-oxopyrido[2,3-d]pyrimidin-1(4H)-yl]acetic acid (Int. D1) (114 mg, 1.1 equiv), ethyl 2-methyl-2-{4-[({4'-[(trifluoromethyl)oxy]-4-biphenylyl}methyl)amino]-1-piperidinyl}propanoate (Int. B4) (139 mg, 1 equiv), DMF (1.2 ml) and DIPEA (0.16 ml, 3 equiv) was shaken at room temperature for 30 min, then HATU (176 mg, 1.5 equiv) was added and shaking continued for 3 h. Reverse phase HPLC (Preparative Method B) gave ethyl 2-{4-[{[2-[2-(2,3-difluorophenyl)ethyl]-4-oxo-1(4H)-quinazolinyl]acetyl}({4'-[(trifluoromethyl)oxy]-4-biphenylyl}methyl)amino]-1-piperidinyl}-2-methylpropanoate as a white solid (166 mg).

LCMS Rt=2.87 minutes; m/z [M+H]⁺=792.3

¹H NMR (CDCl₃) δ 1.18-1.42 (9H, m), 1.54-2.04 (4H, m), 2.12-2.46 (2H, m), 2.86-3.21 (4H, m), 3.21-3.41 (2H, m), 3.79/4.57 (1H, 2×m), 4.10-4.27 (2H, m), 4.68 (1H, s), 4.82 (1H, s), 5.17 (1H, s), 5.47 (1H, s), 6.94-7.16 (3H, m), 7.20-7.36 (3H, m), 7.37-7.48 (3H, m), 7.48-7.61 (3H, m), 8.56-8.76 (2H, m).

This was converted to the bitartrate salt by a method analogous to that described for Example of Synthesis Approach (II).

Example Synthesis Approach (IV)-14

1-Methylethyl 2-[4-({[2-[2-(2,3-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoate 2,3-dihydroxybutanedioate (salt)

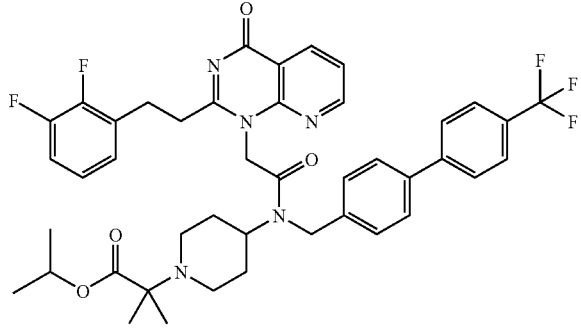 [SMILES: COC(=O)C(C)(C)N1CCC(N(Cc2ccc(-c3ccc(C(F)(F)F)cc3)cc2)C(=O)Cn2c(CCc3cccc(F)c3F)nc(=O)c3cccnc32)CC1]

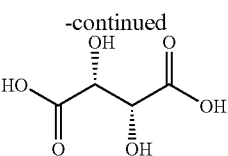

A mixture of 1-methylethyl 2-methyl-2-[4-({[4'-(trifluoromethyl)-4-biphenylyl]methyl}amino)-1-piperidinyl]propanoate (Int. B3) (420 mg, 1 equiv), [2-[2-(2,3-difluorophenyl)ethyl]-4-oxopyrido[2,3-d]pyrimidin-1(4H)-yl]acetic acid (Int. D1) (300 mg, 1 equiv), HATU (396 mg, 1.2 equiv), DIPEA (0.22 ml, 1.5 equiv) and DMF (3.0 ml) was stirred at room temperature for 30 min. The crude reaction mixture was applied directly to reverse-phase HPLC (Preparative Method A) to obtain 1-methylethyl 2-[4-({[2-[2-(2,3-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoate (171 mg).

LCMS Rt=2.837 minutes; m/z [M+H]⁺=790.3

¹H NMR (CD₃OD) δ 1.16-1.37 (12H, m), 1.62-2.01 (4H, m), 2.27-2.55 (2H, m), 2.95-3.12 (3H, m), 3.12-3.29 (3H, m), 4.06/4.40 (1H, 2×br m), 4.71 (1H, s), 4.89 (1H, s), 4.92-5.07 (1H, m), 5.43/5.76 (2H, 2×s), 7.00-7.21 (3H, m), 7.29-7.38 (1H, m), 7.49-7.65 (3H, m), 7.65-7.87 (5H, m), 8.48-8.58 (1H, m), 8.81-8.90 (1H, m).

This was converted to the bitartrate salt by a method analogous to that described for Example of Synthesis Approach (II).

Example Synthesis Approach (IV)-15

1-Methylethyl 2-{4-[{[2-[2-(2,3-difluorophenyl)ethyl]-4-oxopyrido[2,3-c]pyrimidin-1(4H)-yl]acetyl}({4'-[(trifluoromethyl)oxy]-4-biphenylyl}methyl)amino]-1-piperidinyl}-2-methylpropanoate 2,3-dihydroxybutanedioate (salt)

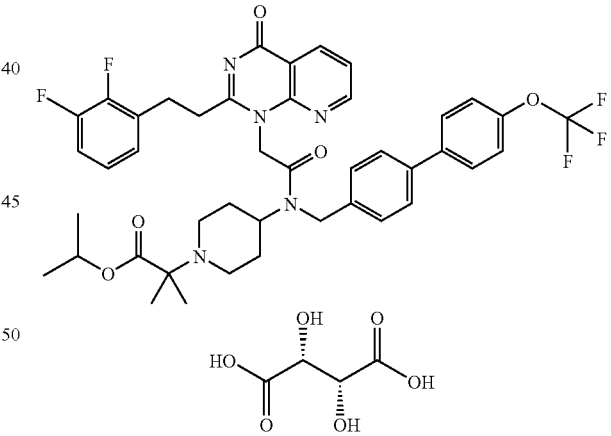

A mixture of 1-methylethyl 2-methyl-2-{4-[({4'-[(trifluoromethyl)oxy]-4-biphenylyl}methyl)-amino]-1-piperidinyl}propanoate (Int. B5) (80 mg, 1 equiv), [2-[2-(2,3-difluorophenyl)ethyl]-4-oxopyrido[2,3-d]pyrimidin-1(4H)-yl]acetic acid (Int. D1) (67 mg, 1 equiv), HATU (400 mg, 5 equiv), DIPEA (0.22 ml, 1.5 equiv) and DMF (2.0 ml) was stirred at room temperature for 30 min. The crude reaction mixture was applied directly to reverse-phase HPLC (Preparative Method A) to obtain 1-methylethyl 2-{4-[{[2-[2-(2,3-difluorophenyl)ethyl]-4-oxopyrido[2,3-d]pyrimidin-1(4H)-yl]acetyl}({4'-[(trifluoromethyl)oxy]-4-biphenylyl}methyl)amino]-1-piperidinyl}-2-methylpropanoate (25 mg).

LCMS Rt=2.952 minutes; m/z [M+H]$^1$=806.4

$^1$H NMR (DMSO-d6) δ 1.09-1.25 (12H, m), 1.47-1.91 (4H, m), 2.05-2.20 (1H, m), 2.21-2.38 (1H, m), 2.87-3.07 (3H, m), 3.08-3.22 (3H, m), 3.95/4.17 (1H, 2×br m), 4.59 (1H, s), 4.75-4.97 (2H, m), 5.38/5.68 (2H, 2×s), 7.90-7.21 (1H, m), 7.21-7.36 (3H, m), 7.42-7.55 (3H, m), 7.55-7.64 (2H, m), 7.66-7.77 (2H, m), 7.77-7.85 (1H, m), 8.43-8.52 (1H, m), 8.86-8.95 (1H, m)

This was converted to the bitartrate salt by a method analogous to that described for Example of Synthesis Approach (II).

Example Synthesis Approach (IV)-16

Methyl 2-[4-({[2-[2-(2,4-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoate 2,3-dihydroxybutanedioate (salt)

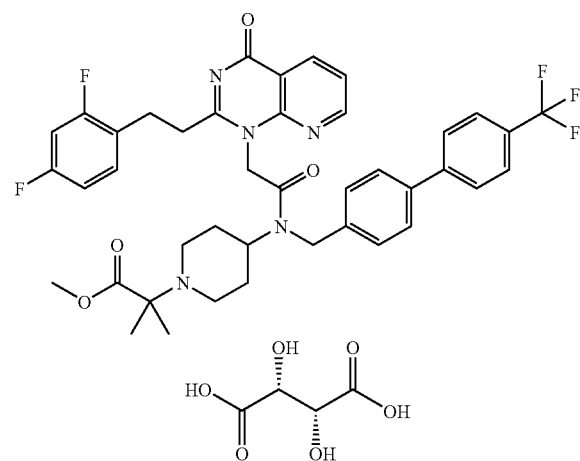

A mixture of [2-[2-(2,4-difluorophenyl)ethyl]-4-oxopyrido[2,4-d]pyrimidin-1(4H)-yl]acetic acid (Int. D2) (100 mg, 1 equiv), methyl 2-methyl-2-[4-({[4'-(trifluoromethyl)-4-biphenylyl]methyl}-amino)-1-piperidinyl]propanoate (Int. B1) (130 mg, 1.03 equiv), DIPEA (0.16 ml, 3 equiv), acetonitrile (2 ml) and HATU (130 mg, 1.2 equiv) was stirred at room temperature for 1 h, then evaporated and redissolved in acetonitrile. Purification by reverse phase HPLC (Preparative Method B) gave methyl 2-[4-({[2-[2-(2,4-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoate (145 mg).

LCMS Rt=2.716 minutes; m/z [M+H]$^+$=762.3

$^1$H NMR (CDCl$_3$) δ 1.27 (3H, s), 1.33 (3H, s), 1.69-1.98 (4H, m), 2.22-2.29 (1H, m), 2.36-2.43 (1H, m), 2.96-3.08 (3H, m), 3.13-3.24 (3H, m), 3.69-3.72 (3H, m), 4.04/4.41 (1H, 2×br m), 4.72 (1H, s), 4.91 (1H, s), 5.41/5.73 (2H, 2×s), 6.84-6.97 (2H, m), 7.34-7.44 (2H, m), 7.54-7.63 (3H, m), 7.69-7.83 (5H, m), 8.55-8.60 (1H, m), 8.86-8.91 (1H, m).

This was converted to the bitartrate salt by a method analogous to that described for Example of Synthesis Approach (II).

Example Synthesis Approach (IV)-17

Ethyl 2-[4-({[2-[2-(2,4-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoate 2,3-dihydroxybutanedioate (salt)

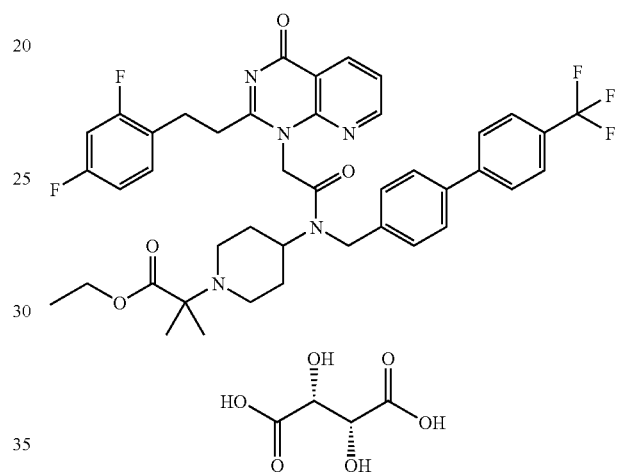

A mixture of [2-[2-(2,4-difluorophenyl)ethyl]-4-oxopyrido[2,4-d]pyrimidin-1(4H)-yl]acetic acid (Int. D2) (120 mg, 1 equiv), ethyl 2-methyl-2-[4-({[4'-trifluoromethyl)-4-biphenyl]-methyl}amino)-1-piperidinyl]propanoate (Int. B2) (198 mg, 1.3 equiv), DMF (1.4 ml) and DIPEA (0.178 ml, 3 equiv) was shaken at room temperature for 1.5 h, then HATU (200 mg, 1.5 equiv) was added with vigorous agitation and shaking continued for 1.5 h. A further portion of Intermediate D2 (12 mg, 0.1 equiv) was added then shaking was continued for 2 days. Reverse phase HPLC (Preparative Method B) gave ethyl 2-[4-({[2-[2-(2,4-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoate as a white solid (170 mg).

LCMS Rt=2.827 minutes; m/z [M+H]$^+$=776.3

$^1$H NMR (CDCl$_3$) Characteristic peaks: δ 1.14-1.43 (9H, m), 1.57-2.05 (4H, m), 2.10-2.46 (2H, m), 2.84-3.11 (3H, m), 3.12-3.34 (3H, m), 3.65/3.85 (1H, m), 4.06-4.27 (2H, m), 4.65/4.85 (2H, s), 5.15/5.45 (2H, s), 6.62-6.89 (2H, m), 7.18-7.34 (1H, m), 7.37-7.82 (9H, m), 8.59-8.77 (2H, m).

This was converted to the bitartrate salt by a method analogous to that described for Example of Synthesis Approach (II).

Example Synthesis Approach (IV)-18

Ethyl 2-{4-[{[2-[2-(2,4-difluorophenyl)ethyl]-4-oxopyrido[2,3-d]pyrimidin-1(4H)-yl]acetyl}({4'-[(trifluoromethyl)oxy]-4-biphenylyl}methyl)amino]-1-piperidinyl}-2-methylpropanoate 2,3-dihydroxybutanedioate (salt)

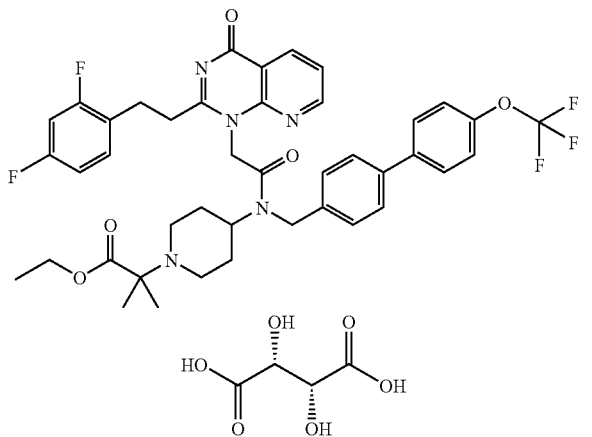

A mixture of 1,1-dimethylethyl 2-methyl-2-[4-({[4'-trifluoromethyl)-4-biphenylyl]methyl}amino)-1-piperidinyl] propanoate (Int. B7) (150 mg, 1 equiv), [2-[2-(2,3-difluorophenyl)ethyl]-4-oxopyrido[2,3-d]pyrimidin-1(4H)-yl] acetic acid (Int. D1) (130 mg, 1.2 equiv), DIPEA (0.164 ml, 3 equiv) and DMF (1.0 ml) was stirred at room temperature for 5 min HATU (180 mg, 1.5 equiv) was added in 1 portion and stirred an additional 5 min. The crude reaction mixture was concentrated, filtered through a plug of silica eluted with acetone and evaporated to obtain crude 1,1-dimethylethyl 2-[4-({[2-[2-(2,3-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoate.

LCMS Rt=2.823 minutes; m/z [M+H]$^+$=804.4

This intermediate, without isolation, was dissolved in a 1:1 mixture of TFA and DCM and stirred at RT for 4 h. Evaporation and prepative HPLC (Method A) gave the desired 2-[4-({[2-[2-(2,3-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoic acid trifluoroacetate (70 mg).

LCMS Rt=2.554 minutes; m/z [M+H]$^+$=748.2

$^1$H NMR (d$_6$-DMSO) d 1.44 (3H, s), 1.51 (3H, s), 1.70-2.30 (4H, m), 2.41-2.56 (2H, m), 2.94-3.54 (6H, m), 4.44-4.95 (3H, m), 5.42/5.76 (2H, 2×br s), 7.07-7.38 (4H, m), 7.54-7.75 (3H, m), 7.76-7.99 (5H, m), 8.42-8.54 (1H, m), 8.85-8.98 (1H, m).

Other salts can be prepared by conventional means. The free base can also be prepared by conventional means.

In some embodiments, compounds useful as inhibitors of Lp-PLA$_2$ useful in the methods as disclosed herein are:
1-(N-(2-(diethylamino)ethyl)-N-(4-(4-trifluoromethylphenyl)benzyl)-aminocarbonylmethyl)-2-(4-fluorobenzyl) thio-5,6-trimethylenepyrimidin-4-one, also referred to as "SB480848" or the USAN name "darapladib" which is a pyrimidinone-based compound and a reversible inhibitor of Lp-PLA$_2$ and is used in the Examples herein;
N-(2-diethylaminoethyl)-2-[2-(2-(2,3-difluorophenyl)ethyl)-4-oxo-4,5,6,7-tetrahydro-cyclopentapyrimidin-1-yl]-N-(4'-trifluoromethyl-biphenyl-4-ylmethyl)acetamide;
N-(1-(2-Methoxyethyl)piperidin-4-yl)-2-[2-(2,3-difluorobenzylthio)-4-oxo-4H-quinolin-1-yl]-N-(4'-trifluoromethylbiphenyl-4-ylmethyl)acetamide; and
methyl 2-[4-({[2-[2-(2,3-difluorophenyl)ethyl]-4-oxopyrido[2,3-d]pyrimidin-1(4H)-yl]-acetyl}{[4'-(trifluoromethyl)-4-biphenylyl]methyl}amino)-1-piperidinyl]-2-methylpropanoate.

Pharmaceutically acceptable salts of 1-(N-(2-(diethylamino)ethyl)-N-(4-(4-trifluoromethylphenyl)benzyl)-aminocarbonylmethyl)-2-(4-fluorobenzyl)thio-5,6-trimethylenepyrimidin-4-one, AKA SB480848, and used in the Examples herein; N-(2-diethylaminoethyl)-2-[2-(2-(2,3-difluorophenyl)ethyl)-4-oxo-4,5,6,7-tetrahydro-cyclopentapyrimidin-1-yl]-N-(4'-trifluoromethyl-biphenyl-4-ylmethyl)acetamide; N-(1-(2-Methoxyethyl)piperidin-4-yl)-2-[2-(2,3-difluorobenzylthio)-4-oxo-4H-quinolin-1-yl]-N-(4'-trifluoromethylbiphenyl-4-ylmethyl)acetamide; and methyl 2-[4-({[2-[2-(2,3-difluorophenyl)ethyl]-4-oxopyrido[2,3-d]pyrimidin-1(4H)-yl]acetyl}{[4'-(trifluoromethyl)-4-biphenylyl]methyl}amino)-1-piperidinyl]-2-methylpropanoate are also useful as inhibitors of Lp-PLA$_2$ for use in the methods as disclosed herein.

Nucleic Acid Inhibitors of Lp-PLA$_2$

In some embodiments, agents that inhibit Lp-PLA$_2$ are nucleic acids. Nucleic acid inhibitors of Lp-PLA2 are, for example, but are not limited to, RNA interference-inducing molecules, for example but are not limited to siRNA, dsRNA, stRNA, shRNA and modified versions thereof, where the RNA interference molecule silences the gene expression of Lp-PLA$_2$. In some embodiments, the nucleic acid inhibitor of Lp-PLA$_2$ is an anti-sense oligonucleic acid, or a nucleic acid analogue, for example but are not limited to DNA, RNA, peptide-nucleic acid (PNA), pseudo-complementary PNA (pc-PNA), or locked nucleic acid (LNA) and the like. In alternative embodiments, the nucleic acid is DNA or RNA, and nucleic acid analogues, for example PNA, pcPNA and LNA. A nucleic acid can be single or double stranded, and can be selected from a group comprising nucleic acid encoding a protein of interest, oligonucleotides, PNA, etc. Such nucleic acid sequences include, for example, but are not limited to, nucleic acid sequence encoding proteins that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc.

In some embodiments single-stranded RNA (ssRNA), a form of RNA endogenously found in eukaryotic cells can be used to form an RNAi molecule. Cellular ssRNA molecules include messenger RNAs (and the progenitor pre-messenger RNAs), small nuclear RNAs, small nucleolar RNAs, transfer RNAs and ribosomal RNAs. Double-stranded RNA (dsRNA) induces a size-dependent immune response such that dsRNA larger than 30 bp activates the interferon response, while shorter dsRNAs feed into the cell's endogenous RNA interference machinery downstream of the Dicer enzyme.

Lp-PLA$_2$ can be reduced by inhibition of the expression of Lp-PLA$_2$ polypeptide or by "gene silencing" methods commonly known by persons of ordinary skill in the art.

RNA interference (RNAi) provides a powerful approach for inhibiting the expression of selected target polypeptides. RNAi uses small interfering RNA (siRNA) duplexes that target the messenger RNA encoding the target polypeptide for selective degradation. siRNA-dependent post-transcriptional silencing of gene expression involves cutting the target messenger RNA molecule at a site guided by the siRNA.

RNA interference (RNAi) is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) *J. of Virology* 76(18):9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease can be of at least 30%, 40%, 50%, 60%, 70%, 80%, 90%, 95% or 99% or more as compared to the expression of a target gene or the activity or level of the protein encoded by a target gene which has not been targeted by an RNA interfering agent.

"Short interfering RNA" (siRNA), also referred to herein as "small interfering RNA" is defined as an agent which functions to inhibit expression of a target gene, e.g., by RNAi. An siRNA can be chemically synthesized, can be produced by in vitro transcription, or can be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and can contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand can precede the nucleotide loop structure and the antisense strand can follow. These shRNAs can be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety).

The target gene or sequence of the RNA interfering agent can be a cellular gene or genomic sequence, e.g. the $Lp-PLA_2$ sequence. An siRNA can be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target.

The siRNA preferably targets only one sequence. Each of the RNA interfering agents, such as siRNAs, can be screened for potential off-target effects by, for example, expression profiling. Such methods are known to one skilled in the art and are described, for example, in Jackson et al, Nature Biotechnology 6:635-637, 2003. In addition to expression profiling, one can also screen the potential target sequences for similar sequences in the sequence databases to identify potential sequences which can have off-target effects. For example, according to Jackson et al. (Id.) 15, or perhaps as few as 11 contiguous nucleotides of sequence identity are sufficient to direct silencing of non-targeted transcripts. Therefore, one can initially screen the proposed siRNAs to avoid potential off-target silencing using the sequence identity analysis by any known sequence comparison methods, such as BLAST.

siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. For example, siRNA containing D-arabinofuranosyl structures in place of the naturally-occurring D-ribonucleosides found in RNA can be used in RNAi molecules according to the present invention (U.S. Pat. No. 5,177,196). Other examples include RNA molecules containing the o-linkage between the sugar and the heterocyclic base of the nucleoside, which confers nuclease resistance and tight complementary strand binding to the oligonucleotides molecules similar to the oligonucleotides containing 2'4)-methyl ribose, arabinose and particularly D-arabinose (U.S. Pat. No. 5,177,196).

The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatized with a variety of groups.

Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases can also be modified. Any modified base useful for inhibiting or interfering with the expression of a target sequence can be used. For example, halogenated bases, such as 5-bromouracil and 5-iodouracil can be incorporated. The bases can also be alkylated, for example, 7-methylguanosine can be incorporated in place of a guanosine residue. Non-natural bases that yield successful inhibition can also be incorporated.

The most preferred siRNA modifications include 2'-deoxy-2'-fluorouridine or locked nucleic acid (LNA) nucleotides and RNA duplexes containing either phosphodiester or varying numbers of phosphorothioate linkages. Such modifications are known to one skilled in the art and are described, for example, in Braasch et al., Biochemistry, 42: 7967-7975, 2003. Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA.

siRNA and miRNA molecules having various "tails" covalently attached to either their 3'- or to their 5'-ends, or to both, are also known in the art and can be used to stabilize the siRNA and miRNA molecules delivered using the methods of the present invention. Generally speaking, intercalating groups, various kinds of reporter groups and lipophilic groups attached to the 3' or 5' ends of the RNA molecules are well known to one skilled in the art and are useful according to the methods of the present invention. Descriptions of syntheses of 3'-cholesterol or 3'-acridine modified oligonucleotides applicable to preparation of modified RNA molecules useful according to the present invention can be found, for example, in the articles: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993).

Other siRNAs useful for targeting Lp-PLA$_2$ expression can be readily designed and tested. Accordingly, siRNAs useful for the methods described herein include siRNA molecules of about 15 to about 40 or about 15 to about 28 nucleotides in length, which are homologous to an Lp-PLA2 gene. Preferably, the Lp-PLA2 targeting siRNA molecules have a length of about 19 to about 25 nucleotides. More preferably, the Lp-PLA2 targeting siRNA molecules have a length of about 19, 20, 21, or 22 nucleotides. The Lp-PLA2 targeting siRNA molecules can also comprise a 3' hydroxyl group. The Lp-PLA2 targeting siRNA molecules can be single-stranded or double stranded; such molecules can be blunt ended or comprise overhanging ends (e.g., 5', 3'). In specific embodiments, the RNA molecule is double stranded and either blunt ended or comprises overhanging ends.

In one embodiment, at least one strand of the Lp-PLA$_2$ targeting RNA molecule has a 3' overhang from about 0 to about 6 nucleotides (e.g., pyrimidine nucleotides, purine nucleotides) in length. In other embodiments, the 3' overhang is from about 1 to about 5 nucleotides, from about 1 to about 3 nucleotides and from about 2 to about 4 nucleotides in length. In one embodiment the Lp-PLA$_2$ targeting RNA molecule is double stranded—one strand has a 3' overhang and the other strand can be blunt-ended or have an overhang. In the embodiment in which the Lp-PLA$_2$ targeting RNA molecule is double stranded and both strands comprise an overhang, the length of the overhangs can be the same or different for each strand. In a particular embodiment, the RNA of the present invention comprises about 19, 20, 21, or 22 nucleotides which are paired and which have overhangs of from about 1 to about 3, particularly about 2, nucleotides on both 3' ends of the RNA. In one embodiment, the 3' overhangs can be stabilized against degradation. In a preferred embodiment, the RNA is stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

Lp-PLA$_2$ mRNA has been successfully targeted using siRNAs and such siRNA or vectors for preparing them are commercially available, for example from Invitrogen. In some embodiments, assessment of the expression and/or knock down of Lp-PLA$_2$ protein using such Lp-PLA$_2$ siRNAs can be determined using commercially available kits, for example but are not limited to PLAC assay from diaDexus. Others can be readily prepared by those of skill in the art based on the known sequence of the target mRNA. To avoid doubt, the sequence of a human Lp-PLA$_2$ cDNA is provided at, for example, GenBank Accession Nos.: U20157 (SEQ ID NO:1) or NM_005084 (SEQ ID NO:2). The sequence at U20157 is the following (SEQ ID NO:1):

```
   1 gctggtcgga ggctcgcagt gctgtcggcg agaagcagtc
     gggtttggag cgcttgggtc
  61 gcgttggtgc gcggtggaac gcgcccaggg accccagttc
     ccgcgagcag ctccgcgccg
 121 cgcctgagag actaagctga aactgctgct cagctcccaa
     gatggtgcca cccaaattgc
 181 atgtgctttt ctgcctctgc ggctgcctgg ctgtggttta
     tccttttgac tggcaataca
 241 taaatcctgt tgcccatatg aaatcatcag catgggtcaa
     caaaatacaa gtactgatgg
 301 ctgctgcaag ctttggccaa actaaaatcc cccggggaaa
     tgggccttat tccgttggtt
 361 gtacagactt aatgtttgat cacactaata agggcacctt
     cttgcgttta tattatccat
 421 cccaagataa tgatcgcctt gacacccttt ggatcccaaa
     taaagaatat ttttggggtc
 481 ttagcaaatt tcttggaaca cactggctta tgggcaacat
     tttgaggtta ctctttggtt
 541 caatgacaac tcctgcaaac tggaattccc ctctgaggcc
     tggtgaaaaa tatccacttg
 601 ttgtttttttc tcatggtctt ggggcattca ggacacttta
     ttctgctatt ggcattgacc
 661 tggcatctca tgggtttata gttgctgctg tagaacacag
     agatagatct gcatctgcaa
 721 cttactattt caaggaccaa tctgctgcag aaataggga
     caagtcttgg ctctacctta
 781 gaaccctgaa acaagaggag gagacacata tacgaaatga
     gcaggtacgg caaagagcaa
 841 aagaatgttc ccaagctctc agtctgattc ttgacattga
     tcatggaaag ccagtgaaga
 901 atgcattaga tttaaagttt gatatggaac aactgaagga
     ctctattgat agggaaaaaa
 961 tagcagtaat tggacattct tttggtggag caacggttat
     tcagactctt agtgaagatc
1021 agagattcag atgtggtatt gccctggatg catggatgtt
     tccactgggt gatgaagtat
```

```
-continued
1081 attccagaat tcctcagccc ctcttttta tcaactctga
     atatttccaa tatcctgcta 1141 atatcataaa aatgaaaaaa tgctactcac ctgataaaga
     aagaaagatg attacaatca 1201 ggggttcagt ccaccagaat tttgctgact tcactttgc
     aactggcaaa ataattggac 1261 acatgctcaa attaaaggga gacatagatt caaatgtagc
     tattgatctt agcaacaaag 1321 cttcattagc attcttacaa aagcatttag gacttcataa
     agattttgat cagtgggact 1381 gcttgattga aggagatgat gagaatctta ttccagggac
     caacattaac acaaccaatc 1441 aacacatcat gttacagaac tcttcaggaa tagagaaata
     caattaggat taaaataggt 1501 tttt
``` siRNA sequences are chosen to maximize the uptake of the antisense (guide) strand of the siRNA into RISC and thereby maximize the ability of RISC to target human Lp-PLA$_2$ mRNA for degradation. This can be accomplished by scanning for sequences that have the lowest free energy of binding at the 5'-terminus of the antisense strand. The lower free energy leads to an enhancement of the unwinding of the 5'-end of the antisense strand of the siRNA duplex, thereby ensuring that the antisense strand will be taken up by RISC and direct the sequence-specific cleavage of the human Lp-PLA$_2$ mRNA.

In a preferred embodiment, the siRNA or modified siRNA is delivered in a pharmaceutically acceptable carrier. Additional carrier agents, such as liposomes, can be added to the pharmaceutically acceptable carrier.

In another embodiment, the siRNA is delivered by delivering a vector encoding small hairpin RNA (shRNA) in a pharmaceutically acceptable carrier to the cells in an organ of an individual. The shRNA is converted by the cells after transcription into siRNA capable of targeting, for example, Lp-PLA$_2$. In one embodiment, the vector can be a regulatable vector, such as tetracycline inducible vector.

In one embodiment, the RNA interfering agents used in the methods described herein are taken up actively by cells in vivo following intravenous injection, e.g., hydrodynamic injection, without the use of a vector, illustrating efficient in vivo delivery of the RNA interfering agents, e.g., the siRNAs used in the methods of the invention.

Other strategies for delivery of the RNA interfering agents, e.g., the siRNAs or shRNAs used in the methods of the invention, can also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. Other delivery methods include delivery of the RNA interfering agents, e.g., the siRNAs or shRNAs of the invention, using a basic peptide by conjugating or mixing the RNA interfering agent with a basic peptide, e.g., a fragment of a TAT peptide, mixing with cationic lipids or formulating into particles.

As noted, the dsRNA, such as siRNA or shRNA can be delivered using an inducible vector, such as a tetracycline inducible vector. Methods described, for example, in Wang et al. Proc. Natl. Acad. Sci. 100: 5103-5106, using pTet-On vectors (BD Biosciences Clontech, Palo Alto, Calif.) can be used. In some embodiments, a vector can be a plasmid vector, a viral vector, or any other suitable vehicle adapted for the insertion and foreign sequence and for the introduction into eukaryotic cells. The vector can be an expression vector capable of directing the transcription of the DNA sequence of the agonist or antagonist nucleic acid molecules into RNA. Viral expression vectors can be selected from a group comprising, for example, reteroviruses, lentiviruses, Epstein Barr virus-, bovine papilloma virus, adenovirus- and adeno-associated-based vectors or hybrid virus of any of the above. In one embodiment, the vector is episomal. The use of a suitable episomal vector provides a means of maintaining the antagonist nucleic acid molecule in the subject in high copy number extra chromosomal DNA thereby eliminating potential effects of chromosomal integration.

RNA interference molecules and nucleic acid inhibitors useful in the methods as disclosed herein can be produced using any known techniques such as direct chemical synthesis, through processing of longer double stranded RNAs by exposure to recombinant Dicer protein or *Drosophila* embryo lysates, through an in vitro system derived from S2 cells, using phage RNA polymerase, RNA-dependant RNA polymerase, and DNA based vectors. Use of cell lysates or in vitro processing can further involve the subsequent isolation of the short, for example, about 21-23 nucleotide, siRNAs from the lysate, etc. Chemical synthesis usually proceeds by making two single stranded RNA-oligomers followed by the annealing of the two single stranded oligomers into a double stranded RNA. Other examples include methods disclosed in WO 99/32619 and WO 01/68836 that teach chemical and enzymatic synthesis of siRNA. Moreover, numerous commercial services are available for designing and manufacturing specific siRNAs (see, e.g., QIAGEN Inc., Valencia, Calif. and AMBION Inc., Austin, Tex.)

In some embodiments, an agent is protein or polypeptide or RNAi agent that inhibits expression of Lp-PLA and/or activity of the Lp-PLA$_2$ protein. In such embodiments cells can be modified (e.g., by homologous recombination) to provide increased expression of such an agent, for example by replacing, in whole or in part, the naturally occurring promoter with all or part of a heterologous promoter so that the cells express the natural inhibitor agent of Lp-PLA$_2$, for example protein or miRNA inhibitor of Lp-PLA$_2$ at higher levels. The heterologous promoter is inserted in such a manner that it is operatively linked to the desired nucleic acid encoding the agent. See, for example, PCT International Publication No. WO 94/12650 by Transkaryotic Therapies, Inc., PCT International Publication No. WO 92/20808 by Cell Genesys, Inc., and PCT International Publication No. WO 91/09955 by Applied Research Systems. Cells also can be engineered to express an endogenous gene comprising the agent under the control of inducible regulatory elements, in which case the regulatory sequences of the endogenous gene can be replaced by homologous recombination. Gene activation techniques are described in U.S. Pat. No. 5,272,071 to Chappel; U.S. Pat. No. 5,578,461 to Sherwin et al.; PCT/US92/09627 (WO93/09222) by Selden et al.; and PCT/US90/06436 (WO91/06667) by Skoultchi et al. The agent can be prepared by culturing transformed host cells under culture conditions suitable to express the miRNA. The resulting expressed agent can then be purified from such culture (i.e., from culture medium or cell extracts) using known purification processes, such as gel filtration and ion exchange chromatography. The purification of the peptide or nucleic acid agent inhibitor of Lp- PLA$_2$ can also include an affinity column containing agents which will bind to the protein; one or more column steps over such affinity resins as concanavalin A-agarose, Heparin-Toyopearl™ or Cibacrom blue 3GA Sepharose; one or more steps involving hydrophobic interaction chromatography using such resins as phenyl ether, butyl ether, or propyl ether; immunoaffinity chromatography, or complementary cDNA affinity chromatography.

In one embodiment, the nucleic acid inhibitors of Lp-PLA$_2$ can be obtained synthetically, for example, by chemically synthesizing a nucleic acid by any method of synthesis known to the skilled artisan. The synthesized nucleic acid inhibitors of Lp-PLA$_2$ can then be purified by any method known in the art. Methods for chemical synthesis of nucleic acids include, but are not limited to, in vitro chemical synthesis using phosphotriester, phosphate or phosphoramidite chemistry and solid phase techniques, or via deoxynucleoside H-phosphonate intermediates (see U.S. Pat. No. 5,705,629 to Bhongle).

In some circumstances, for example, where increased nuclease stability is desired, nucleic acids having nucleic acid analogs and/or modified internucleoside linkages can be preferred. Nucleic acids containing modified internucleoside linkages can also be synthesized using reagents and methods that are well known in the art. For example, methods of synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide (—CH2-S—CH2), dimethylene-sulfoxide (—CH2-SO—CH2), dimethylene-sulfone (—CH2-SO2-CH2), 2'-O-alkyl, and 2'-deoxy-2'-fluoro' phosphorothioate internucleoside linkages are well known in the art (see Uhlmann et al., 1990, Chem. Rev. 90:543-584; Schneider et al., 1990, Tetrahedron Lett. 31:335 and references cited therein). U.S. Pat. Nos. 5,614,617 and 5,223,618 to Cook, et al., 5,714,606 to Acevedo, et al, 5,378,825 to Cook, et al., 5,672,697 and 5,466,786 to Buhr, et al., 5,777,092 to Cook, et al., 5,602,240 to De Mesmacker, et al., 5,610,289 to Cook, et al. and 5,858,988 to Wang, also describe nucleic acid analogs for enhanced nuclease stability and cellular uptake.

Synthetic siRNA molecules, including shRNA molecules, can be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al. (2001) *Nature* 411:494-498; Elbashir, S. M., W. Lendeckel and T. Tuschl (2001) *Genes & Development* 15:188-200; Harborth, J. et al. (2001) *J. Cell Science* 114:4557-4565; Masters, J. R. et al. (2001) *Proc. Natl. Acad. Sci., USA* 98:8012-8017; and Tuschl, T. et al. (1999) *Genes & Development* 13:3191-3197). Alternatively, several commercial RNA synthesis suppliers are available including, but are not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi. In addition, dsRNAs can be expressed as stem loop structures encoded by plasmid vectors, retroviruses and lentiviruses (Paddison, P. J. et al. (2002) *Genes Dev.* 16:948-958; McManus, M. T. et al. (2002) *RNA* 8:842-850; Paul, C. P. et al. (2002) *Nat. Biotechnol.* 20:505-508; Miyagishi, M. et al. (2002) *Nat. Biotechnol.* 20:497-500; Sui, G. et al. (2002) *Proc. Natl. Acad. Sci., USA* 99:5515-5520; Brummelkamp, T. et al. (2002) *Cancer Cell* 2:243; Lee, N. S., et al. (2002) *Nat. Biotechnol.* 20:500-505; Yu, J. Y., et al. (2002) *Proc. Natl. Acad. Sci., USA* 99:6047-6052; Zeng, Y., et al. (2002) *Mol. Cell* 9:1327-1333; Rubinson, D. A., et al. (2003) *Nat. Genet.* 33:401-406; Stewart, S. A., et al. (2003) *RNA* 9:493-501). These vectors generally have a polIII promoter upstream of the dsRNA and can express sense and antisense RNA strands separately and/or as a hairpin structures. Within cells, Dicer processes the short hairpin RNA (shRNA) into effective siRNA.

The targeted region of the siRNA molecule of the present invention can be selected from a given target gene sequence, e.g., a Lp-PLA$_2$ coding sequence, beginning from about 25 to 50 nucleotides, from about 50 to 75 nucleotides, or from about 75 to 100 nucleotides downstream of the start codon. Nucleotide sequences can contain 5' or 3' UTRs and regions nearby the start codon. One method of designing a siRNA molecule of the present invention involves identifying the 23 nucleotide sequence motif AA(N19)TT (where N can be any nucleotide), and selecting hits with at least 25%, 30%, 35%, 40%, 45%, 50%, 55%, 60%, 65%, 70% or 75% G/C content. The "TT" portion of the sequence is optional. Alternatively, if no such sequence is found, the search can be extended using the motif NA(N21), where N can be any nucleotide. In this situation, the 3' end of the sense siRNA can be converted to TT to allow for the generation of a symmetric duplex with respect to the sequence composition of the sense and antisense 3' overhangs. The antisense siRNA molecule can then be synthesized as the complement to nucleotide positions 1 to 21 of the 23 nucleotide sequence motif. The use of symmetric 3' TT overhangs can be advantageous to ensure that the small interfering ribonucleoprotein particles (siRNPs) are formed with approximately equal ratios of sense and antisense target RNA-cleaving siRNPs (Elbashir et al. (2001) supra and Elbashir et al. 2001 supra). Analysis of sequence databases, including but are not limited to the NCBI, BLAST, Derwent and GenSeq as well as commercially available oligosynthesis software such as Oligoengine®, can also be used to select siRNA sequences against EST libraries to ensure that only one gene is targeted.

Delivery of RNA Interfering Agents: Methods of delivering RNA interfering agents, e.g., an siRNA, or vectors containing an RNA interfering agent, to the target cells (e.g., cells of the brain or other desired target cells, for cells in the central and peripheral nervous systems), can include, for example (i) injection of a composition containing the RNA interfering agent, e.g., an siRNA, or (ii) directly contacting the cell, e.g., a cell of the brain, with a composition comprising an RNA interfering agent, e.g., an siRNA. In one embodiment, the RNA interfering agent can be targeted to the bone marrow where the lymphocytes expressing Lp-PLA$_2$ are made. In another embodiment, RNA interfering agents, e.g., an siRNA can be injected directly into any blood vessel, such as vein, artery, venule or arteriole, via, e.g., hydrodynamic injection or catheterization. In yet another embodiment, the RNA interfering agent can be injected or applied topically directly to the site of the skin ulcers.

Administration can be by a single injection or by two or more injections. The RNA interfering agent is delivered in a pharmaceutically acceptable carrier. One or more RNA interfering agents can be used simultaneously. The RNA interfering agents, e.g., the siRNAs targeting Lp-PLA$_2$ mRNA, can be delivered singly, or in combination with other RNA interfering agents, e.g., siRNAs, such as, for example siRNAs directed to other cellular genes. Lp-PLA$_2$ siRNAs can also be administered in combination with other pharmaceutical agents which are used to treat or prevent neurodegenerative diseases or disorders.

In one embodiment, specific cells are targeted with RNA interference, limiting potential side effects of RNA interference caused by non-specific targeting of RNA interference. The method can use, for example, a complex or a fusion molecule comprising a cell targeting moiety and an RNA interference binding moiety that is used to deliver RNA interference effectively into cells. For example, an antibody-protamine fusion protein when mixed with an siRNA, binds siRNA and selectively delivers the siRNA into cells expressing an antigen recognized by the antibody, resulting in silencing of gene expression only in those cells that express the antigen. The siRNA or RNA interference-inducing molecule binding moiety is a protein or a nucleic acid binding domain or fragment of a protein, and the binding moiety is fused to a portion of the targeting moiety. The location of the targeting moiety can be either in the carboxyl-terminal or amino-terminal end of the construct or in the middle of the fusion protein.

A viral-mediated delivery mechanism can also be employed to deliver siRNAs to cells in vitro and in vivo as described in Xia, H. et al. (2002) *Nat Biotechnol* 20(10): 1006). Plasmid- or viral-mediated delivery mechanisms of shRNA can also be employed to deliver shRNAs to cells in vitro and in vivo as described in Rubinson, D. A., et al. ((2003) *Nat. Genet.* 33:401-406) and Stewart, S. A., et al. ((2003) *RNA* 9:493-501).

RNA interfering agents, for e.g., an siRNA, can also be introduced into cells via the vascular or extravascular circulation, the blood or lymph system, and the cerebrospinal fluid.

The dose of the particular RNA interfering agent will be in an amount necessary to effect RNA interference, e.g., post translational gene silencing (PTGS), of the particular target gene, thereby leading to inhibition of target gene expression or inhibition of activity or level of the protein encoded by the target gene.

It is also known that RNAi molecules do not have to match perfectly to their target sequence. Preferably, however, the 5' and middle part of the antisense (guide) strand of the siRNA is perfectly complementary to the target nucleic acid sequence.

Accordingly, the RNAi molecules functioning as nucleic acid inhibitors of $Lp-PLA_2$ in the present invention are for example, but are not limited to, unmodified and modified double stranded (ds) RNA molecules including short-temporal RNA (stRNA), small interfering RNA (siRNA), short-hairpin RNA (shRNA), microRNA (miRNA), double-stranded RNA (dsRNA), (see, e.g. Baulcombe, Science 297: 2002-2003, 2002). The dsRNA molecules, e.g. siRNA, also can contain 3' overhangs, preferably 3'UU or 3'TT overhangs. In one embodiment, the siRNA molecules of the present invention do not include RNA molecules that comprise ssRNA greater than about 30-40 bases, about 40-50 bases, about 50 bases or more. In one embodiment, the siRNA molecules of the present invention are double stranded for more than about 25%, more than about 50%, more than about 60%, more than about 70%, more than about 80%, more than about 90% of their length. In some embodiments, a nucleic acid inhibitor of $Lp-PLA_2$ is any agent which binds to and inhibits the expression of $Lp-PLA_2$ mRNA, where the expression of $Lp-PLA_2$ mRNA or a product of transcription of nucleic acid encoded by SEQ ID NO:1 or 2 is inhibited.

In another embodiment of the invention, agents inhibiting $Lp-PLA_2$ are catalytic nucleic acid constructs, such as, for example ribozymes, which are capable of cleaving RNA transcripts and thereby preventing the production of wildtype protein. Ribozymes are targeted to and anneal with a particular sequence by virtue of two regions of sequence complementary to the target flanking the ribozyme catalytic site. After binding, the ribozyme cleaves the target in a site specific manner. The design and testing of ribozymes which specifically recognize and cleave sequences of the gene products described herein, for example for cleavage of $Lp-PLA_2$ or homologues or variants thereof can be achieved by techniques well known to those skilled in the art (for example Lieber and Strauss, (1995) Mol Cell Biol 15:540.551, the disclosure of which is incorporated herein by reference).

Proteins and Peptide Inhibitors of $Lp-PLA_2$

In some embodiments, agent that inhibit $Lp-PLA_2$ are proteins and/or peptide inhibitors or fragments of inhibitors of $Lp-PLA_2$, for example, but are not limited to mutated proteins; therapeutic proteins and recombinant proteins. Proteins and peptides inhibitors can also include for example mutated proteins, genetically modified proteins, peptides, synthetic peptides, recombinant proteins, chimeric proteins, antibodies, humanized proteins, humanized antibodies, chimeric antibodies, modified proteins and fragments thereof.

In some embodiments, the agents that inhibit $Lp-PLA_2$ are dominant negative variants of $Lp-PLA_2$, for example a non-functional variant of $Lp-PLA_2$.

Antibodies

In some embodiments, inhibitors of genes and/or gene products useful in the methods of the present invention include, for example, antibodies, including monoclonal, chimeric humanized, and recombinant antibodies and antigen-binding fragments thereof. In some embodiments, neutralizing antibodies can be used as inhibitors of the $Lp-PLA_2$ enzyme. Antibodies are readily raised in animals such as rabbits or mice by immunization with the antigen. Immunized mice are particularly useful for providing sources of B cells for the manufacture of hybridomas, which in turn are cultured to produce large quantities of monoclonal antibodies.

In one embodiment of this invention, the inhibitor to the gene products identified herein can be an antibody molecule or the epitope-binding moiety of an antibody molecule and the like. Antibodies provide high binding avidity and unique specificity to a wide range of target antigens and haptens. Monoclonal antibodies useful in the practice of the present invention include whole antibody and fragments thereof and are generated in accordance with conventional techniques, such as hybridoma synthesis, recombinant DNA techniques and protein synthesis.

Useful monoclonal antibodies and fragments can be derived from any species (including humans) or can be formed as chimeric proteins which employ sequences from more than one species. Human monoclonal antibodies or "humanized" murine antibody are also used in accordance with the present invention. For example, murine monoclonal antibody can be "humanized" by genetically recombining the nucleotide sequence encoding the murine Fv region (i.e., containing the antigen binding sites) or the complementarily determining regions thereof with the nucleotide sequence encoding a human constant domain region and an Fc region. Humanized targeting moieties are recognized to decrease the immunoreactivity of the antibody or polypeptide in the host recipient, permitting an increase in the half-life and a reduction the possibly of adverse immune reactions in a manner similar to that disclosed in European Patent Application No. 0,411,893 A2. The murine monoclonal antibodies should preferably be employed in humanized form. Antigen binding activity is determined by the sequences and conformation of the amino acids of the six complementarily determining regions (CDRs) that are located (three each) on the light and heavy chains of the variable portion (Fv) of the antibody. The 25-kDa single-chain Fv (scFv) molecule, composed of a variable region (VL) of the light chain and a variable region (VH) of the heavy chain joined via a short peptide spacer sequence, is the smallest antibody fragment developed to date. Techniques have been developed to display scFv molecules on the surface of filamentous phage that contain the gene for the scFv. scFv molecules with a broad range of antigenic-specificities can be present in a single large pool of scFv-phage library. Some examples of high affinity monoclonal antibodies and chimeric derivatives thereof, useful in the methods of the present invention, are described in the European Patent Application EP 186,833; PCT Patent Application WO 92/16553; and U.S. Pat. No. 6,090,923.

Chimeric antibodies are immunoglobin molecules characterized by two or more segments or portions derived from different animal species. Generally, the variable region of the chimeric antibody is derived from a non-human mammalian antibody, such as murine monoclonal antibody, and the immunoglobin constant region is derived from a human immunoglobin molecule. Preferably, both regions and the combination have low immunogenicity as routinely determined.

One limitation of scFv molecules is their monovalent interaction with target antigen. One of the easiest methods of improving the binding of a scFv to its target antigen is to increase its functional affinity through the creation of a multimer. Association of identical scFv molecules to form diabodies, triabodies and tetrabodies can comprise a number of identical Fv modules. These reagents are therefore multivalent, but monospecific. The association of two different scFv molecules, each comprising a VH and VL domain derived from different parent Ig will form a fully functional bispecific diabody. A unique application of bispecific scFvs is to bind two sites simultaneously on the same target molecule via two (adjacent) surface epitopes. These reagents gain a significant avidity advantage over a single scFv or Fab fragments. A number of multivalent scFv-based structures has been engineered, including for example, miniantibodies, dimeric miniantibodies, minibodies, (scFv)2, diabodies and triabodies. These molecules span a range of valence (two to four binding sites), size (50 to 120 kDa), flexibility and ease of production. Single chain Fv antibody fragments (scFvs) are predominantly monomeric when the VH and VL domains are joined by, polypeptide linkers of at least 12 residues. The monomer scFv is thermodynamically stable with linkers of 12 and 25 amino acids length under all conditions. The noncovalent diabody and triabody molecules are easy to engineer and are produced by shortening the peptide linker that connects the variable heavy and variable light chains of a single scFv molecule. The scFv dimers are joined by amphipathic helices that offer a high degree of flexibility and the miniantibody structure can be modified to create a dimeric bispecific (DiBi) miniantibody that contains two miniantibodies (four scFv molecules) connected via a double helix. Gene-fused or disulfide bonded scFv dimers provide an intermediate degree of flexibility and are generated by straightforward cloning techniques adding a C-terminal Gly4Cys sequence. scFv-CH3 minibodies are comprised of two scFv molecules joined to an IgG CH3 domain either directly (LD minibody) or via a very flexible hinge region (Flex minibody). With a molecular weight of approximately 80 kDa, these divalent constructs are capable of significant binding to antigens. The Flex minibody exhibits impressive tumor localization in mice. Bi- and tri-specific multimers can be formed by association of different scFv molecules. Increase in functional affinity can be reached when Fab or single chain Fv antibody fragments (scFv) fragments are complexed into dimers, trimers or larger aggregates. The most important advantage of multivalent scFvs over monovalent scFv and Fab fragments is the gain in functional binding affinity (avidity) to target antigens. High avidity requires that scFv multimers are capable of binding simultaneously to separate target antigens. The gain in functional affinity for scFv diabodies compared to scFv monomers is significant and is seen primarily in reduced off-rates, which result from multiple binding to two or more target antigens and to rebinding when one Fv dissociates. When such scFv molecules associate into multimers, they can be designed with either high avidity to a single target antigen or with multiple specificities to different target antigens. Multiple binding to antigens is dependent on correct alignment and orientation in the FIT modules. For full avidity in multivalent scFvs target, the antigen binding sites must point towards the same direction. If multiple binding is not sterically possible then apparent gains in functional affinity are likely to be due the effect of increased rebinding, which is dependent on diffusion rates and antigen concentration. Antibodies conjugated with moieties that improve their properties are also contemplated for the instant invention. For example, antibody conjugates with PEG that increases their half-life in vivo can be used for the present invention. Immune libraries are prepared by subjecting the genes encoding variable antibody fragments from the B lymphocytes of naive or immunized animals or patients to PCR amplification. Combinations of oligonucleotides which are specific for immunoglobulin genes or for the immunoglobulin gene families are used. Immunoglobulin germ line genes can be used to prepare semisynthetic antibody repertoires, with the complementarity-determining region of the variable fragments being amplified by PCR using degenerate primers. These single-pot libraries have the advantage that antibody fragments against a large number of antigens can be isolated from one single library. The phage-display technique can be used to increase the affinity of antibody fragments, with new libraries being prepared from already existing antibody fragments by random, codon-based or site-directed mutagenesis, by shuffling the chains of individual domains with those of fragments from naive repertoires or by using bacterial mutator strains.

Alternatively, a SCID-hu mouse, for example the model developed by Genpharm, can be used to produce antibodies, or fragments thereof. In one embodiment, a new type of high avidity binding molecule, termed peptabody, created by harnessing the effect of multivalent interaction is contemplated. A short peptide ligand was fused via a semirigid hinge region with the coiled-coil assembly domain of the cartilage oligomeric matrix protein, resulting in a pentameric multivalent binding molecule. In preferred embodiment of this invention, ligands and/or chimeric inhibitors can be targeted to tissue- or tumor-specific targets by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. Alternatively, two or more active agents and or inhibitors attached to targeting moieties can be administered, wherein each conjugate includes a targeting moiety, for example, a different antibody. Each antibody is reactive with a different target site epitope (associated with the same or a different target site antigen). The different antibodies with the agents attached accumulate additively at the desired target site. Antibody-based or non-antibody-based targeting moieties can be employed to deliver a ligand or the inhibitor to a target site. Preferably, a natural binding agent for an unregulated or disease associated antigen is used for this purpose.

Bioassay for Identifying Lp-PLA$_2$ Inhibitors:

Screen for Inhibition of Lp-PLA$_2$ Protein

In some embodiments, the methods of the present invention relate to the use of inhibitors of Lp-PLA$_2$ for the treatment of skin ulcers. Where necessary, agents that inhibit Lp-PLA$_2$ protein are assessed using a bioassay, as disclosed in U.S. Pat. No. 5,981,252 which is incorporated herein in its entirety by reference. One such assay is testing the effect of the agent on the recombinant Lp-PLA$_2$ protein. In one assay, for example, recombinant Lp-PLA$_2$ is purified to homogeneity from baculovirus infected Sf9 cells, using a zinc chelating column, blue sepharose affinity chromatography and an anion exchange column. Following purification and ultrafiltration, the enzyme can be stored at 6 mg/ml at 4° C. Assay buffer comprises Tris-HCl (50 mM), NaCl (150 mM) and 1 mM CHAPS, pH 7.4 at room temperature. Activity is measured by an increase in emission at 535 nm on hydrolysis of N-((6-(2,4-dinitrophenyl)amino)hexanoyl)-2-(4,4-difluoro-5,7-dimethyl-4-bora-3a,4a-diaza-s-indacene-3-pentanoyl)-1-hexadecanoyl-sn-glycero-3-phosphoethanolamine, triethylammonium salt (PED6, Molecular Probes catalogue reference D-23739) as substrate, using a fluorometric plate reader with 384 well microliter plates. Reaction is initiated by the addition of enzyme (approx 400 pM final by weight) and substrate (5 μM final) to inhibitor in a total volume of 10 microliters.

Regardless of their many causes, skin ulcers are marked by the following characteristics: (1) loss of integrity of the skin area, (2) secondary infection of the site by bacteria, fungus or virus (3) generalized weakness of the patient and (4) delayed healing. Classification systems are used to communicate the severity and depth of an ulcer. It is an easy way to communicate changes for the better, or worse.

Merck Manual classification Stages 1-6 range from:

Stage 1: The skin is red. The underlying tissue is soft. The redness disappears with minor pressure.

Stage 2: There is redness, swelling and hardening of the skin around the area. Sometimes there is blistering. Sometimes there is loss of the superficial skin Stage 3: The skin becomes necrotic. There may be exposure of the fat beneath the skin. The skin may be lost through all its layers.

Stage 4: There is more loss of fat and more necrosis of the skin through to the muscle beneath.

Stage 5: Continuing loss of fat and necrosis of muscle below.

Stage 6: Bone destruction begins with irritation of the bone, erosion of the bone cortex progressing to osteomyelitis—infection of the bone. There may be sepsis of a joint, pathologic fracture or generalized body infection, septicemia.

Another skin ulcer classification is the Pressure Ulcer Scale for Healing (PUSH Tool) developed by the National Pressure Ulcer Advisory Panel (NPUAP) for rating the severity of pressure ulcers. It is used as a quick, reliable tool to monitor the change in pressure ulcer status over time. To use, the first step is to observe and measure the pressure ulcer.

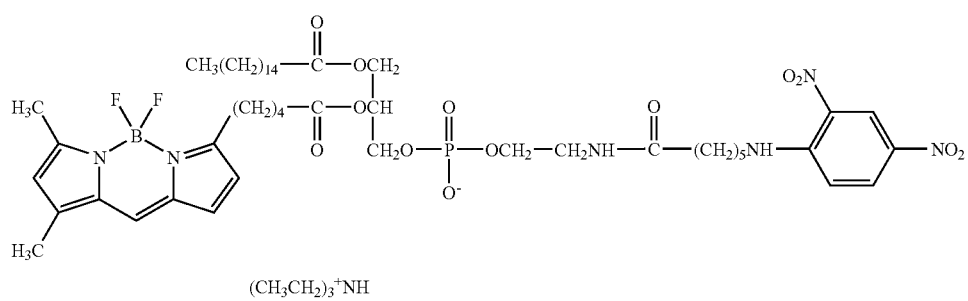

(PED6)

The compounds as disclosed herein, for example as disclosed in the sections entitled of? Examples of synthesis were tested and were found to have IC$_{50}$ values in the range 0.1 to 10 nM.

Skin Ulcers

A skin ulcer is an open sore in the skin. Skin ulcers can be caused by a variety of events, such as trauma, exposure to heat or cold (burns and frost bite), problems with blood circulation, chafing, or irritation from exposure to corrosive material. Pressure ulcers, also known as decubitus ulcers or bedsores, are skin ulcers that develop on areas of the body where the blood supply has been reduced because of prolonged pressure; these may occur in people confined to bed or a chair, or in those who must wear a hard brace or plaster cast. Skin ulcers may become infected, with serious health consequences. Other health conditions that can cause skin ulcers include mouth ulcers (canker sores), chronic venous insufficiency, diabetes, infection, and peripheral vascular disease. Skin ulcers are generally maintained by an inflammation, an infection, and/or medical conditions which impede healing, and are often accompanied by the sloughing-off of inflamed tissue.

Then categorize the ulcer with respect to (1) surface area, (2) exudate-oozing pus, and (3) type of wound tissue. The severity of the ulcer categorized is given a score. For example, in category 3 type of wound tissue: score 4—necrotic tissue (Eschar): black, brown, or tan tissue that adheres firmly to the wound bed or ulcer edges and may be either firmer or softer than surrounding skin; score 3—slough: yellow or white tissue that adheres to the ulcer bed in strings or thick clumps, or is mucinous; score 2-granulation tissue: pink or beefy red tissue with a shiny, moist, granular appearance; score 1-Epithelial Tissue: for superficial ulcers, new pink or shiny tissue (skin) that grows in from the edges or as islands on the ulcer surface; and score 0—closed/resurfaced: the wound is completely covered with epithelium (new skin). Then the sub-scores for each of these ulcer characteristics are recorded. Finally the sub-scores are added to obtain the total score. The smaller the total, the better the ulcer. A comparison of total scores measured over time provides an indication of the improvement or deterioration in pressure ulcer healing. Therefore a gradual trend towards smaller and smaller total score is a good indication that the ulcer is healing. The PUSH tool version 3.0 may be obtained at www.npuap.org/push3-0.htm.

The NPUAP staging of pressure ulcers are as follows:

Stage 1—There is erythema of intact skin which does not blanch with pressure. It may be the heralding lesion of skin ulceration.

Stage 2—There is partial skin loss involving the epidermis, dermis, or both. The ulcer is superficial and presents as an abrasion, blister, or wound with a shallow center.

Stage 3—This is an entire thickness skin loss. It may involve damage to or necrosis of subcutaneous tissue that may extend down to, but not through, the underlying fascia. The ulcer presents as a deep crater with or without undermining of adjacent intact tissues.

Stage 4—Here there is entire thickness skin loss with extensive destruction, tissue necrosis, or damage to muscle, bone, or supporting structures. Tendons, and joints may also be exposed or involved. There may be undermining and/or sinus tracts associated with ulcers at this stage.

A third ulcer classification is the Wagner's classification for rating the severity of diabetic foot ulcerations.

Grade 0—Skin with prior healed ulcer scars, areas of pressure which are sometimes called pre-ulcerative lesion or the presence of bony deformity which puts pressure on an unguarded point.

Grade 1-A—The wound is superficial in nature, with partial or full-thickness skin involvement but does not include tendon, capsule or bone.

Grade 1-B—As above, the wound is superficial in nature, with partial or full thickness skin involvement but not including tendon, capsule nor bone; however the wound is infected. The definition of this wound implies superficial infection without involvement of underlying structures. If the wound shows signs of significant purulence or fluctuance, further exploration to expose a higher grade classification of infection is in order.

Grade 1-C—As above but with vascular compromise.

Grade 1-D—As above but with ischemia. Because ischemia is a type of vascular compromise, the distinction between these two grades is often difficult to make.

Grade 2-A—Penetration through the subcutaneous tissue exposing tendon or ligament, but not bone.

Grade 2-B—Penetration through the deep tissues including tendon or ligament and even joint capsule but not bone.

Grade 2-C—As above 2B, but including ischemia

Grade 2-D—As above 2C, but including infection

Grade 3-A—A wound which probes to bone but shows no signs of local infection nor systemic infection.

Grade 3-B—A wound which probes to bone and is infected.

Grade 3-C—A wound which probes to bone is infected and is ischemic.

Grade 3-D—A wound which probes to bone characterized by active infection, ischemic tissues and exposed bone.

Grade 4—Gangrene of the forefoot

Grade 5—Gangrene of the entire foot

The University of Texas classification of diabetic ulcer is shown below.

Causes of Skin Ulcers

Skin ulcers may result directly or indirectly from many diseases, disorders, and trauma, and may often occur from a combinations of diseases, disorders, and trauma. The causes of skin ulcer may be vascular (venous, arterial, lymphatic, vasculitis), neuropathic (for example, diabetes, spina bifida, leprosy), metabolic (for example, diabetes, gout), connective tissue disease (for example, rheumatoid arthritis, scleroderma, systemic lupus erythematosus), haematological disease (red blood cell disorders (for example, sickle cell disease); white blood cell disorders (for example, leukaemia); platelet disorders (for example, thrombocytosis), immunological (for example, autoimmiune diseases and other inflammatory disorders: rheumatoid arthritis, scleroderma, systemic lupus erythematosus; abberant immune response: pyoderma gangrenosum), dysproteinaemias (for example, cryoglobulinaemia, amyloidosis), immunodeficiency (for example, HIV, immunosuppressive therapy), neoplastic (for example, basal cell carcinoma, squamous cell carcinoma, metastatic disease), infectious (bacterial, fungal, viral), parasitic infection (cutaneous leishmaniasis), panniculitis (for example, necrobiosis lipoidica—a condition, occasionally associated with diabetes, in which shiny atrophic lesions develop on the legs), traumatic (for example, pressure ulcer, radiation damage), iatrogenic (for example, drugs/medication), factitious (for example, self harm, "dermatitis artefacta", and mental illness), and diseases and disorders of unknown etiology (for example, sarcoidosis—a chronic, progressive, generalized granulomatous reticulosis involving almost any organ or tissue, characterized by the presence in all affected tissues of noncaseating epithelioid cell tubercles) (Grey, J. E., et. al., 2006, BMJ 332: 285-288).

Venous ulcers are caused by vascular occlusive or venous disease and they result from insufficient blood flow through the legs, causing blood to pool in the leg veins. Then, pressure increases in the veins and capillaries. The increased pressure causes fluid to leak from the blood vessels into surrounding tissue, and swelling develops. Eventually, swelling interferes with the movement of oxygen and nutrients from capillaries into the tissues. Tissues are damaged because they lack oxygen and nutrients and because the fluid that has leaked puts pressure on them. As a result, venous ulcers may form. Venous ulcers develop mainly in the lower extremities after veins in the legs have been damaged. These ulcers can penetrate deep into the skin.

Any disorder that causes blood to pool in leg veins can cause a venous ulcer. A varicose vein or a vein blocked by a blood clot (deep vein thrombosis) can become damaged, causing blood to pool. Such damage to leg veins is called chronic venous insufficiency. Examples include, but should not be construed to be limited to, congestive heart failure, obesity, renal failure, antiphospholipd-antibody syndrome, livedoid vasculopathy, venous stasis, small-vessel occlusion

|   | 0 | I | II | III |
|---|---|---|---|---|
| A | areas of pressure which are sometimes called pre-ulcerative lesion | superficial ulcer not including tendon, capsula or bone | deep ulcer including tendon, capsula but not bone | deep ulcer including bone and articulation |
| B | infection | infection | infection | infection |
| C | ischemia | ischemia | ischemia | ischemia |
| D | infection + ischemia | infection + ischemia | infection + ischemia | infection + ischemia | arterial disease, type I cryoglobulinemia or Waldenstrom's macroglobulinemia, and Klippel-Trénaunay-Weber syndrome.

Venous ulcers are relatively common among older people. Venous ulcers become infected easily. Occasionally, if a venous ulcer persists for a long time, skin cancer develops at the edge. Areas susceptible to venous ulcers are the foot and leg and are caused by underlying vascular insufficiency. The skin breaks down or fails to heal because of repeated trauma. Even pressure of the nail can cause subungual ulceration. These are most frequently seen in diabetics who have a very low potential to heal from injury.

Vasculitis (plural: vasculitides) is a group of diseases featuring inflammation of the wall of blood vessels due to leukocyte migration and resultant damage. Blood vessels of all sizes may be affected, from the largest vessel in the body (the aorta) to the smallest blood vessels in the skin (capillaries). The size of blood vessel affected varies according to the specific type of vasculitis. Damaged blood vessels lead to ischemic tissue followed by tissue necrosis.

Examples of vasculitides that can produce skin ulcers include Wegener's granulomatosis, polyarteritis nodosa, cryoglobulinemic (mixed) vasculitis, Takayasu's arteritis, and leukocytoclastic vasculitis.

Chronic nonhealing skin ulcers have been observed in a number of cancers: basal cell carcinoma—leg ulcers (Phillips T J, et. al. 1991, J Am Acad Dermatol. July; 25 (1 Pt 1):47-9; Conde-Taboada A, et. al. 2006 J Eur Acad Dermatol Venereol. March; 20(3):359), lymphomas—angiocentric T-cell lymphoma, anaplastic large-cell T-cell lymphoma, and mycosis fungiodes bullosa, leukemiac cutis, and Langerhan's-cell histiocytosis.

Skin infections by various pathogens can also cause skin ulcers. Examples include deep fungal infection: *Sporotrichosis, Aspergillosis, Cryptococcosis, Zygomycosis, Penicillium marneffei* infection; Herpes simplex virus type 2, cutaneous tuberculosis, and amebiasis cutis.

Cutaneous leishmaniasis is skin ulcers caused by the bite of the sandfly depositing the parasites *Leishmania tropica* or *Leishmania major* in bite site. *Leishmania tropica* is found mainly in the urban areas while *Leishmania major* is in dry desert areas.

Diabetes mellitus is a metabolic disorder characterized by hyperglycemia (high blood sugar). Diabetes can cause many complications, of which nerve damage (neuropathy) (of several kinds), microvascular damage, and poor healing frequently contribute to skin ulcer development in the legs and foot. The bottom of the foot is especially prone to skin ulcers in diabetics.

Chronic elevation of blood glucose level leads to damage of blood vessels. In diabetes, the resulting problems are grouped under "microvascular disease" (due to damage to small blood vessels) and "macrovascular disease" (due to damage to the arteries).

Diabetic neuropathy, abnormal and decreased sensation, usually in a 'glove and stocking' distribution starting with the feet but potentially in other nerves, later often fingers and hands. When combined with damaged blood vessels this can lead to diabetic foot.

Diabetic foot, often due to a combination of neuropathy and arterial disease, may cause skin ulcer and infection and, in serious cases, necrosis and gangrene. It is the most common cause of adult amputation, usually of toes and or feet, in the developed world.

Poor healing of wounds, particularly of the feet, can lead to gangrene which can require amputation—the leading cause of non-traumatic amputation in adults in the developed world.

Adequate treatment of diabetes, as well as increased emphasis on blood pressure control and lifestyle factors (such as), may improve the risk profile of most aforementioned complications. (Nathan D M, et. al. N Engl J Med 2005; 353:2643-53. PMID 16371630)

Self-caused skin ulcers may occur in incidences of mental illness such as depression, Munchausen's syndrome, and factitial (factitious) disorder. People with factitial disorder experience dermatitis artefacta, whereby people have injured their own skin, by any method. They may injure their skin by: scratching it, with their fingernails or a knife or other sharp instrument; burning it with fire such as cigarettes, matches, or candles; burning it with caustic chemicals, such as bleach. They may or may not be aware that they caused the damage themselves, but they typically deny having intentionally inflicted the injury.

Skin ulceration may also be associated with certain drugs (iatrogenic ulcers) such as hydroxyurea-induced ulceration (hydroxyurea belongs to a general group of chemotherapy drugs called anti-metabolites), bromoderma (acneform or granulomatous eruption due to hypersensitivity to bromide in anti-convulsion medication) and drug-induced lupus. It is used to treat chronic myeloid leukemia and blood disorders such as Sickle cell anemia), Several inflammatory disorders are associated with skin ulcers. For example: cutaneous Crohn's disease, ulcerative necrobiosis lipoidica, Pyoderma gangrenosum, systemic lupus erythematosus, and Bullous morphea.

Skin ulceration may also be associated with external tissue injury (trauma) such as contact vulvitis (vulvitis is the inflammation of the external female genitalia (vulva)), injection-drug abuse leading to secondary infection, loxoscelism (bite of a brown recluse spider), pathergy (the induction of the inflammatory response after skin trauma) as often seen in pyoderma gangrenosum, and pressure ulcers, by far the most medically significant of all trauma related skin ulcerations. High heat (burns) and extreme cold exposure (frost bite) can also lead to skin ulceration.

A pressure ulcer, also known as bedsores or decubitus ulcers, is an area of skin that breaks down when you stay in one position for too long without shifting your weight. This often happens if you use a wheelchair or you are bedridden, even for a short period of time, for example, after surgery or an injury. The constant pressure against the skin reduces the blood supply to that area, the friction of a resistant surface such as a bed irritates the area with reduced blood flow, and the affected tissue dies.

A pressure ulcer starts as reddened skin but gets progressively worse, forming a blister, then an open sore, and finally a crater. The most common places for pressure ulcers are over bony prominences, where there are less padded by muscle and fat, like the elbow, heels, hips, ankles, shoulders, back, and the back of the head.

Non-mobile patients are vulnerable to the formation pressure sores when left lying for long periods of time in the same prone position. Examples of such patients at risk for developing skin ulcers include but are not limited to diabetics, paraplegic, quadriplegic, the elderly, mobility and/or coordination handicap individuals such as those with neurological defects, for example cerebral palsy and spina bifida, those with neuromuscular diseases such as amyotrophic lateral sclerosis (ALS) and multiple sclerosis (MS), those with autoimmune disease such as scleroderma, and burn victims.

Treatment of Diseases and Disorders Involving Skin Ulcers

Current treatment of vasculitis targets inflammation with steroids (e.g. methylprednisolone, cortisone, and cyclophosphamide) Immunosuppressants such as cyclophosphamide and azathioprine may also be given. In addition, immunosuppressants are used in the treatment of inflammatory diseases.

Pentoxifylline is the standard medication for venous skin ulcers. In combination with standard treatment with compression stockings, oral pentoxifylline is used to improve venous skin ulcer healing. Pentoxifylline reduces the viscosity or "stickiness" of the blood, improving blood circulation. Pentoxifylline also reduces inflammation in the body, which may help ulcers heal as well.

Treatment of type 1 diabetes uses insulin and for type 2 diabetes oral anti-diabetic drug or oral hypoglycemic agent. The drugs generally work by lowering the glucose levels in the blood.

Sulfonylureas were the first widely used oral hypoglycemic medications. They are insulin secretagogues, triggering insulin release by direct action on the KATP channel of the pancreatic beta cells. A secretagogue is a substance which causes another substance to be secreted. Sulfonylureas are only useful in Type II diabetes, as they work by stimulating endogenous release of insulin. Examples of sulfonylureas include but are not limited to: tolbutamide (Orinase); acetohexamide (Dymelor); tolazamide (Tolinase); chlorpropamide (Diabinese); glipizide (Glucotrol); glyburide (Diabeta, Micronase, Glynase); glimepiride (Amaryl); gliclazide (Diamicron)

Amylin analogue, for example Pramlintide; Dipeptidyl peptidase-4 (DPP-4) inhibitors (vildagliptin, sitagliptin); Incretin mimetic GLP analogues for example Exendin-4; Alpha glucosidase inhibitors—miglitol (Glyset) and acarbose (Precose/Glucobay); Biguanides—metformin (Glucophage); Meglitinides—repaglinide (Prandin) and nateglinide (Starlix); PPARsα/γ ligands (muraglitazar, tesaglitazar, and thiazolidinediones-rosiglitazone (Avandia), pioglitazone (Actos), and troglitazone (Rezulin)); SGLT (sodium-dependent glucose transporter 1) inhibitors; and FBPase (fructose 1,6-bisphosphatase) inhibitors (see Lebovitz H E. Therapy for Diabetes Mellitus and Related Disorders. 4th edition. Alexandria: American Diabetes Association, 2004).

Therapies for basal cell carcinoma include photodynamic therapy (the tumour is treated with a photosensitising chemical in a cream (e.g. Metvix) or lotion, and exposed to light several hours later. Up to 85% of superficial basal cell carcinomas are cured, with excellent cosmetic results, using topical imiquimod cream, cryotherapy (freezing), and radiotherapy (X-ray treatment).

The standard treatment for cutaneous leishmaniasis is pentavalent antimony. Other medications include Amphotericin B (Fungizone) (reserved for pentavalent antimony failure), Pentamidine isethionate (Pentam 300), and topical paromomycin.

Care and treatment of pressure ulcers can be found in Brillhart B. Rehabil Nurs. 2005; 30(3): 85-91; de Laat E H, et. al., J Clin Nurs. 2005; 14(4): 464-472; and Cole L and Nesbitt C. Ostomy Wound Manage. 2004; 50(11): 32-40.

One embodiment of the invention encompasses the treatment and/or prevention of skin ulcers in people in need thereof, comprising inhibiting the activity and/or the expression of the $Lp-PLA_2$ protein in combination with anti-microbial therapy, anti-parasitic therapy, anti-obesity therapy, diabetes therapy, cardiovascular disease therapy, renal failure therapy, vasculitis therapy, venous insufficiency therapy, arterial insufficiency therapy, cancer therapy, immunosuppressant therapy, immunodeficiency therapy, steroid therapy, and psychotherapy.

One embodiment of the invention encompasses the treatment and/or prevention of pressure ulcers in people who are bedridden or wheelchair comprising inhibiting the activity and/or the expression of the $Lp-PLA_2$ protein.

One embodiment of the invention encompasses the treatment and/or prevention of skin ulcers in people who are burnt or frost bitten comprising inhibiting the activity and/or the expression of the $Lp-PLA_2$ protein.

Treatments of Skin Ulcers

Skin ulcer management includes, but is not limited to, medications such as anti-bacterial, anti-fungal, anti-parasite, and anti-viral drugs, thrombolytic agent or clot-busting agents such as tissue plasminogen activator (tPA), the use of compression bandages, bioengineered skin substitutes (for example, cultivated epidermal allografts-Apligraf), electrical stimulations, advanced drug delivery systems such as iontophoresis-based transdermal delivery system, localized delivery of materials that promote tissue repair, such as platelet derived and autologous growth factor, granulocyte-macrophage colony stimulating factor (G-M CSF), and mesoglycan, negative pressure wound therapy, and ultrasound.

One embodiment of the invention is the treatment of skin ulcers in a subject having a skin ulcer, comprising inhibiting the activity and/or the expression of the $Lp-PLA_2$ protein in combination with wound management that includes, but is not limited to, anti-pathogen medication, thrombolytic agents, the use of compression bandages, bioengineered skin substitutes, electrical stimulations, advanced drug delivery systems, localized delivery of tissue repair promoting therapy, negative pressure wound therapy, and ultrasound.

Risk Factors for Developing Skin Ulcers

One embodiment of the invention is the prevention of skin ulcer in people at risk of developing the skin ulcers. Making a judgment regarding who is at risk of developing skin ulcers requires identifying the risk factors that may contribute to skin ulceration.

Since skin ulcers may be caused by a great number of diseases, disorders, and traumas, and the combinations thereof, there are a number of factors that increases the risk of developing skin ulcers. These factors include, but are not limited to, having a previous episode of skin ulcer associated with a disease or disorder or trauma as disclosed supra, being elderly, inability to move certain parts of your body without assistance, such as being bedridden or in a wheelchair after spinal or brain injury or if you have a neuromuscular disease (like multiple sclerosis), malnourishment (especially insufficient protein), lack of physical activity, excessive alcohol use, having a chronic condition, such as diabetes, that prevents areas of the body from receiving proper blood flow as disclosed supra; urinary incontinence or bowel incontinence (moisture next to the skin for long periods of time can cause skin irritation that may lead to skin breakdown), fragile skin, mental disability from conditions such as Alzheimer's disease (the patient may not be able to properly prevent or treat pressure ulcers), smoking, having been diagnosed with diabetes, high blood pressure, and/or high levels of homocysteine, being over weight (weighing over 30 percent more than your ideal weight), a family history of varicose veins, especially if one also has reverse blood flow in a saphenous vein, which runs up the inner thigh, having been diagnosed with a blood-clotting disorder such as hypercoagulable state or thrombophilia where blood tends to clot too much, having an occupation that requires many hours of standing, having sickle-cell anemia, are taking bromide-containing medication such as potassium bromide for anti-convulsion therapy, and renal failure.

A complete guide to the prediction and prevention of pressure ulcers can be found in Clinical Practice Guideline Number 3, 1992, AHCPR Pub. No. 92-0047 by the Agency for Health Care Policy and Research (AHCPR).

While having one risk factor does not mean that a subject will develop skin ulcer and thus be treated with an agent that inhibits the activity and/or the expression of the Lp-PLA$_2$ protein, having a combination of risk factors will certainly increase the chance that that subject may eventually develop at least one skin ulcer in that subject's lifetime. Subjects with combinations of two or more or three or more risk factors should be considered by their physician as a candidate for treatment and/or prevention by the methods disclosed herein. For example, a subject who is elderly, diabetic, and has reduced mental ability, or a subject who is obese and immobile are each candidates for treatment as disclosed herein.

There are however some risk factors that, by themselves, are very good indicators that skin ulcers will most likely occur in the subject having that respective risk factor. These are considered "high risk" factors. These include diabetes, vasculitis, leprosy, being bedridden or in a wheelchair, burn or frostbite, taking hydroxyurea-based chemotherapy, and past history of disease/disorder-related skin ulcers. By far the most significant risk factors are diabetes, vasculitis (autoimmune diseases), atherosclerosis, being bedridden, and being in a wheelchair in which there is constant pressure on one part of the skin. Subjects with these factors should be considered by their physician as a candidate for treatment and/or prevention by the present methods disclosed herein.

Formulations of Compositions

Compounds, for example agents inhibiting Lp-PLA$_2$ as disclosed herein, can be used as a medicament or used to formulate a pharmaceutical composition with one or more of the utilities disclosed herein. They can be administered in vitro to cells in culture, in vivo to cells in the body, or ex vivo to cells outside of an individual that can later be returned to the body of the same individual or another. Such cells can be disaggregated or provided as solid tissue.

Compounds, for example agents inhibiting Lp-PLA$_2$ as disclosed herein can be used to produce a medicament or other pharmaceutical compositions. Use of agents inhibiting Lp-PLA$_2$ which further comprise a pharmaceutically acceptable carrier and compositions which further comprise components useful for delivering the composition to an individual are known in the art. Addition of such carriers and other components to the agents as disclosed herein is well within the level of skill in this art.

Pharmaceutical compositions can be administered as a formulation adapted for passage through the blood-brain barrier or direct contact with the endothelium. In some embodiments, the compostions may be administered as a formulation adapted for systemic delivery. In some embodiments, the compostions may be administered as a formulation adapted for delivery to specific organs, for example but not limited to the liver, spleen, the bone marrow, and the skin Alternatively, pharmaceutical compositions can be added to the culture medium of cells ex vivo. In addition to the active compound, such compositions can contain pharmaceutically-acceptable carriers and other ingredients known to facilitate administration and/or enhance uptake (e.g., saline, dimethyl sulfoxide, lipid, polymer, affinity-based cell specific-targeting systems). The composition can be incorporated in a gel, sponge, or other permeable matrix (e.g., formed as pellets or a disk) and placed in proximity to the endothelium for sustained, local release. The composition can be administered in a single dose or in multiple doses which are administered at different times.

Pharmaceutical compositions can be administered by any known route. By way of example, the composition can be administered by a mucosal, pulmonary, topical, or other localized or systemic route (e.g., enteral and parenteral). The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection, infusion and other injection or infusion techniques, without limitation. The phrases "systemic administration," "administered systemically", "peripheral administration" and "administered peripherally" as used herein mean the administration of the agents as disclosed herein such that it enters the animal's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert.

Suitable choices in amounts and timing of doses, formulation, and routes of administration can be made with the goals of achieving a favorable response in the subject with a skin lesion or a risk thereof (i.e., efficacy), and avoiding undue toxicity or other harm thereto (i.e., safety). Therefore, "effective" refers to such choices that involve routine manipulation of conditions to achieve a desired effect.

A bolus of the formulation administered to an individual over a short time once a day is a convenient dosing schedule. Alternatively, the effective daily dose can be divided into multiple doses for purposes of administration, for example, two to twelve doses per day. Dosage levels of active ingredients in a pharmaceutical composition can also be varied so as to achieve a transient or sustained concentration of the compound or derivative thereof in an individual and to result in the desired therapeutic response or protection. But it is also within the skill of the art to start doses at levels lower than required to achieve the desired therapeutic effect and to gradually increase the dosage until the desired effect is achieved.

The amount of agents inhibiting Lp-PLA$_2$ administered is dependent upon factors known to a person skilled in the art such as bioactivity and bioavailability of the compound (e.g., half-life in the body, stability, and metabolism); chemical properties of the compound (e.g., molecular weight, hydrophobicity, and solubility); route and scheduling of administration, and the like. It will also be understood that the specific dose level to be achieved for any particular individual can depend on a variety of factors, including age, gender, health, medical history, weight, combination with one or more other drugs, and severity of disease.

In some embodiments, agents that inhibit Lp-PLA$_2$ as disclosed herein can be combined with other agent, for example therapeutic agent to prevent and/or treatment of skin ulcers or therapeutic agents used to treat diseases and disorders that are associated with skin ulcers. For example, agents include the use of pentoxifylline (venous ski ulcers) and sulfonylureas (diabetes).

Thus, combination treatment with one or more agents that inhibit Lp-PLA$_2$ with one or more other medical procedures can be practiced.

In addition, treatment can also comprise multiple agents to inhibit Lp-PLA$_2$ expression or activity. For example, other agents include the use of statins with Niacin (see http://www.genengnews.com/news/bnitem.aspx?name=6724568) and fenofibrate (see http://www.genengnews.com/news/bnitem.aspx?name=14817756&taxid=19).

The amount which is administered to a subject is preferably an amount that does not induce toxic effects which outweigh the advantages which result from its administration. Further objectives are to reduce in number, diminish in severity, and/or otherwise relieve suffering from the symptoms of the disease in the individual in comparison to recognized standards of care.

Production of compounds according to present regulations will be regulated for good laboratory practices (GLP) and good manufacturing practices (GMP) by governmental agencies (e.g., U.S. Food and Drug Administration). This requires accurate and complete record keeping, as well as monitoring of QA/QC. Oversight of patient protocols by agencies and institutional panels is also envisioned to ensure that informed consent is obtained; safety, bioactivity, appropriate dosage, and efficacy of products are studied in phases; results are statistically significant; and ethical guidelines are followed. Similar oversight of protocols using animal models, as well as the use of toxic chemicals, and compliance with regulations is required.

Dosages, formulations, dosage volumes, regimens, and methods for analyzing results aimed at inhibiting Lp-PLA2 expression and/or activity can vary. Thus, minimum and maximum effective dosages vary depending on the method of administration. Suppression of the symptoms or severity of skin lesions can occur within a specific dosage range, which, however, varies depending on the organism receiving the dosage, the route of administration, whether agents that inhibit Lp-PLA$_2$ are administered in conjunction with other co-stimulatory molecules, and the specific regimen of inhibitor of Lp-PLA$_2$ administration. For example, in general, topical or nasal administration requires a smaller dosage than oral, enteral, rectal, or vaginal administration.

For oral or enteral formulations for use with the present invention, tablets can be formulated in accordance with conventional procedures employing solid carriers well-known in the art. Capsules employed for oral formulations to be used with the methods of the present invention can be made from any pharmaceutically acceptable material, such as gelatin or cellulose derivatives. Sustained release oral delivery systems and/or enteric coatings for orally administered dosage forms are also contemplated, such as those described in U.S. Pat. No. 4,704,295, "Enteric Film-Coating Compositions," issued Nov. 3, 1987; U.S. Pat. No. 4,556,552, "Enteric Film-Coating Compositions," issued Dec. 3, 1985; U.S. Pat. No. 4,309,404, "Sustained Release Pharmaceutical Compositions," issued Jan. 5, 1982; and U.S. Pat. No. 4,309,406, "Sustained Release Pharmaceutical Compositions," issued Jan. 5, 1982.

Examples of solid carriers include starch, sugar, bentonite, silica, and other commonly used carriers. Further non-limiting examples of carriers and diluents which can be used in the formulations of the present invention include saline, syrup, dextrose, and water.

Enteric Coated Formulation

As regards formulations for administering the small chemical entities for inhibitors of Lp-PLA$_2$ of the likes of formulas (I)-(IV) as disclosed herein, one particularly useful embodiment is a tablet formulation comprising the Lp-PLA inhibitor with an enteric polymer casing. An example of such a preparation can be found in WO2005/021002. The active material in the core can be present in a micronised or solubilised form. In addition to active materials the core can contain additives conventional to the art of compressed tablets. Appropriate additives in such a tablet can comprise diluents such as anhydrous lactose, lactose monohydrate, calcium carbonate, magnesium carbonate, dicalcium phosphate or mixtures thereof; binders such as microcrystalline cellulose, hydroxypropylmethylcellulose, hydroxypropyl-cellulose, polyvinylpyrrolidone, pre-gelatinised starch or gum acacia or mixtures thereof; disintegrants such as microcrystalline cellulose (fulfilling both binder and disintegrant functions) cross-linked polyvinylpyrrolidone, sodium starch glycollate, croscarmellose sodium or mixtures thereof; lubricants, such as magnesium stearate or stearic acid, glidants or flow aids, such as colloidal silica, talc or starch, and stabilisers such as desiccating amorphous silica, colouring agents, flavours etc. Preferably the tablet comprises lactose as diluent. When a binder is present, it is preferably hydroxypropylmethyl cellulose. Preferably, the tablet comprises magnesium stearate as lubricant. Preferably the tablet comprises croscarmellose sodium as disintegrant. Preferably, the tablet comprises microcrystalline cellulose.

The diluent can be present in a range of 10-80% by weight of the core. The lubricant can be present in a range of 0.25-2% by weight of the core. The disintegrant can be present in a range of 1-10% by weight of the core. Microcrystalline cellulose, if present, can be present in a range of 10-80% by weight of the core.

The active ingredient preferably comprises between 10 and 50% of the weight of the core, more preferably between 15 and 35% of the weight of the core. (calculated as free base equivalent). The core can contain any therapeutically suitable dosage level of the active ingredient, but preferably contains up to 150 mg as free base of the active ingredient. Particularly preferably, the core contains 20, 30, 40, 50, 60, 80 or 100 mg as free base of the active ingredient. The active ingredient can be present as the free base, or as any pharmaceutically acceptable salt. If the active ingredient is present as a salt, the weight is adjusted such that the tablet contains the desired amount of active ingredient, calculated as free base of the salt. Preferably, the active ingredient is present as a hydrochloride salt.

The core can be made from a compacted mixture of its components. The components can be directly compressed, or can be granulated before compression. Such granules can be formed by a conventional granulating process as known in the art. In an alternative embodiment, the granules can be individually coated with an enteric casing, and then enclosed in a standard capsule casing.

The core is surrounded by a casing which comprises an enteric polymer. Examples of enteric polymers are cellulose acetate phthalate, cellulose acetate succinate, methylcellulose phthalate, ethylhydroxycellulose phthalate, polyvinylacetate phthalate, polyvinylbutyrate acetate, vinyl acetate-maleic anhydride copolymer, styrene-maleic mono-ester copolymer, methyl acrylate-methacrylic acid copolymer or methacrylate-methacrylic acid-octyl acrylate copolymer. These can be used either alone or in combination, or together with other polymers than those mentioned above. The casing can also include insoluble substances which are neither decomposed nor solubilised in living bodies, such as alkyl cellulose derivatives such as ethyl cellulose, crosslinked polymers such as styrene-divinylbenzene copolymer, polysaccharides having hydroxyl groups such as dextran, cellulose derivatives which are treated with bifunctional crosslinking agents such as epichlorohydrin, dichlorohydrin or 1,2-, 3,4-diepoxybutane. The casing can also include starch and/or dextrin.

Preferred enteric coating materials are the commercially available Eudragit® enteric polymers such as Eudragit® L, Eudragit® S and Eudragit® NE used alone or with a plasticiser. Such coatings are normally applied using a liquid medium, and the nature of the plasticiser depends upon whether the medium is aqueous or non-aqueous. Plasticisers for use with aqueous medium include propylene glycol, triethyl citrate, acetyl triethyl citrate or Citroflex® or Citroflex® A2. Non-aqueous plasticisers include these, and also diethyl and dibutyl phthalate and dibutyl sebacate. A preferred plasticiser is Triethyl citrate. The quantity of plasticiser included will be apparent to those skilled in the art.

The casing can also include an anti-tack agent such as talc, silica or glyceryl monostearate. Preferably the anti-tack agent is glyceryl monostearate. Typically, the casing can include around 5-25 wt % Plasticiser and up to around 50 wt % of anti tack agent, preferably 1-10 wt. % of anti-tack agent.

If desired, a surfactant can be included to aid with forming an aqueous suspension of the polymer. Many examples of possible surfactants are known to the person skilled in the art. Preferred examples of surfactants are polysorbate 80, polysorbate 20, or sodium lauryl sulphate. If present, a surfactant can form 0.1-10% of the casing, preferably 0.2-5% and particularly preferably 0.5-2%

In one embodiment, there is a seal coat included between the core and the enteric coating. A seal coat is a coating material which can be used to protect the enteric casing from possible chemical attack by any alkaline ingredients in the core. The seal coat can also provide a smoother surface, thereby allowing easier attachment of the enteric casing. A person skilled in the art would be aware of suitable coatings. Preferably the seal coat is made of an Opadry coating, and particularly preferably it is Opadry White OY-S-28876.

In one embodiment, the pharmaceutically active ingredient is 1-(N-(2-(diethylamino)ethyl)-N-(4-(4-trifluoromethylphenyl)benzyl)aminocarbonylmethyl)-2-(4-fluorobenzyl)thio-5,6-trimethylenepyrimidin-4-one, or a salt thereof.

One example of such an enteric-coated formulation, as described in WO2005/021002, comprises varying amounts of 1-(N-(2-(diethylamino)ethyl)-N-(4-(4-trifluoromethylphenyl)benzyl)aminocarbonylmethyl)-2-(4-fluorobenzyl)thio-5,6-trimethylenepyrimidin-4-one (called "active" in this example) as hydrochloride salt.

In that example, lactose monohydrate, microcrystalline cellulose, the active ingredient, the hydroxypropyl methyl cellulose and half of the croscarmellose sodium were screened into a 10 Liter Fielder high-shear blender (any suitable high shear blender could be used) and blended for 5 minutes at 300 rpm with the chopper off. The mixture was then granulated by the addition of about 750 ml water whilst continuing to blend. The granules were dried in a Glatt 3/5 fluid bed drier, screened by Comil into a Pharmatec 5 Liter bin blender and then blended with any lactose anhydrous given in the formula plus the remainder of the croscarmellose sodium over 5 minutes at 20 rpm. Magnesium stearate was screened into the blender and the mixing process continued for a further 1 minute at 10 rpm. The lubricated mix was compressed using a Riva Piccolla rotary tablet press fitted with 9.5 mm round normal convex punches (any suitable tablet press could be used). The sealcoat, and subsequently the enteric coat, are applied by spraying of an aqueous suspension of the coat ingredients in a Manesty 10 coater using parameters for the coating process as recommended by the manufacturers of the coating polymers (again, any suitable coater could be used).

Other enteric-coated preparations of this sort can be prepared by one skilled in the art, using these materials or their equivalents.

Topical Application

The present invention may be used in topical application for skin ulcers. Such compositions include solutions, suspensions, lotions, gels, creams, ointments, emulsions, skin patches, etc. All of these dosage forms, along with methods for their preparation, are well known in the pharmaceutical and cosmetic art. HARRY'S COMSETICOLOGY (Chemical Publishing, 7th ed. 1982); REMINGTON'S PHARMACEUTICAL SCIENCES (Mack Publishing Co., 18th ed. 1990). Typically, such topical formulations contain the active ingredient in a concentration range of 0.001 to 10 mg/ml, in admixture with suitable vehicles. Other desirable ingredients include preservatives, co-solvents, viscosity building agents, carriers, etc. The carrier itself or a component dissolved in the carrier may have palliative or therapeutic properties of its own, including moisturizing, cleansing, wound healing promoting, or anti-inflammatory. The Lp-PLA$_2$ inhibitors of this application method may be combined with a therapeutically effective amounts of anti-inflammatories such as corticosteroids, fungicides, antibiotics, moisturizers or wound healing promoting compounds such as platelet derived and autologous growth factor, granulocyte-macrophage colony stimulating factor (G-M CSF), and mesoglycan.

Penetration enhancers may, for example, be surface active agents; certain organic solvents, such as di-methylsulfoxide and other sulfoxides, dimethyl-acetamide and pyrrolidone; certain amides of heterocyclic amines, glycols (e.g. propylene glycol); propylene carbonate; oleic acid; alkyl amines and derivatives; various cationic, anionic, nonionic, and amphoteric surface active agents; and the like.

Suitable salve bases contain, for example, vaseline, paraffin, polyethylene, natural hydrogenated or synthetic triglyceride, polyethyleneglycole, macrogoles, carbo waxes, cellulose and its derivatives, high dispersion silicon oxide, bentonite, starches, amylopectic and its derivatives, alginate, tragacanth, polyacrylic acid, polyvinyl alcohols and/or polyorylvinylpyrrolidone. Suitable emulsifiers are, for example, cetylstearylalcohol, cetylesteralcohol, sodium laurylsulfate, sodium cetylsulfate, sodium stearylsulfate, sorbitan ester, polysorbate, and polyoxyethyleneglyceride alcohol ether. Examples of suitable stabilizing agents are ethanol, isopropanol, sorbic acid, paraben (4-hydroxybenzoic acid), parabenester (4-hydroxybenzoic acid ester), methylparaben, propylparaben, hexachlorophen, benzalkonium bromide, cetylpyridinium chloride, and ascorbic acid. Suitable facilitators (also included are penetration enhancers, absorption accelerators and like) are, for example, isopropylmyristate, dimethylsulfoxide, 2-pyrrolidone, 1-dodecylazacycloheptan-2-one, 1,2-propyleneglycol, oleic acid, sodium laurylsulfate, urea, salicylic acid, hyaluronidase, oleyl alcohol, and ethyleneglycol.

The dosage regimen for the active ingredients utilized in the invention depends on the illness or condition to be treated, and is determined by the body weight and age of the patient, and the individual condition of the patient, as well as the applicable art and from the state of the best art.

Topical administration of a pharmacologically effective amount may utilize transdermal delivery systems well known in the art. Preparation of transdermal delivery systems are described in U.S. Pat. Nos. 4,626,539, 4,405,616, 4,416,886, 4,655,766, and Stanley Scheindlin, Molecular Interventions 4:308-312, (2004).

Iontophoresis delivery systems may also be utilized with transdermal delivery systems by one skilled in the art. A example of such application is found in Kazuhiro A, et. al., "Iontophoresis of insulin using a device with microneedles". Int J Pharm Fed World Cong. 2002:62:27.

Efficacy of Treatment:

The term "treatment", with respect to treatment of skin ulcers refers to the control and eradication of infection in the open sore such that the open sore is cleared (absence of pus). It also refers to the gradual healing of the open sore as estimated by shrinkage in open sore size and the opening eventual close completely. It also includes reduction in localized inflammation, soreness, painfulness to touch and redness in the ulcer's surround area. Treatment also means that the ulcer is not becoming larger with time.

Prophylactic methods (e.g., preventing or reducing the incidence of recurrence) are also considered treatment.

The efficacy of treatment can be monitored using any one of the standard scales described herein, or another clinically accepted standard for the measurement of skin ulcer severity. Thus, the Merck Manual Classification (Stages 1-6), the PUSH Tool and NPUAP rating, and/or the Wagner Classification scales can each be used. Treatment is generally considered "effective" if an improvement of at least one stage or level of classification is achieved upon treatment with an Lp-PLA$_2$ inhibitor. Alternatively, or in addition, a reduction in the size (area and/or depth) of a skin lesion by at least 25% following treatment is considered "effective" treatment.

The efficacy of prevention is monitored by evaluating the skin of the subject at risk of developing a skin lesion following the commencement of treatment with an Lp-PLA$_2$ inhibitor. The absence of skin lesions in an at-risk individual is considered a sign of "effective" prevention. Similarly, where an individual has a history of skin lesions, the absence of new lesions, or even a reduction, e.g., by 50% or more, in the frequency or severity of any new lesions, relative to such frequency or severity before treatment, is indicative of "effective" prevention of skin ulcers by the methods described herein.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean±1%.

EXAMPLES

The examples presented herein relate to the methods and compostions for the prevention and/or treatment of skin ulcers, for example but not limited to diabetic skin ulcers by inhibition of Lp-PLA$_2$. Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Animal Model:

A diabetic/diabetic hypercholestrolemic pig model (DM/HC) was developed that mimics human-like diabetes and human-like atherosclerosis. Farm pigs weighing 25-30 kg and aged ~4 months were made diabetic with a single intravenous injection of 125 mg/kg of streptozotocin (Sicor Pharmaceuticals, Irvine, Calif.). After stabilized for 1-2 weeks, the animals with elevated levels of plasma glucose (>150 mg/dl) were fed with atherogenic (high-fat) diet as shown in Table 1 (Animal Specialties, Quakertown, Pa.) to achieve a cholesterol level of approximately 250-800 mg/dl. Maintainance of the cholesterol level was determined by method as shown in Table 2.

TABLE 1

Diet for 2.0% cholesterol diet the components are:

| Component | Weight/Weight % |
| --- | --- |
| Purina* porcine grower meal | 47.5% |
| Lard | 25.0% |
| Casein | 11.1% |
| Dried whole milk | 7.9% |
| Peanut oil | 2.37% |
| Cholesterol | 2.0% |
| Wesson salt mix | 2.37% |
| Purina* vitamin mix | 1.58% |
| Sodium cholate | 1.58% |
| Calcium carbonate | 0.4% |
| Choline chloride | 0.2% |

*Purina Mills, LLC, Checkerboard Square, St. Louis, Missouri, 63164, USA. These feeds were prepared by Animal Specialties and Provisions, LLC, Quakertown, PA USA.

For the 0.5% cholesterol diet the components are similar with the exception of 0.5% cholesterol and 20% lard. The animals were Yorkshire pigs that were castrated males at the age of 3-5 and were obtained from Archer Farms, Darlington, Md. These feeds were prepared by Animal Specialties and Provisions, LLC, Quakertown, Pa. USA.

On days 1-2, animals were fed normal chow, followed by on days 3-14 animals were fed a diet of 0.5% cholesterol, 2% lard and on day 14, cholesterol levels were measured and the diet adjusted accordingly to increase to 2% cholesterol, 10% lard if cholesterol is <300 mg/dl. Following induction of DM/HC, cholesterol was measured until cholesterol levels are stable between 300 and 800 mg/dl, and following cholesterol stabilization, cholesterol was measured monthly. If cholesterol levels were unstable following initial stabilization phase, the diet of the animal was returned to the initial two-week measurement schedule. Monthly cholesterol levels were determined, including levels of total cholesterol, LDL, HDL, VLDL and triglycerides. Adjustment of the diet of the animal for a stable cholersterol level was determined according to the outlines shown in Table 2.

TABLE 2

Cholesterol and Dietry adjustment.

| Cholesterol level | Dietary adjustment | Next measurement | Cholesterol level | Dietary adjustment | Next cholesterol measurement |
|---|---|---|---|---|---|
| <250 mg/dl | Change to 25% lard diet. | 2 weeks | <300 mg/dl | Continue 25% lard diet | 2 weeks |
| | | | 300-800 mg/dl | Change to 75% lard (25% lard): 25% normal diet | 2 weeks |
| | | | >800 mg/dl | Change to 100% 10% lard diet | 2 weeks |
| | | | >1000 mg/dl | Change to 50:50 mix of 10% lard diet | 2 weeks |
| | | | >1500 mg/dl | Change to normal diet | 2 weeks* |
| 300-800 mg/dl | No change. 10% lard diet | 2 weeks | <300 mg/dl | Change to 25% lard diet | 2 weeks |
| | | | 300-800 mg/dl | No change | Regular schedule |
| | | | >800 mg/dl | Change to 50:50 mixture with 10% lard | 2 weeks |
| | | | >1000 mg/dl | Change to 25:75 mixture with 10% lard | 2 weeks |
| | | | >1500 mg/dl | Normal chow | 2 weeks |
| 800-1000 mg/dl | Change to 50:50 mix of 10% lard and normal chow diet. | 2 weeks | <300 mg/dl | Change to 25:75 mixture with 10% lard diet | 2 weeks |
| | | | 300-800 mg/dl | No change in diet (50:50) 10% lard | 2 weeks |
| | | | >800 mg/dl | Change to 25:75 mixture (10% lard) | 2 weeks |
| | | | >1000 mg/dl | Change to 25:75 mixture (10% lard) | 2 weeks |
| | | | >1500 mg/dl | Normal chow | 2 weeks* |
| >1000 mg/dl | 25:75 mix of 10% lard and normal chow diet. | 2 weeks | <300 mg/dl | Change to 50:50 mix of 10% lard and normal chow diet. | 2 weeks |
| | | | 300-800 mg/dl | No change in diet 25:75 mix of 10% lard and normal chow diet | 2 weeks |
| | | | >800 mg/dl | No change in diet | 2 weeks |
| | | | >1000 mg/dl | Normal chow | 2 weeks* |
| | | | >1500 mg/dl | Normal chow | 2 weeks* |
| >1500 mg/dl | Normal chow diet. | 2 weeks | <300 mg/dl | Change to 100% of 10% lard diet. | 2 weeks |
| | | | 300-800 mg/dl | Change diet to 50:50 mix of 10% lard and normal chow diet | 2 weeks |
| | | | >800 mg/dl | Normal chow | 2 weeks* |
| | | | >1000 mg/dl | Normal chow | 2 weeks* |
| | | | >1500 mg/dl | Normal chow | 2 weeks* |

At one month after stabilization of cholersterol at 250-800 mg/dl, the animals were randomized into two experimental groups, DM/HC (hyperglycemia and hypercholesterolemia) group with no treatment and treatment group (10 mg/kg/day of SB-480848, also referred to as 1-(N-(2-(diethylamino) ethyl)-N-(4-(4-trifluoromethylphenyl)benzyl)-aminocarbonylmethyl)-2-(4-fluorobenzyl)thio-5,6-trimethylenepyrimidin-4-one). The animals were then placed into two separate rooms with control animals in one room and treated animals in the other room in order to ensure that no drug would be found in the control animals. The animals were visually inspected twice daily, the visual inspections being between 8-10 hours apart, for skin abscess, especially in the leg and foot. To be considered an abscess, the minimal abscess size was 1 mm with redness in the surrounding area. When abscesses were detected, treatment was applied. Treatment comprise assessing the size and depth of abscess, draining and cleaning the abscess of dead tissue and cells, washing with Betadine, drying and bandaging with sterile dressing, and oral regime of antibiotics. Treatment was applied daily till the infection in the open sore was cleared (absence of pus) and the open sore healed by shrinkage in size and the opening was completely closed. Cultures of the abscess were carried out to determine the pathogen responsible for the infection.

The animals remained in the study for the subsequent 6-months and were sacrificed at the end of the 6 months, and tissues harvested immediately. The animal protocol has been approved by the Institutional Animal Care and Use Committee of University of Pennsylvania.

Two diabetic/hypercholesterolemic groups were evaluated: 1. DM/HC group and 2. DM/HC animals receiving a Lp-PLA$_2$ inhibitors. The experiments included: the control group (DM/HC group—21 pigs) and the experimental group (DM/HC animals receiving Lp-PLA$_2$ inhibitors—22 pigs). In addition blood cholesterol levels were maintained between 300 and 800 mg/dl in experimental animals, this range having been determined to provide a better test model. Blood cholesterol levels were monitored in all animals on a bimonthly basis, as shown in Table 4 and adjustments were made to the fat content of the feed accordingly, as shown in Table 2. The cholesterol and lard percent were in the range of 0.5-2% and 10-25%, respectively, and all animals received feed that contained cholesterol and lard concentration within that range. The timeline of leg abscess identified and treated in the DM/HC animals over the 6 months experimental period is shown in FIG. 1. The summary of leg abscess occurrence is found in Table 4.

The animal number, selected to justify the minimum requirement for statistical validity were 2 groups of animals per experiment as follows: 1. Control group (n=21); Diabetic and hyperlipidemic; 2. Experimental group (n=22) Diabetic, hyperlipidemic receiving 10 mg/kg Lp-PLA$_2$ inhibitor, as shown in Table 3.

Domestic farm pigs, Yorkshire boars, ranging in weight between 25-35 kg were purchased from a local farm and placed in indoor housing under the care of a veterinarian. They were castrated 3-5 days in advance of the study start date. Test pigs were made diabetic by infusing one dose of streptozocin (125 mg/kg) IV in a period of 30 min. If animals do not become diabetic a second dose of (50 mg/kg) was administered. To avoid the possible onset of initial hypoglycemia, 20 g of glucose powder was added to the feed for the first 2. The blood glucose was measured using a glucometer every day before feeding for the first 14 days and then once a week.

Test animals were housed separately from control animals to avoid inter-animal transfer of drug due to colcophagia. All animals were fed an atherogenic diet twice daily with free access to water. The custom-made diet contained 0.5 and 2% cholesterol and 10 and 25% lard, the components of which are shown in Table 1.

TABLE 3

Schedule of animals and procedures (divided into 2 groups):

| | Animal number | Timeline |
|---|---|---|
| Group 1: DM/HC | N = 21 | 7 months |
| Group 2: DM/HC receiving LP-PLA$_2$ inhibitors | N = 22 | 7 months |
| Total | N = 43 | 7 months |

TABLE 4

Summary of Abscess Occurance

| | Abscess Present | Recurrent Abscess | Chronic Abscess |
|---|---|---|---|
| Control Group | 6/21 (29%) | 2/21 (10%) | 1/21 (5%) |
| Treated Group | 2/22 (9%) | 0/22 (0%) | 0/22 (0%) |

Daily dosing began on Day 29, at which time each test animal was given a daily dose of 10 mg/kg SB-480848 (given as bolus equivalent in dog food).

The cultures of the abscess showed that *Staphylococcus* was the predominant pathogens causing the infection. This pathogen is also the most common bacteria isolated in human diabetic infections.

The DM/HC pig model was an ideal model to study the effect of an Lp-PLA$_2$ inhibitor on skin abscess development, formation, treatment, and prevention. This is because these pigs share phenotypically many similarities with high-risk human diabetic patients, such as the tendency to develop diabetic foot ulcers or abscess.

Of the 22 DM/HC pigs treated with the Lp-PLA$_2$ inhibitor, only two pigs, pigs #948 and #963, had visible abscesses on their foot. Each pig had a single abscess. These pigs developed abscesses before the start of the Lp-PLA$_2$ inhibitor treatment (FIG. 1). The abscesses were treated and they healed within average time 1-2 weeks. No further abscess developed after the initiation of daily single dose of inhibitor treatment. For the remaining 20 pigs treated with the Lp-PLA$_2$ inhibitor, no one developed any abscess over the treatment period of 6 months.

Of the 21 DM/HC pigs not treated with the Lp-PLA$_2$ inhibitor (control group), 6 pigs developed abscesses: pigs #975, #1024, #949, #947, #1007, and #15. All these pigs developed abscesses, with two pigs having recurrent abscesses development (new abscess developed after the healing of former abscess), and one pig having a chronic ulceration lasting for >2 months (abscesses that failed to heal despite aggressive wound care).

While not wishing to be bound by theory, it is proposed that the inhibition of the Lp-PLA$_2$ enzyme reduced systemic inflammation, resulting in a reduced risk of skin infection.

Collectively, the data indicate that inhibiting the Lp-PLA$_2$ enzyme can be effective in preventing abscess formation, effective in preventing recurring abscess formation, and also effective in preventing chronic abscess development in diabetic patients.

Moreover during the study period, it was observed that animals that were administered the Lp-PLA$_2$ inhibitor were more responsive to external stimuli, demonstrated increased activity in the cage, and tended to respond more alertly to feeding and handing as compared to the control animals. Also, despite similar serum glucose and cholesterol levels, animals treated with the Lp-PLA$_2$ inhibitor demonstrated an increase in weight as compared to control animals (62.5 kg vs 50.9 kg for control animals) from a baseline of 26.9 kg and 30.3 kg weight respectively. Weight in animals administered the Lp-PLA$_2$ inhibitor is a direct reflection of their overall well-being, insofar as more sickly animals (i.e. the control animals) do not eat. It was observed that inhibition of inflammation by inhibition of Lp-PLA$_2$ results in greater well-being and health in the setting of systemic inflammation.

The references cited herein and throughout the specification are incorporated herein by reference.

What is claimed:

1. A method of treating and/or preventing skin ulcers in a subject, comprising determining whether said subject has or is at risk of having a skin ulcer, and administering a pharmaceutical composition comprising 1-(N-(2-(diethylamino)ethyl)-N-(4-(4-trifluoromethylphenyl)benzyl)aminocarbonylmethyl)-2-(4-fluorobenzyl)thio-5,6-trimethylenepyrimidin-4-one or SB480848 or a pharmaceutically acceptable salt or ester thereof to the subject having a skin ulcer or at risk of developing a skin ulcer.

2. The methods according to claim 1, wherein the subject is a mammal.

3. The method according to claim 2, wherein the mammal is a human.

4. The method according to claim 1, wherein risk factors are selected from a group consisting of:

having a previous episode of skin ulcer; having diabetes; being bedridden or wheelchair bound; and suffering from vasculitis.

* * * * *

SEQUENCE LISTING

<160> NUMBER OF SEQ ID NOS: 4

<210> SEQ ID NO 1
<211> LENGTH: 1505
<212> TYPE: DNA
<213> ORGANISM: Homo sapiens

<400> SEQUENCE: 1

| | | | | | |
|---|---|---|---|---|---|
| gctggtcgga | ggctcgcagt | gctgtcggcg | agaagcagtc | gggtttggag | cgcttgggtc | 60 |
| gcgttggtgc | gcggtggaac | gcgcccaggg | accccagttc | ccgcgagcag | ctccgcgccg | 120 |
| cgcctgagag | actaagctga | aactgctgct | cagctcccaa | gatggtgcca | cccaaattgc | 180 |
| atgtgctttt | ctgcctctgc | ggctgcctgg | ctgtggttta | tccttttgac | tggcaataca | 240 |
| taaatcctgt | tgcccatatg | aaatcatcag | catgggtcaa | caaaatacaa | gtactgatgg | 300 |
| ctgctgcaag | ctttggccaa | actaaaatcc | cccggggaaa | tgggccttat | tccgttggtt | 360 |
| gtacagactt | aatgtttgat | cacactaata | agggcacctt | cttgcgttta | tattatccat | 420 |
| cccaagataa | tgatcgcctt | gacacccttt | ggatcccaaa | taagaatat | ttttggggtc | 480 |
| ttagcaaatt | tcttggaaca | cactggctta | tgggcaacat | tttgaggtta | ctctttggtt | 540 |
| caatgacaac | tcctgcaaac | tggaattccc | ctctgaggcc | tggtgaaaaa | tatccacttg | 600 |
| ttgttttttc | tcatggtctt | ggggcattca | ggacacttta | ttctgctatt | ggcattgacc | 660 |
| tggcatctca | tgggtttata | gttgctgctg | tagaacacag | agatagatct | gcatctgcaa | 720 |
| cttactattt | caaggaccaa | tctgctgcag | aaatagggga | caagtcttgg | ctctacctta | 780 |
| gaaccctgaa | acaagaggag | gagacacata | tacgaaatga | gcaggtacgg | caaagagcaa | 840 |
| aagaatgttc | ccaagctctc | agtctgattc | ttgacattga | tcatggaaag | ccagtgaaga | 900 |
| atgcattaga | tttaaagttt | gatatggaac | aactgaagga | ctctattgat | agggaaaaaa | 960 |
| tagcagtaat | tggacattct | tttggtggag | caacggttat | tcagactctt | agtgaagatc | 1020 |
| agagattcag | atgtggtatt | gccctggatg | catggatgtt | tccactgggt | gatgaagtat | 1080 |
| attccagaat | tcctcagccc | ctctttttta | tcaactctga | atatttccaa | tatcctgcta | 1140 |
| atatcataaa | aatgaaaaaa | tgctactcac | ctgataaaga | aagaaagatg | attacaatca | 1200 |
| ggggttcagt | ccaccagaat | tttgctgact | tcacttttgc | aactggcaaa | ataattggac | 1260 |
| acatgctcaa | attaaaggga | gacatagatt | caaatgtagc | tattgatctt | agcaacaaag | 1320 |
| cttcattagc | attcttacaa | aagcatttag | gacttcataa | agattttgat | cagtgggact | 1380 |
| gcttgattga | aggagatgat | gagaatctta | ttccagggac | caacattaac | acaaccaatc | 1440 |
| aacacatcat | gttacagaac | tcttcaggaa | tagagaaata | caattaggat | taaaataggt | 1500 |
| ttttt | | | | | | 1505 |

<210> SEQ ID NO 2

<400> SEQUENCE: 2

000

<210> SEQ ID NO 3

<400> SEQUENCE: 3

000

```
<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(21)
<223> OTHER INFORMATION: a, c, t, g, unknown or other

<400> SEQUENCE: 4
aannnnnnnn nnnnnnnnnn ntt                                              23
```